United States Patent
Cui et al.

(10) Patent No.: US 12,239,018 B2
(45) Date of Patent: Feb. 25, 2025

(54) ORGANIC ELECTROLUMINESCENT MATERIALS AND DEVICES

(71) Applicant: BEIJING SUMMER SPROUT TECHNOLOGY CO., LTD., Beijing (CN)

(72) Inventors: Zhihao Cui, Beijing (CN); Hualong Ding, Beijing (CN); Chi Yuen Raymond Kwong, Beijing (CN); Chuanjun Xia, Beijing (CN); Juntao Hu, Beijing (CN); Xiao Chen, Beijing (CN)

(73) Assignee: BEIJING SUMMER SPROUT TECHNOLOGY CO., LTD., Beijing (CN)

( * ) Notice: Subject to any disclaimer, the term of this patent is extended or adjusted under 35 U.S.C. 154(b) by 1016 days.

(21) Appl. No.: 17/182,611

(22) Filed: Feb. 23, 2021

(65) Prior Publication Data

US 2021/0280795 A1    Sep. 9, 2021

Related U.S. Application Data

(60) Provisional application No. 62/982,765, filed on Feb. 28, 2020.

(30) Foreign Application Priority Data

Jan. 22, 2021 (CN) .......................... 202110081423.0

(51) Int. Cl.
*H10K 85/60* (2023.01)
*C07D 498/04* (2006.01)
(Continued)

(52) U.S. Cl.
CPC ......... *H10K 85/657* (2023.02); *C07D 498/04* (2013.01); *C09K 11/06* (2013.01);
(Continued)

(58) Field of Classification Search
CPC ... H10K 85/657; H10K 50/131; C07D 498/04
See application file for complete search history.

(56) References Cited

U.S. PATENT DOCUMENTS

| 5,703,436 | A | 12/1997 | Forrest et al. |
| 5,707,745 | A | 1/1998 | Forrest et al. |
| (Continued) | | | |

FOREIGN PATENT DOCUMENTS

| CN | 109912619 | 6/2019 |
| CN | 112745333 | 5/2021 |
| JP | 2009242339 | 10/2009 |

OTHER PUBLICATIONS

Chinese *First Office Action for Chinese Application No. 202110081423.0, dated Feb. 25, 2022, 7 pages with translation.
(Continued)

*Primary Examiner* — Sean M DeGuire
(74) *Attorney, Agent, or Firm* — Workman Nydegger

(57) ABSTRACT

An organic electroluminescent material is disclosed. The organic electroluminescent material is novel dehydro-fused-ring compounds with a structure of $B(A)_2$, which may be used as charge transporting materials, charge injection materials, and the like in organic electroluminescent devices. Such novel compounds have very deep LUMO energy level, so they are excellent electron acceptor materials and charge transfer materials. They also have the potential to be excellent hole injection materials and p-dopant materials, and have broad industrial application prospects. An electroluminescent device and a compound formulation are also disclosed.

33 Claims, 3 Drawing Sheets

(51) Int. Cl.
*C09K 11/06* (2006.01)
*H10K 50/15* (2023.01)
*H10K 50/17* (2023.01)

(52) U.S. Cl.
CPC ...... *C09K 2211/1018* (2013.01); *H10K 50/15* (2023.02); *H10K 50/17* (2023.02)

(56) References Cited

U.S. PATENT DOCUMENTS

| | | | |
|---|---|---|---|
| 5,844,363 | A | 12/1998 | Gu et al. |
| 6,097,147 | A | 8/2000 | Baldo et al. |
| 6,303,238 | B1 | 10/2001 | Thompson et al. |
| 7,279,704 | B2 | 10/2007 | Walters et al. |
| 7,968,416 | B2 | 6/2011 | Bottner et al. |
| 2003/0230980 | A1 | 12/2003 | Forrest et al. |
| 2004/0174116 | A1 | 9/2004 | Lu et al. |
| 2009/0079329 | A1* | 3/2009 | Murakami ............ H05B 33/14 313/504 |
| 2015/0349273 | A1 | 12/2015 | Hung et al. |
| 2016/0013428 | A1* | 1/2016 | Takimiya ............. C07D 493/04 252/500 |
| 2016/0359122 | A1 | 12/2016 | Boudreault et al. |
| 2019/0181349 | A1 | 6/2019 | Xia |
| 2020/0062778 | A1 | 2/2020 | Cui et al. |
| 2020/0087311 | A1 | 3/2020 | Cui et al. |
| 2021/0119162 | A1 | 4/2021 | Gao et al. |
| 2021/0296594 | A1 | 9/2021 | Ding et al. |

OTHER PUBLICATIONS

Chinese Search Report for Chinese Application No. 2021100814230.0, dated Feb. 11, 2022, 3 pages.

Novel Electron Acceptors Bearing a Heteroquinonoid System. 4. Syntheses, Properties, and Charge-Transfer Complexes of 2,7-Bis(dicyanomethylene)-2,7-dihydrobenzo[2,1-b:3,4-b']dithiophene, 2,7-Bis(dicyanomethylene)-2,7-dihydrobenzo[1,2-b:4,3-b']dithiophene, and 2,6-Bis(dicyanomethylene)-2,6-dihydrobenzo[1,2-b:4,5-b']dithiophene, Shu Yoshida et al., vol. 59, No. 11, p. 3077-3081, Dec. 31, 1994.

Tang et al., Organic electroluminescent diodes, Applied Physics Letter, (available at http://apl.aip.org/resource/1/APPLAB/v51/i12), 4 pages.

Joyama et al., Highly efficient organic light-emitting diodes from delayed fluorescence, Nature, vol. 492, (2012), pp. 234-241.

* cited by examiner

ORGANIC ELECTROLUMINESCENT MATERIALS AND DEVICES

CROSS-REFERENCE TO RELATED APPLICATIONS

This application claims priority to U.S. Provisional Application No. 62/982,765, filed Feb. 28, 2020, and Chinese Patent Application CN 202110081423.0, filed Jan. 22, 2021, the disclosures of which are incorporated herein by reference in their entireties.

TECHNICAL FIELD

The present disclosure relates to a compound for use in organic electronic devices, such as organic light-emitting devices. More specifically, it relates to a compound having a novel structure of dehydro-fused-ring, and an organic electroluminescent device and a compound formulation comprising the compound.

BACKGROUND

Organic electronic devices include, but are not limited to, the following types: organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. This invention laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since OLED is a self-emitting solid state device, it offers tremendous potential for display and lighting applications. In addition, the inherent properties of organic materials, such as their flexibility, may make them well suited for particular applications such as fabrication on flexible substrates.

OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of a fluorescent OLED is only 25%. This limitation hindered the commercialization of OLED. In 1997, Forrest and Thompson reported phosphorescent OLED, which uses triplet emission from heave metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. Small molecule refers to any organic or organometallic material that is not a polymer. The molecular weight of a small molecule can be large as long as it has well defined structure. Dendrimers with well-defined structures are considered as small molecules. Polymer OLEDs include conjugated polymers and non-conjugated polymers with pendant emitting groups. Small molecule OLED can become a polymer OLED if post polymerization occurred during the fabrication process.

There are various methods for OLED fabrication. Small molecule OLEDs are generally fabricated by vacuum thermal evaporation. Polymer OLEDs are fabricated by solution process such as spin-coating, inkjet printing, and slit printing. If the material can be dissolved or dispersed in a solvent, the small molecule OLED can also be produced by solution process.

The emitting color of an OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent emitters still suffer from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

In an OLED device, a hole injection layer (HIL) facilitates hole injection from the ITO anode to the organic layers. To achieve a low device driving voltage, it is important to have a minimum charge injection barrier from the anode. Various HIL materials have been developed, such as triarylamine compounds having a shallow HOMO energy levels, very electron deficient heterocycles, and triarylamine compounds doped with P-type conductive dopants. To improve OLED performance, such as longer device lifetime, higher efficiency and/or lower voltage, it is crucial to develop HIL, HTL materials with better performance.

The organic light emitting display device uses a hole injection layer and an electron injection layer to promote charge injection. The hole injection layer is a functional layer formed from a single material or more than one material. Methods involving a single material generally utilize materials with deep LUMO levels while methods involving more than one material are performed by doping a hole transporting material with a P-type, deep-LUMO material. The commonality between these two methods is the use of deep-LUMO materials.

However, materials with deep LUMO levels are not easily synthesized due to their substituents with strong electron-withdrawing ability, and it is difficult to possess both deep LUMO level, high stability, and high film-forming ability. For example, F4-TCNQ (a P-type hole injection material), although having a deep LUMO level, has an extremely low vapor deposition temperature, affecting deposition control and production performance reproducibility and device thermal stability; and, for another example, HATCN has problems in film formation in devices due to strong crystallinity, and the LUMO level thereof is not deep enough to be used as a P-type dopant. Since the hole injection layer has a great influence on the voltage, efficiency and lifetime of an OLED device, it is very important and urgent in the industry for the development of materials with a deep LUMO level, high stability and high film-forming ability.

SUMMARY

The present disclosure aims to provide a series of compounds having a novel structure of dehydro-fused-ring to address at least some of the above problems. The compounds can be used as charge-transporting materials, charge injection materials and the like in organic electroluminescent devices. Such novel compounds have very deep LUMO energy level, so they are excellent electron acceptor materials and charge transfer materials. They also have the potential to be excellent hole injection materials and p-dopant materials, and have broad industrial application prospects.

According to an embodiment of the present disclosure, a compound having a structure of B(A)$_2$ is disclosed, wherein A has a structure of Formula 1:

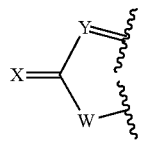

Formula 1 wherein,
X is, at each occurrence identically or differently, selected from the group consisting of O, S, Se, NR' and CR"R'";
Y is, at each occurrence identically or differently, selected from the group consisting of CR$_Y$ and N;
W is, at each occurrence identically or differently, selected from the group consisting of O, S, Se and NR$_N$;
wherein, B is selected from a substituted or unsubstituted conjugated unsaturated fused aryl ring having 10 to 30 ring atoms, or a substituted or unsubstituted conjugated unsaturated fused heteroaryl ring having 10 to 30 ring atoms, or selected from the structure represented by one of Formula 2 to Formula 8, or combinations thereof:

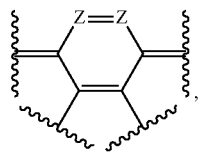

Formula 2

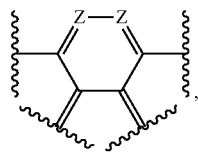

Formula 3

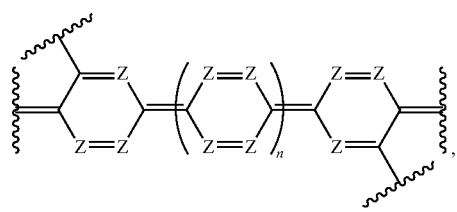

Formula 4

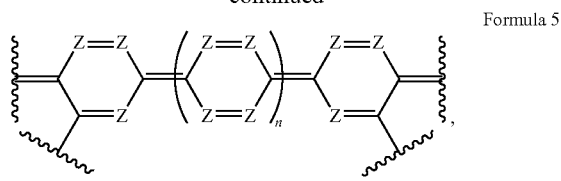

Formula 5

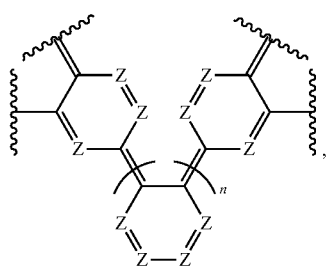

Formula 6

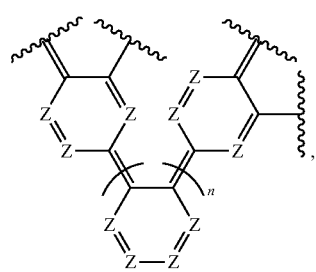

Formula 7

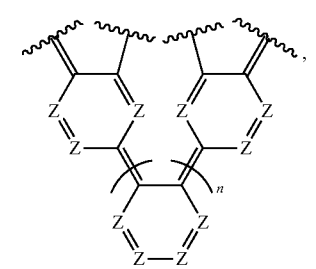

Formula 8 wherein B is fused with each of A through a single bond and a double bond;
wherein Z is, at each occurrence identically or differently, selected from the group consisting of CR and N; n is, at each occurrence identically or differently, selected from 0, 1, or 2;
wherein, R, R', R", R'", R$_N$ and R$_Y$ are, at each occurrence identically or differently, selected from the group consisting of hydrogen, deuterium, halogen, nitroso, nitro, acyl, carbonyl, a carboxylic acid group, an ester group, cyano, isocyano, SCN, OCN, SF$_5$, boranyl, sulfinyl, sulfonyl, phosphoroso, sulfanyl, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein at least one of R, R', R", R''', $R_N$ and $R_Y$ is a group having at least one electron-withdrawing group; and wherein any two adjacent substituents R, R', R", R''', $R_N$ and $R_Y$ can be optionally joined to form a ring;

wherein, when B is selected form Formula 2 or Formula 3, and all of Y are $CR_Y$, X is, at each occurrence identically or differently, selected from the group consisting of S, Se, NR' and CR"R'".

According to yet another embodiment of the present disclosure, an electroluminescent device is also disclosed, which comprises an anode, a cathode, and an organic layer disposed between the anode and the cathode, wherein the organic layer comprises a compound having a structure of $B(A)_2$, wherein A has a structure of Formula 1:

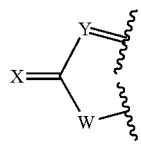

Formula 1 wherein,

X is, at each occurrence identically or differently, selected from the group consisting of O, S, Se, NR' and CR"R'";

Y is, at each occurrence identically or differently, selected from the group consisting of $CR_Y$ and N;

W is, at each occurrence identically or differently, selected from the group consisting of O, S, Se and $NR_N$;

wherein, B is selected from a substituted or unsubstituted conjugated unsaturated fused aryl ring having 10 to 30 ring atoms, or a substituted or unsubstituted conjugated unsaturated fused heteroaryl ring having 10 to 30 ring atoms, or selected from the structure represented by Formula 2 to Formula 8, or combinations thereof:

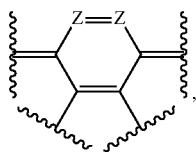

Formula 2

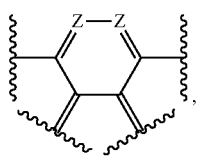

Formula 3

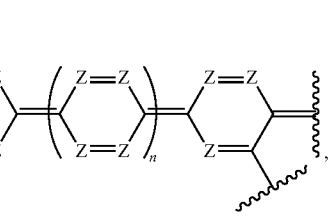

Formula 4

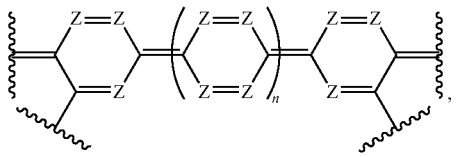

Formula 5

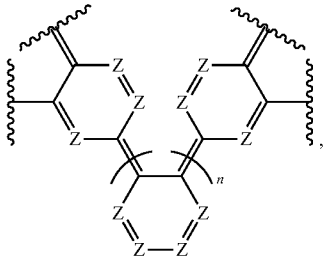

Formula 6

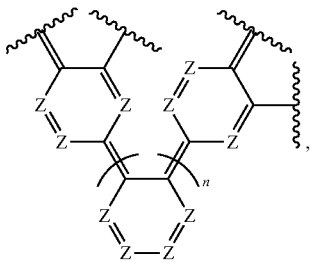

Formula 7

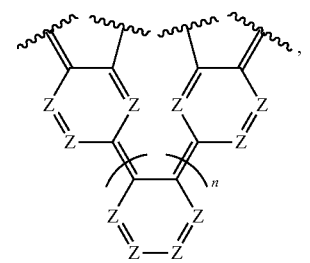

Formula 8 wherein B is fused with each of A through a single bond and a double bond;

wherein Z is, at each occurrence identically or differently, selected from the group consisting of CR and N; n is, at each occurrence identically or differently, selected from 0, 1, or 2;

wherein, R, R', R", R''', $R_N$ and $R_Y$ are, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, sulfanyl, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein at least one of R, R', R", R''', $R_N$ and $R_Y$ is a group having at least one electron-withdrawing group; and wherein any two adjacent substituents R, R', R", R''', $R_N$ and $R_Y$ can be optionally joined to form a ring;

wherein, when B is selected form Formula 2 or Formula 3, and all of Y are $CR_Y$, X is, at each occurrence identically or differently, selected from the group consisting of S, Se, NR' and CR"R'''.

According to another embodiment of the present disclosure, a compound formulation is also disclosed, which comprises the compound having the structure of $B(A)_2$.

The novel compounds having a structure of dehydro-fused-ring as disclosed in the present disclosure can be used as charge-transporting materials and charge injection materials in electroluminescent devices. Such novel compounds have very deep LUMO energy level, so they are excellent electron acceptor materials and charge transfer materials. They also have the potential to be excellent hole injection materials and p-dopant materials, and have broad industrial application prospects.

DETAILED DESCRIPTION

Figure 1:
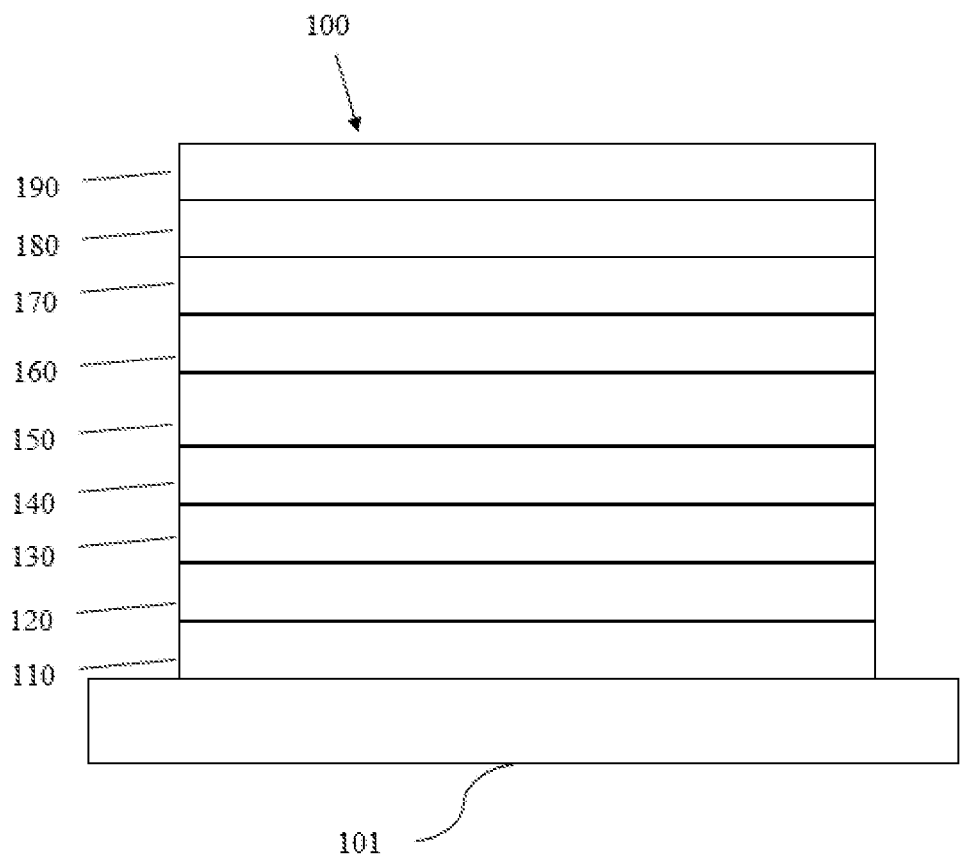
FIG. 1 schematically shows an organic light emitting device that can incorporate the compound and compound formulation disclosed herein.

OLEDs can be fabricated on various types of substrates such as glass, plastic, and metal foil. FIG. 1 schematically shows the organic light emitting device 100 without limitation. The figures are not necessarily drawn to scale. Some of the layer in the figure can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, which are incorporated by reference in its entirety.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F4-TCNQ at a molar ratio of 50:1, as disclosed in U.S. Patent Application Publication No. 2003/0230980, which is incorporated by reference in its entirety. Examples of host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

The layered structure described above is provided by way of non-limiting example. Functional OLEDs may be achieved by combining the various layers described in different ways, or layers may be omitted entirely, such as an electron blocking layer. It may also include other layers not specifically described. Within each layer, a single material or a mixture of multiple materials can be used to achieve optimum performance. Any functional layer may include several sublayers. For example, the emissive layer may have a two layers of different emitting materials to achieve desired emission spectrum.

In one embodiment, an OLED may be described as having an "organic layer" disposed between a cathode and an anode. This organic layer may comprise a single layer or multiple layers.

Figure 2:
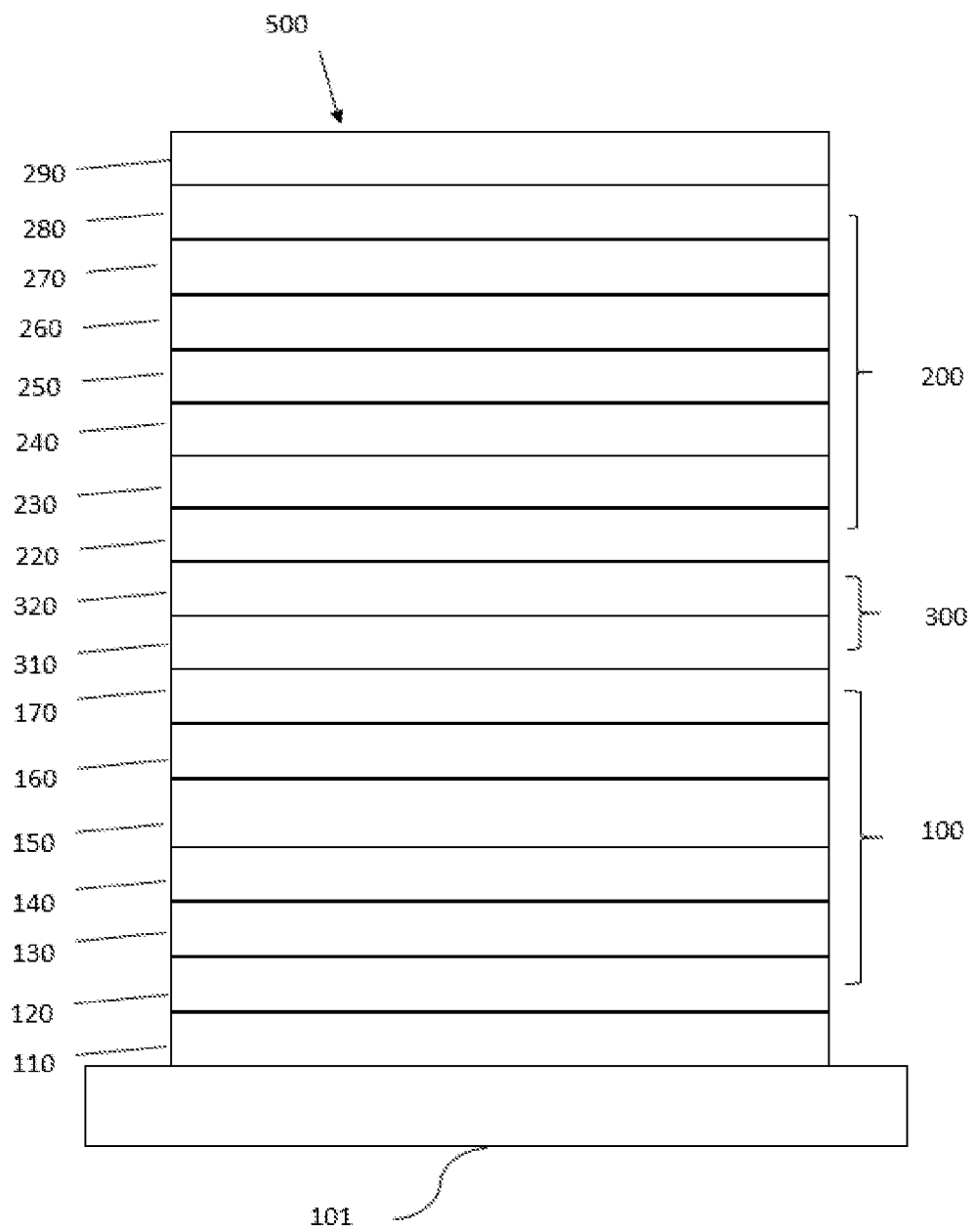
FIG. 2 schematically shows a tandem organic light emitting device that can incorporate the compound and compound formulation disclosed herein.

In one embodiment, two or more OLED units may be series connection to form a tandem OLED. FIG. 2 schematically shows the tandem organic light emitting device 500 without limitation. The device 500 may include a substrate 101, an anode 110, a first unit 100, a charge generation layer 300, a second unit 200, and a cathode 290. Wherein the first unit 100 includes a hole injection layer 120, a hole transporting layer 130, an electron blocking layer 140, an emissive layer 150, a hole blocking layer 160, an electron transporting layer 170, and the second unit 200 includes a hole injection layer 220, a hole transporting layer 230, an electron blocking layer 240, an emissive layer 250, a hole blocking layer 260, an electron transporting layer 270, and an electron injection layer 280. The charge generation layers 300 include an N type charge generation layer 310 and a P type charge generation layer 320. The device 500 may be manufactured by sequentially depositing the described layers.

Figure 3:
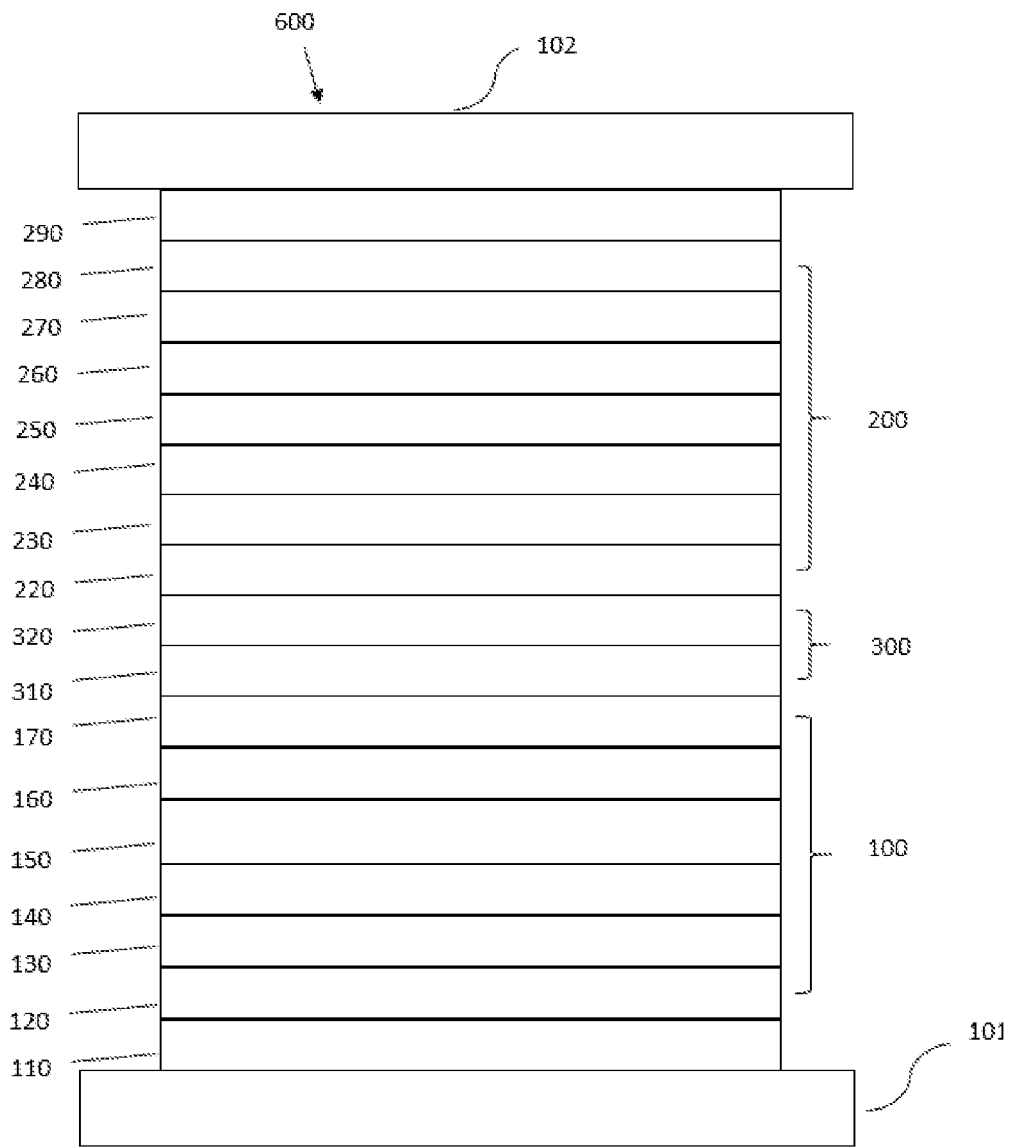
FIG. 3 schematically shows another tandem organic light emitting device that can incorporate the compound and compound formulation disclosed herein.

An OLED can be encapsulated by a barrier layer. FIG. 3 schematically shows the organic light emitting device 600 without limitation. FIG. 3 differs from FIG. 2 in that the organic light emitting device include a barrier layer 102, which is above the cathode 290, to protect it from harmful species from the environment such as moisture and oxygen. Any material that can provide the barrier function can be used as the barrier layer such as glass and organic-inorganic hybrid layers. The barrier layer should be placed directly or indirectly outside of the OLED device. Multilayer thin film encapsulation was described in U.S. Pat. No. 7,968,146, which is herein incorporated by reference in its entirety.

Devices fabricated in accordance with embodiments of the invention can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small $\Delta E_{S-T}$. These states may involve CT states. Often, donor-acceptor luminescent materials are constructed by connecting an electron donor moiety such as amino- or carbazole-derivatives and an electron acceptor moiety such as N-containing six-membered aromatic rings.

Definition of Terms of Substituents

Halogen or halide—as used herein includes fluorine, chlorine, bromine, and iodine.

Alkyl—contemplates both straight and branched chain alkyl groups. Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group. Additionally, the alkyl group may be optionally substituted. The carbons in the alkyl chain can be replaced by other hetero atoms. Of the above, preferred are methyl group, ethyl group, propyl group, isopropyl group, n-butyl group, s-butyl group, isobutyl group, t-butyl group, n-pentyl group, and neopentyl group.

Cycloalkyl—as used herein contemplates cyclic alkyl groups. Preferred cycloalkyl groups are those containing 4 to 10 ring carbon atoms and includes cyclobutyl, cyclopentyl, cyclohexyl, 4-methylcyclohexyl, 4,4-dimethylcylcohexyl, 1-adamantyl, 2-adamantyl, 1-norbornyl, 2-norbornyl and the like. Additionally, the cycloalkyl group may be optionally substituted. The carbons in the ring can be replaced by other hetero atoms.

Heteroalkyl—as used herein, heteroalkyl groups include the groups formed from one or more carbons in the alkyl chain substituted by heteroatoms selected from the group consisting of nitrogen atom, oxygen atom, sulfur atom, selenium atom, phosphorus atom, silicon atom, germanium atom, and boron atom. Heteroalkyl groups are those containing one to twenty carbon atoms, preferably one to ten carbon atoms, more preferably one to six carbon atoms. Examples of the heteroalkyl group include methoxymethyl, ethoxymethyl, ethoxyethyl, methylthiomethyl, ethylthiomethyl, ethylthioethyl, methoxymethoxymethyl, ethoxymethoxymethyl, ethoxyethoxy-ethyl, hydroxymethyl, hydroxyethyl, hydroxypropyl, sulfanylmethyl, sulfanylethyl, sulfanyl-propyl, aminomethyl, aminoethyl, aminopropyl, dimethylaminomethyl, trimethylgermanyl, dimethylethylgermanyl, dimethylisopropylgermanyl, tert-butyldimethylgermanyl, triethyl-germanyl, triisopropylgermanyl, trimethylsilylmethyl, trimethylsilylethyl, trimethylsilylisopropyl. Additionally, the heteroalkyl group may be optionally substituted.

Alkenyl—as used herein contemplates both straight and branched chain alkene groups. Preferred alkenyl groups are those containing two to fifteen carbon atoms. Examples of the alkenyl group include vinyl group, allyl group, 1-butenyl group, 2-butenyl group, 3-butenyl group, 1,3-butandienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl1-butenyl group, and 3-phenyl-1-butenyl group. Additionally, the alkenyl group may be optionally substituted.

Alkynyl—as used herein contemplates both straight and branched chain alkyne groups. Preferred alkynyl groups are those containing two to fifteen carbon atoms. Additionally, the alkynyl group may be optionally substituted.

Aryl or aromatic group—as used herein contemplates noncondensed and condensed systems. Preferred aryl groups are those containing six to sixty carbon atoms, preferably six to twenty carbon atoms, more preferably six to twelve carbon atoms. Examples of the aryl group include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Additionally, the aryl group may be optionally substituted. Examples of the non-condensed aryl group include phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl p-terphenyl-4-yl group, o-cumenyl group, m-cumenyl group, p-cumenyl group, 2,3-xylyl group, 3,4-xylyl group, 2,5-xylyl group, mesityl group, and m-quarterphenyl group.

Heterocyclic group or heterocycle—as used herein contemplates aromatic and non-aromatic cyclic groups. Heteroaromatic also means heteroaryl. Preferred non-aromatic heterocyclic groups are those containing 3 to 7 ring atoms which includes at least one hetero atom such as nitrogen, oxygen, and sulfur. The heterocyclic group can also be an aromatic heterocyclic group having at least one heteroatom selected from nitrogen atom, oxygen atom, sulfur atom, and selenium atom.

Heteroaryl—as used herein contemplates noncondensed and condensed hetero-aromatic groups that may include from one to five heteroatoms. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridoindole, pyrrolopyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenopheno-pyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—it is represented by —O-Alkyl. Examples and preferred examples thereof are the same as those described above. Examples of the alkoxy group having 1 to 20 carbon atoms, preferably 1 to 6 carbon atoms include methoxy group, ethoxy group, propoxy group, butoxy group, pentyloxy group, and hexyloxy group. The alkoxy group having 3 or more carbon atoms may be linear, cyclic or branched.

Aryloxy—it is represented by —O-Aryl or —O-heteroaryl. Examples and preferred examples thereof are the same as those described above. Examples of the aryloxy group having 6 to 40 carbon atoms include phenoxy group and biphenyloxy group.

Arylalkyl—as used herein contemplates an alkyl group that has an aryl substituent. Additionally, the arylalkyl group may be optionally substituted. Examples of the arylalkyl group include benzyl group, 1-phenylethyl group, 2-phenylethyl group, 1-phenylisopropyl group, 2-phenylisopropyl group, phenyl-t-butyl group, alpha.-naphthylmethyl group, 1-alpha.-naphthylethyl group, 2-alpha-naphthylethyl group, 1-alpha-naphthylisopropyl group, 2-alpha-naphthylisopropyl group, beta-naphthylmethyl group, 1-beta-naphthylethyl group, 2-beta-naphthylethyl group, 1-beta-naphthylisopropyl group, 2-beta-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro2-phenylisopropyl group. Of the above, preferred are benzyl group, p-cyanobenzyl group, m-cyanobenzyl group, o-cyanobenzyl group, 1-phenylethyl group, 2-phenylethyl group, 1-phenylisopropyl group, and 2-phenylisopropyl group.

The term "aza" in azadibenzofuran, aza-dibenzothiophene, etc. means that one or more of the C—H groups in the respective aromatic fragment are replaced by a nitrogen atom. For example, azatriphenylene encompasses dibenzo[f,h]quinoxaline,dibenzo[f,h]quinoline and other analogues with two or more nitrogens in the ring system. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In the compounds mentioned in this disclosure, the hydrogen atoms can be partially or fully replaced by deuterium. Other atoms such as carbon and nitrogen, can also be replaced by their other stable isotopes. The replacement by other stable isotopes in the compounds may be preferred due to its enhancements of device efficiency and stability.

In the compounds mentioned in this disclosure, multiple substitutions refer to a range that includes a double substitution, up to the maximum available substitutions. When a substitution in the compounds mentioned in this disclosure represents multiple substitutions (including di, tri, tetra substitutions etc.), that means the substituent can exist at a plurality of available substitution positions on its linking structure, the substituents present at a plurality of available substitution positions can be the same structure or different structures.

In the present disclosure, unless otherwise defined, when any term of the group consisting of substituted alkyl, substituted cycloalkyl, substituted heteroalkyl, substituted aralkyl, substituted alkoxy, substituted aryloxy, substituted alkenyl, substituted alkynyl, substituted aryl, substituted heteroaryl, substituted alkylsilyl, substituted arylsilyl, substituted amine, substituted acyl, substituted carbonyl, substituted carboxylic acid group, substituted ester group, substituted sulfinyl, substituted sulfonyl and substituted phosphoroso is used, it means that any group of alkyl, cycloalkyl, heteroalkyl, aralkyl, alkoxy, aryloxy, alkenyl, alkynyl, aryl, heteroaryl, alkylsilyl, arylsilyl, amine, acyl, carbonyl, carboxylic acid group, ester group, sulfinyl, sulfonyl and phosphoroso may be substituted with one or more groups selected from the group consisting of deuterium, a halogen, an unsubstituted alkyl group having 1 to 20 carbon atoms, an unsubstituted cycloalkyl group having 3 to 20 ring carbon atoms, an unsubstituted heteroalkyl group having 1 to 20 carbon atoms, an unsubstituted aralkyl group having 7 to 30 carbon atoms, an unsubstituted alkoxy group having 1 to 20 carbon atoms, an unsubstituted aryloxy group having 6 to 30 carbon atoms, an unsubstituted alkenyl group having 2 to 20 carbon atoms, an unsubstituted aryl group having 6 to 30 carbon atoms, an unsubstituted heteroaryl group having 3 to 30 carbon atoms, an unsubstituted alkylsilyl group having 3 to 20 carbon atoms, an unsubstituted arylsilyl group having 6 to 20 carbon atoms, an unsubstituted amino group having 0 to 20 carbon atoms, an acyl group, a carbonyl group, a carboxylic acid group, an ester group, a cyano group, an isocyano group, a sulfanyl group, a sulfinoyl group, a sulfonyl group and a phosphoroso group, and combinations thereof.

In the compounds mentioned in the present disclosure, adjacent substituents in the compounds cannot connect to form a ring unless otherwise explicitly defined, for example, adjacent substituents can be optionally joined to form a ring. In the compounds mentioned in the present disclosure, adjacent substituents can be optionally joined to form a ring, including both the case where adjacent substituents can be joined to form a ring, and the case where adjacent substituents are not joined to form a ring. When adjacent substituents can be optionally joined to form a ring, the ring formed may be monocyclic or polycyclic, as well as alicyclic, heteroalicyclic, aromatic or heteroaromatic. In such expression, adjacent substituents may refer to substituents bonded to the same atom, substituents bonded to carbon atoms which are directly bonded to each other, or substituents bonded to carbon atoms which are more distant from each other. Preferably, adjacent substituents refer to substituents bonded to the same carbon atom and substituents bonded to carbon atoms which are directly bonded to each other.

The expression that adjacent substituents can be optionally joined to form a ring is also intended to mean that two substituents bonded to the same carbon atom are joined to each other via a chemical bond to form a ring, which can be exemplified by the following formula:

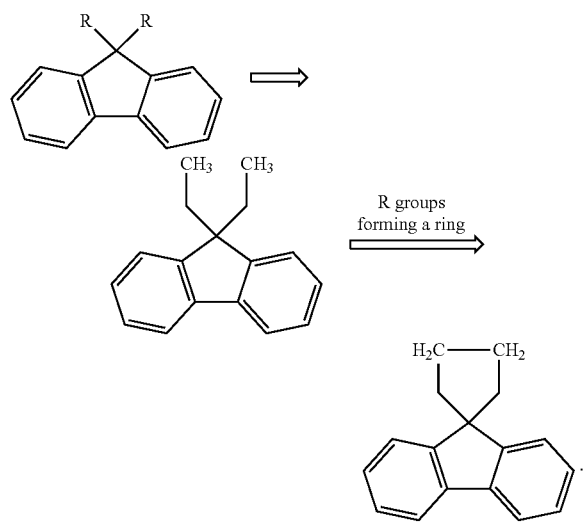

The expression that adjacent substituents can be optionally joined to form a ring is also intended to mean that two substituents bonded to carbon atoms which are directly bonded to each other are joined to each other via a chemical bond to form a ring, which can be exemplified by the following formula:

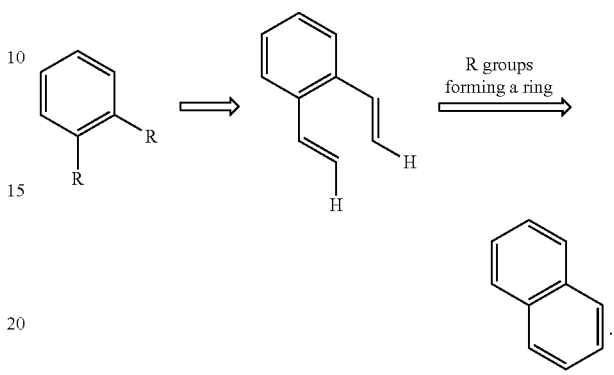

Furthermore, the expression that adjacent substituents can be optionally joined to form a ring is also intended to mean that, in the case where one of the two substituents bonded to carbon atoms which are directly bonded to each other represents hydrogen, the second substituent is bonded at a position at which the hydrogen atom is bonded, thereby forming a ring. This is exemplified by the following formula:

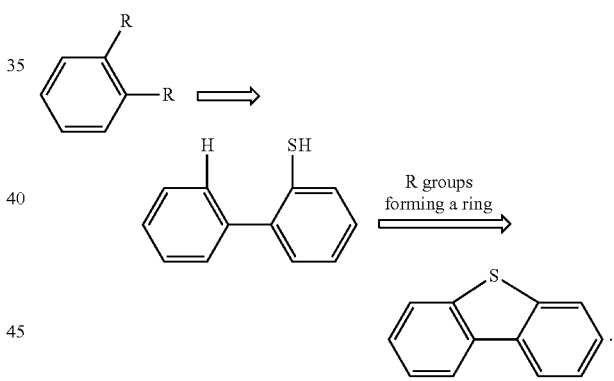

According to an embodiment of the present disclosure, a compound having a structure of $B(A)_2$ is disclosed, wherein A has a structure of Formula 1:

Formula 1 wherein,
X is, at each occurrence identically or differently, selected from the group consisting of O, S, Se, NR' and CR"R'";
Y is, at each occurrence identically or differently, selected from the group consisting of $CR_Y$ and N;
W is, at each occurrence identically or differently, selected from the group consisting of O, S, Se and $NR_N$;

wherein, B is selected from a substituted or unsubstituted conjugated unsaturated fused aryl ring having 10 to 30 ring atoms, or a substituted or unsubstituted conjugated unsaturated fused heteroaryl ring having 10 to 30 ring atoms, or the structure represented by Formula 2 to Formula 8, or the combination thereof:

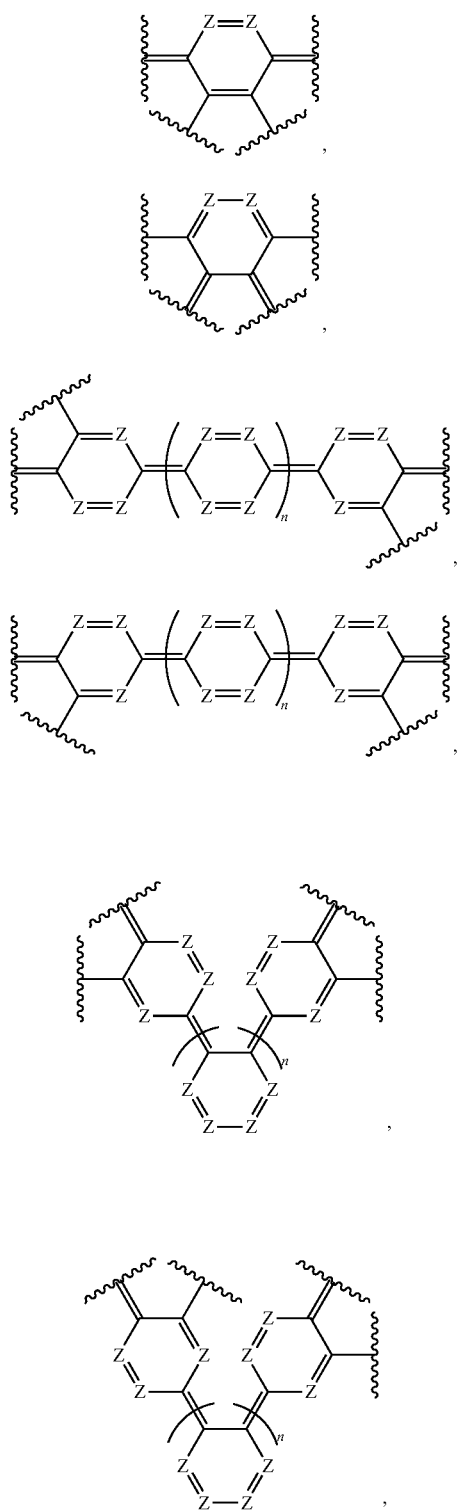

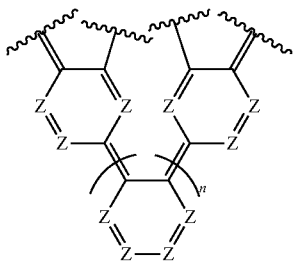

Formula 8 wherein B is fused with every A through a single bond and a double bond;

wherein Z is, at each occurrence identically or differently, selected from the group consisting of CR and N; n is, at each occurrence identically or differently, selected from 0, 1, or 2;

wherein, R, R', R", R''', $R_N$ and $R_Y$ are, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, sulfanyl, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein at least one of R, R', R", R', $R_N$ and $R_Y$ is a group having at least one electron-withdrawing group; and any two adjacent substituents R, R', R", R''', $R_N$ and $R_Y$ can be optionally joined to form a ring;

wherein, when B is selected form Formula 2 or Formula 3, and all of Y are $CR_Y$, X is, at each occurrence identically or differently, selected from the group consisting of S, Se, NR' and CR"R'''.

In the present disclosure, the expression that any two adjacent substituents R, R', R", R''', $R_N$ and $R_Y$ can be optionally joined to form a ring is intended to mean that any two adjacent substituents of R, R', R", R''', $R_N$ and $R_Y$, for example, between two R, between R and R', between R and R", between R' and R", between R and R''', between R" and $R_Y$, between R''' and $R_Y$, between R" and R''', between R" and $R_N$, between R''' and $R_N$, between R and $R_Y$, between R' and $R_Y$, and between R and $R_N$, any one or more of them may be optionally joined to form a ring. Obviously, any adjacent R, R', R", R''', $R_N$ and $R_Y$ substituents may not be joined to form a ring.

In the present disclosure, B is selected from a conjugated unsaturated fused aryl ring having 10 to 30 ring atoms, or a conjugated unsaturated fused heteroaryl ring having 10 to 30 ring atoms, wherein the conjugated unsaturated fused aryl ring or the conjugated unsaturated fused heteroaryl ring is intended to mean that B other than the part fused with Formula 1 has the structure of conjugated unsaturated fused aryl ring or heteroaryl ring, for example, B may be selected form the structure of

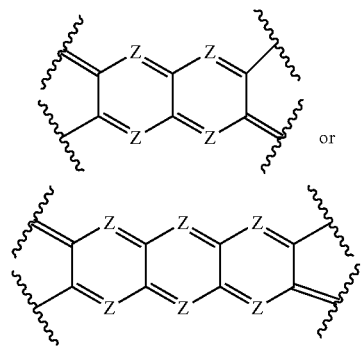

or (wherein Z is as defined in the embodiments above); obviously, when B is selected from Formula 4 to 8, the other part of it other than the part fused with Formula 1 are all conjugated unsaturated single ring structures and are not fused structures, therefore they do not belong to the substituted or unsubstituted conjugated unsaturated fused aryl ring having 10 to 30 ring atoms, or the substituted or unsubstituted conjugated unsaturated fused heteroaryl ring having 10 to 30 ring atoms.

According to an embodiment of the present disclosure, wherein when B is selected from Formula 2 or Formula 3, the compound is selected from the structure of Formula I or Formula II:

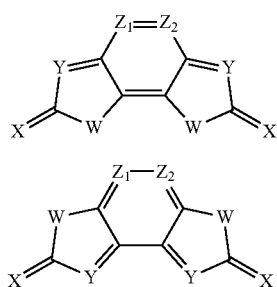

Formula I

Formula II wherein,

X is, at each occurrence identically or differently, selected from the group consisting of O, S, Se, NR' and CR"R'";

Y is, at each occurrence identically or differently, selected from the group consisting of $CR_Y$ and N; and when Y is $CR_Y$, X is, at each occurrence identically or differently, selected from the group consisting of S, Se, NR' and CR"R'";

W is, at each occurrence identically or differently, selected from the group consisting of O, S, Se and $NR_N$;

wherein $Z_1$ and $Z_2$ are, at each occurrence identically or differently, selected from the group consisting of CR and N;

wherein, R, R', R", R'", $R_N$ and $R_Y$ are, at each occurrence identically or differently, selected from the group consisting of hydrogen, deuterium, halogen, nitroso, nitro, acyl, carbonyl, a carboxylic acid group, an ester group, cyano, isocyano, SCN, OCN, SF$_5$, boranyl, sulfinyl, sulfonyl, phosphoroso, sulfanyl, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein at least one of R, R', R", R'", $R_N$ and $R_Y$ is a group having at least one electron-withdrawing group; and wherein any two adjacent substituents R, R', R", R'", $R_N$ and $R_Y$ can be optionally joined to forma ring.

According to an embodiment of the present disclosure, wherein when B is selected from a substituted or unsubstituted conjugated unsaturated fused aryl ring having 10 to 30 ring atoms, or a substituted or unsubstituted conjugated unsaturated fused heteroaryl ring having 10 to 30 ring atoms, the compound is selected from the structure of any one of Formula III to Formula XVIII:

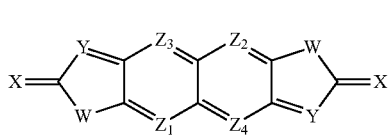

Formula III

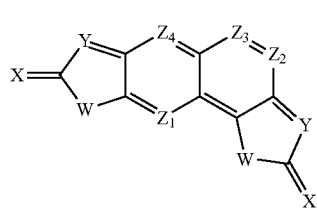

Formula IV

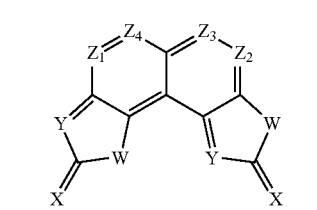

Formula V

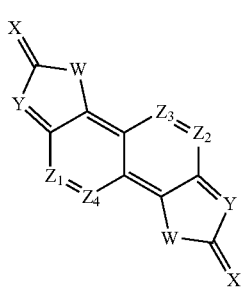

Formula VI

Formula VII
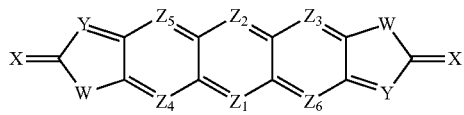

Formula VIII
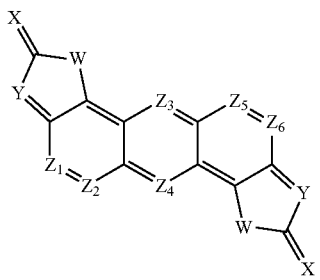

Formula IX
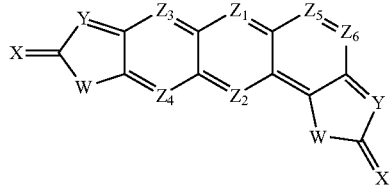

Formula X
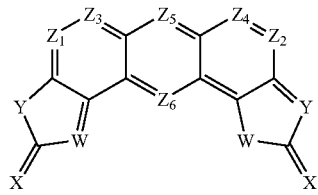

Formula XI
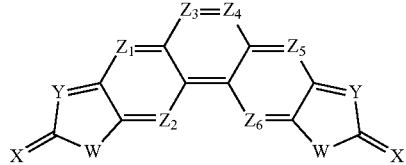

Formula XII
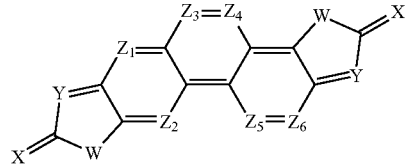

Formula XIII
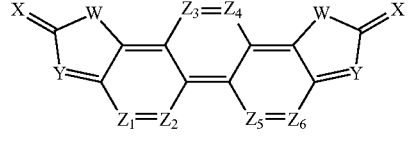

Formula XIV
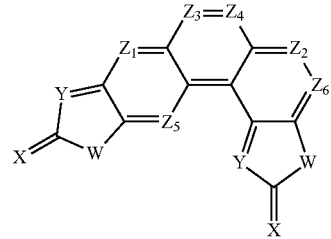

Formula XV
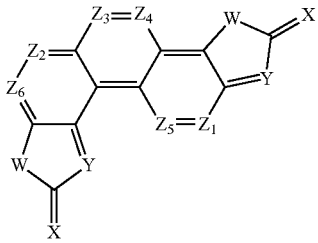

Formula XVI
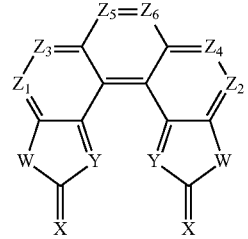

Formula XVII
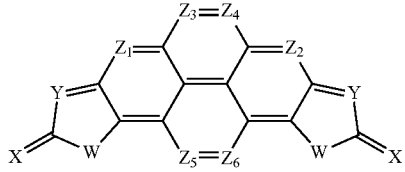

Formula XVIII
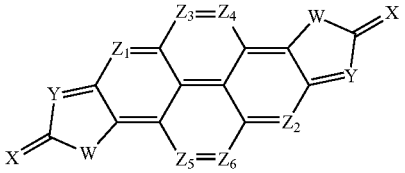

wherein,

X is, at each occurrence identically or differently, selected from the group consisting of O, S, Se, NR' and CR"R'";

Y is, at each occurrence identically or differently, selected from the group consisting of $CR_Y$ and N; wherein, when the compound is selected from Formula III, VI or VII, all of Y are N;

W is, at each occurrence identically or differently, selected from the group consisting of O, S, Se and $NR_N$;

wherein $Z_1$ to $Z_6$ are, at each occurrence identically or differently, selected from the group consisting of CR and N;

wherein, R, R', R", R'", $R_N$ and $R_Y$ are, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, sulfanyl, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein at least one of R, R', R", R''', $R_N$ and $R_Y$ is a group having at least one electron-withdrawing group; and wherein any two adjacent substituents R, R', R", R''', $R_N$ and $R_Y$ can be optionally joined to form a ring.

According to an embodiment of the present disclosure, wherein, in the Formula III, Formula IV, Formula V, Formula VI, or Formula VII, Y is N.

According to an embodiment of the present disclosure, wherein when B is selected from Formula 4 to Formula 8, n is 0 or 1, and the compound has the structure of any one of Formula XIX to Formula XXIV:

Formula XIX
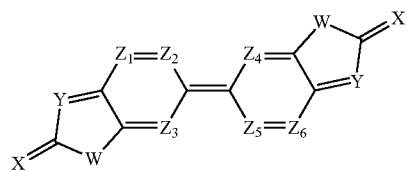

Formula XX
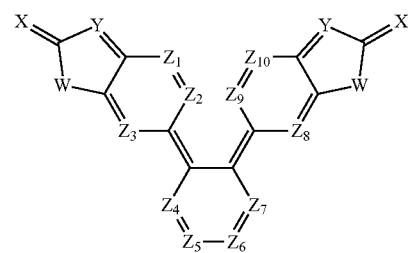

Formula XXI
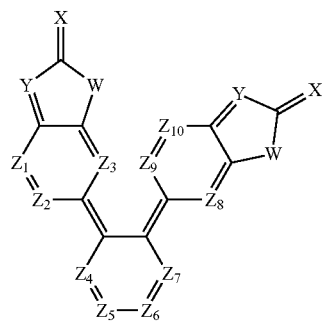

Formula XXII
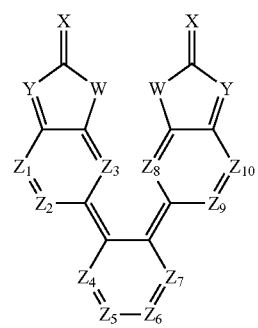

Formula XXIII
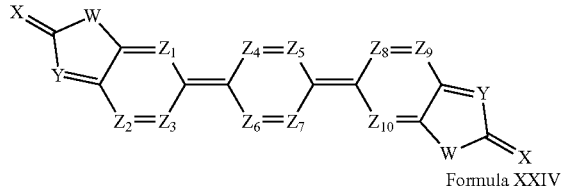

Formula XXIV
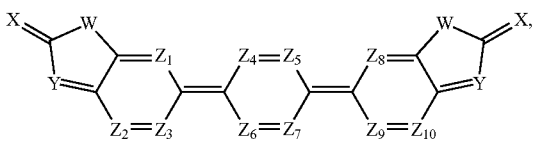

wherein,

X is, at each occurrence identically or differently, selected from the group consisting of O, S, Se, NR' and CR"R''';

Y is, at each occurrence identically or differently, selected from the group consisting of $CR_Y$ and N;

W is, at each occurrence identically or differently, selected from the group consisting of O, S, Se and $NR_N$;

wherein $Z_1$ to $Z_{10}$ are, at each occurrence identically or differently, selected from the group consisting of CR and N;

wherein, R, R', R", R''', $R_N$ and $R_Y$ are, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, sulfanyl, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein at least one of R, R', R", R''', $R_N$ and $R_Y$ is a group having at least one electron-withdrawing group; and wherein any two adjacent substituents R, R', R", R''', $R_N$ and $R_Y$ can be optionally joined to forma ring.

According to an embodiment of the present disclosure, wherein X is, at each occurrence identically or differently, selected from S, Se, NR' or CR"R'''.

According to an embodiment of the present disclosure, wherein X is, at each occurrence identically or differently, selected from CR"R'''.

According to an embodiment of the present disclosure, wherein W is, at each occurrence identically or differently, selected from 0, S or Se.

According to an embodiment of the present disclosure, wherein W is, at each occurrence identically or differently, selected from O or S.

According to an embodiment of the present disclosure, wherein W is selected from O.

According to an embodiment of the present disclosure, wherein in the compounds, all of Y are N.

According to an embodiment of the present disclosure, wherein, when B is selected from a substituted or unsubstituted conjugated unsaturated fused aryl ring having 10 to 30 ring atoms, or a substituted or unsubstituted conjugated unsaturated fused heteroaryl ring having 10 to 30 ring atoms, all of Y are N.

According to an embodiment of the present disclosure, wherein W is, at each occurrence identically or differently, selected from $NR_N$, $R_N$ is, at each occurrence identically or differently, selected from the group consisting of a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof.

According to an embodiment of the present disclosure, wherein W is, at each occurrence identically or differently, selected from $NR_N$, $R_N$ is, at each occurrence identically or differently, selected from the group consisting of a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 carbon atoms, a substituted or unsubstituted heteroaryl group having 3 to 30 carbon atoms, and combinations thereof.

According to an embodiment of the present disclosure, wherein in the compounds, at least one of Z is selected from N.

According to an embodiment of the present disclosure, wherein in the Formula I to Formula XXIV, at least one of $Z_1$ to $Z_x$ is selected from N, the x of $Z_x$ corresponds to the largest number of Z existing in Formula I to Formula XXIV.

In the present embodiment, the x of $Z_x$ corresponds to the largest number of Z existing in Formula I to Formula XXIV, for example, for Formula V

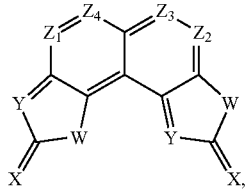

Formula V the largest number of Z existing is 4, the x in $Z_x$ is 4, therefore, in Formula V, at least one of $Z_1$ to $Z_4$ is selected from N. It is the same in the other formulas.

According to an embodiment of the present disclosure, in the compound, Z is, at each occurrence identically or differently, selected from CR, wherein R is, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, sulfanyl, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof.

According to an embodiment of the present disclosure, in the compound, Z is, at each occurrence identically or differently, selected from CR, wherein R is, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, sulfanyl, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof, and wherein at least one of R is selected from the group having at least one electron-withdrawing group.

According to an embodiment of the present disclosure, in the compound, Z is, at each occurrence identically or differently, selected from CR, wherein R is, at each occurrence identically or differently, selected from the group consisting of halogen, nitroso, nitro, acyl, carbonyl, a carboxylic acid group, an ester group, cyano, isocyano, SCN, OCN, $SF_5$, boranyl, sulfinyl, sulfonyl, phosphoroso, sulfanyl, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof, and R is, at each occurrence identically or differently, selected from the group having at least one electron-withdrawing group.

According to an embodiment of the present disclosure, wherein in the Formula I to Formula XXIV, $Z_1$ to $Z_{10}$ are, at each occurrence identically or differently, selected from CR.

According to an embodiment of the present disclosure, wherein in the Formula I to Formula XXIV, $Z_1$ to $Z_{10}$ are, at each occurrence identically or differently, selected from CR, wherein at least one R is selected from the group having at least one electron-withdrawing group.

According to an embodiment of the present disclosure, wherein in the Formula I to Formula XXIV, $Z_1$ to $Z_{10}$ are, at each occurrence identically or differently, selected from CR, wherein R is, at each occurrence identically or differently, selected from the group having at least one electron-withdrawing group.

According to an embodiment of the present disclosure, X is, at each occurrence identically or differently, selected from NR' or CR"R'", wherein R', R" and R'" are groups having at least one electron-withdrawing group.

According to an embodiment of the present disclosure, X is, at each occurrence identically or differently, selected from CR"R'".

According to an embodiment of the present disclosure, in the compound, at least one of R, R', R" and R'" is the group having at least one electron-withdrawing group.

According to an embodiment of the present disclosure, in the compound, each of R, R', R" and R'" is the group having at least one electron-withdrawing group.

According to an embodiment of the present disclosure, in the compound, each of R, R', R", R'", $R_N$ and $R_Y$ is the group having at least one electron-withdrawing group.

According to an embodiment of the present disclosure, the Hammett's constant of the electron-withdrawing group is ≥0.05, or the Hammett's constant of the electron-withdrawing group is ≥0.3, or the Hammett's constant of the electron-withdrawing group is ≥0.5.

The electron-withdrawing group of the present disclosure has a Hammett's substituent constant value of ≥0.05, preferably ≥0.3, more preferably ≥0.5, and thus has a strong electron-withdrawing ability, which can significantly reduce the LUMO energy level of the compound and improve charge mobility.

It should be noted that the Hammett's substituent constant value includes Hammett's substituent para-position constant and/or meta-position constant. As long as one of the para-constant and the meta-constant is equal to or greater than 0.05, the group is preferred for the present disclosure.

According to an embodiment of the present disclosure, the electron-withdrawing group is selected from the group consisting of halogen, nitroso, nitro, acyl, carbonyl, a carboxylic acid group, an ester group, cyano, isocyano, SCN, OCN, $SF_5$, boranyl, sulfinyl, sulfonyl, phosphoroso, an aza-aromatic ring group, and any one of an alkyl group having 1 to 20 carbon atoms, a cycloalkyl group having 3 to 20 ring carbon atoms, a heteroalkyl group having 1 to 20 carbon atoms, an arylalkyl group having 7 to 30 carbon atoms, an alkoxy group having 1 to 20 carbon atoms, an aryloxy group having 6 to 30 carbon atoms, an alkenyl group having 2 to 20 carbon atoms, an alkynyl group having 2 to 20 carbon atoms, an aryl group having 6 to 30 carbon atoms, a heteroaryl group having 3 to 30 carbon atoms, an alkylsilyl group having 3 to 20 carbon atoms, and an arylsilyl group having 6 to 20 carbon atoms, which is substituted with one or more of halogen, nitroso, nitro, acyl, carbonyl, a carboxylic acid group, an ester group, cyano, isocyano, SCN, OCN, $SF_5$, boranyl, sulfinyl, sulfonyl, phosphoroso, an aza-aromatic ring group, and combinations thereof.

According to an embodiment of the present disclosure, the electron-withdrawing group is selected from the group consisting of F, $CF_3$, $OCF_3$, $SF_5$, $SO_2CF_3$, cyano, isocyano, SCN, OCN, pyrimidinyl, triazinyl, and combinations thereof.

According to an embodiment of the present disclosure, X is, at each occurrence identically or differently, selected from the group consisting of the following structures:

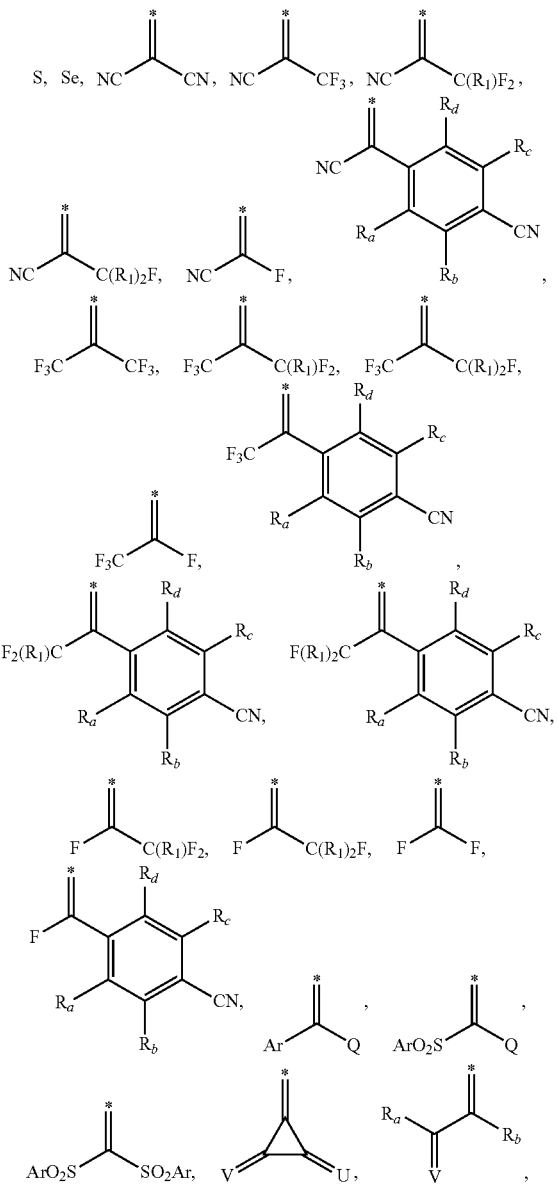

-continued

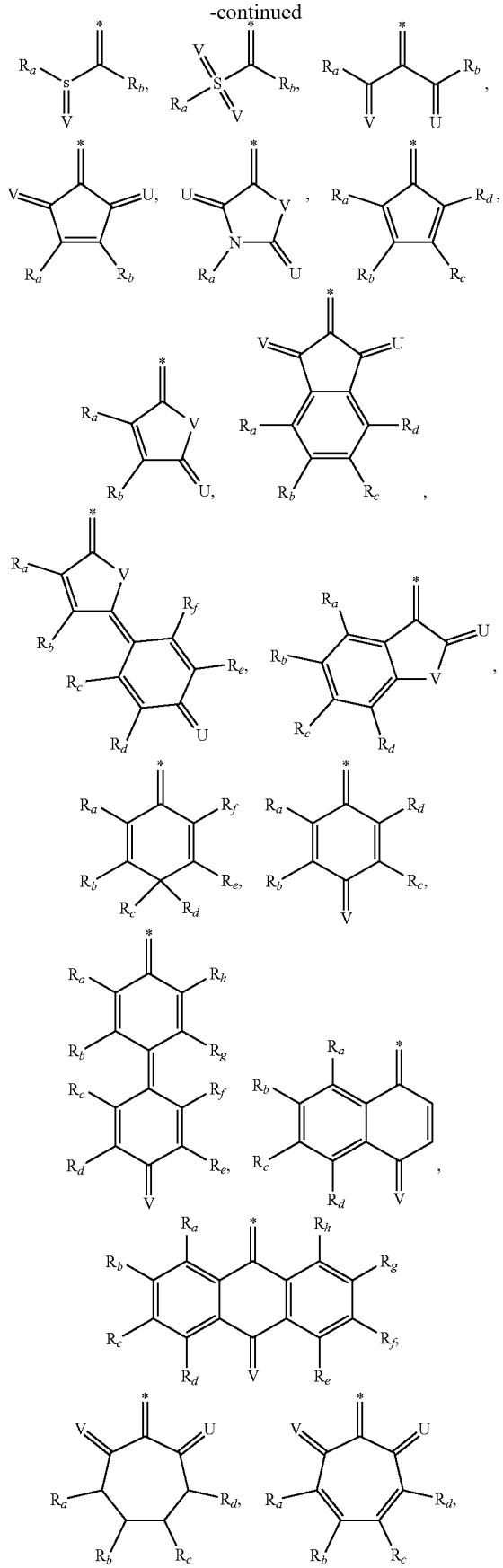

-continued

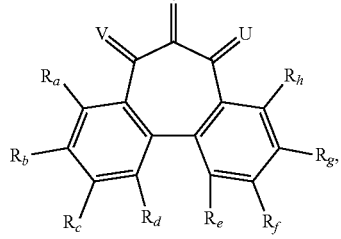

wherein $R_1$ is selected, at each occurrence, identically or differently, from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

preferably $R_1$ is selected, at each occurrence, identically or differently, from the group consisting of F, $CF_3$, $OCF_3$, $SF_5$, $SO_2CF_3$, cyano, isocyano, SCN, OCN, pentafluorophenyl, 4-cyanotetrafluorophenyl, tetrafluoropyridyl, pyrimidinyl, triazinyl, and combinations thereof;

wherein V and U are selected, at each occurrence, identically or differently, from the group consisting of $CR_vR_u$, $NR_v$, O, S and Se;

wherein Ar is selected, at each occurrence, identically or differently, from a substituted or unsubstituted aryl group having 6 to 30 carbon atoms, or a substituted or unsubstituted heteroaryl group having 3 to 30 carbon atoms;

wherein Q, $R_a$, $R_b$, $R_c$, $R_d$, $R_e$, $R_f$, $R_g$, $R_h$, $R_v$ and $R_u$ are selected, at each occurrence, identically or differently, from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein Q is a group having at least one electron-withdrawing group, and for any one of the structures, when one or more of $R_a$, $R_b$, $R_c$, $R_d$, $R_e$, $R_f$, $R_g$, $R_h$, $R_v$ and $R_u$ is(are) present, at least one of them is a group having at least one electron-withdrawing group, preferably, the group having at least one an electron-withdrawing group is selected from the group consisting of F, $CF_3$, $OCF_3$, $SF_5$, $SO_2CF_3$, cyano, isocyano, SCN, OCN, pentafluorophenyl, 4-cyanotetrafluorophenyl, tetrafluoropyridyl, pyrimidinyl, triazinyl, and combinations thereof.

In the present embodiment, "*" indicates the position at which the X groups are attached in formulas above.

According to an embodiment of the present disclosure, wherein X is, at each occurrence identically or differently, selected from the group consisting of:

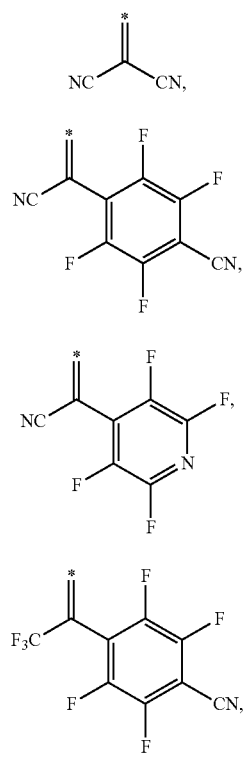

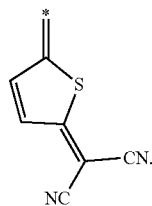

According to an embodiment of the present disclosure, wherein X is selected from A1.

According to an embodiment of the present disclosure, wherein R is, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, an unsubstituted alkyl group having 1 to 20 carbon atoms, an unsubstituted cycloalkyl group having 3 to 20 ring carbon atoms, an unsubstituted alkoxy group having 1 to 20 carbon atoms, an unsubstituted alkenyl group having 2 to 20 carbon atoms, an unsubstituted aryl group having 6 to 30 carbon atoms, an unsubstituted heteroaryl group having 3 to 30 carbon atoms, and any one of an alkyl group having 1 to 20 carbon atoms, a cycloalkyl group having 3 to 20 ring carbon atoms, an alkoxyl group having 1 to 20 carbon atoms, an alkenyl group having 2 to 20 carbon atoms, an aryl group having 6 to 30 carbon atoms, and a heteroaryl group having 3 to 30 carbon atoms which are substituted with one or more groups selected from the group consisting of halogen, nitroso, nitro, acyl, carbonyl, a carboxylic acid group, an ester group, cyano, isocyano, SCN, OCN, $SF_5$, boranyl, sulfinyl, sulfonyl, phosphoroso, and combinations thereof.

According to an embodiment of the present disclosure, wherein R is, at each occurrence identically or differently, selected from the group consisting of hydrogen, deuterium, methyl, isopropyl, $NO_2$, $SO_2CH_3$, $SCF_3$, $C_2F_5$, $OC_2F_5$, $OCH_3$, p-methylphenyl, diphenylmethylsilyl, phenyl, methoxyphenyl, 2,6-diisopropylphenyl, biphenyl, polyfluorophenyl, difluoropyridyl, nitrophenyl, dimethylthiazolyl, CN, vinyl substituted with one or more of CN and $CF_3$, ethynyl substituted with one of CN and $CF_3$, dimethylphosphoroso, diphenylphosphoroso, F, $CF_3$, $OCF_3$, $SF_5$, $SO_2CF_3$, cyano, isocyano, SCN, OCN, trifluoromethylphenyl, trifluoromethoxyphenyl, bis(trifluoromethyl)phenyl, bis(trifluoromethoxy)phenyl, 4-cyanotetrafluorophenyl, phenyl or biphenyl substituted with one or more of F, CN and $CF_3$, tetrafluoropyridyl, pyrimidinyl, triazinyl, diphenylboranyl, oxaboraanthryl, and combinations thereof.

According to an embodiment of the present disclosure, wherein R is, at each occurrence identically or differently, selected from the group consisting of:

-continued
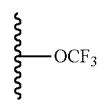 B3
 B4
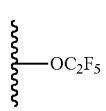 B5
 B6
 B7
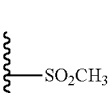 B8
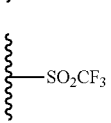 B9
 B10
 B11
 B12
 B13
 B14
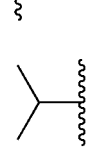 B15
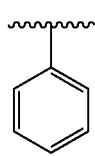 B16
-continued
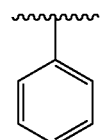 B17
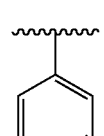 B18
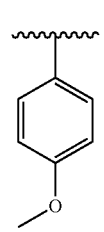 B19
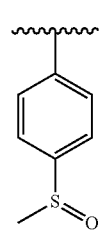 B20
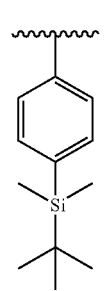 B21
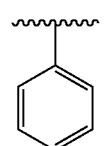 B22
 B23
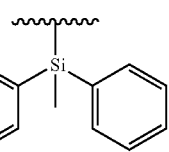 B24

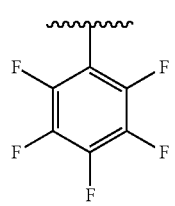 B25
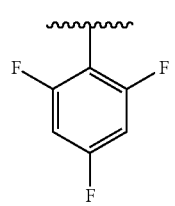 B26
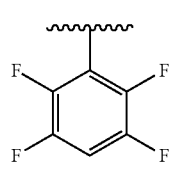 B27
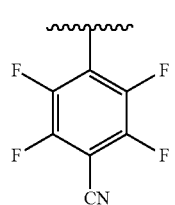 B28
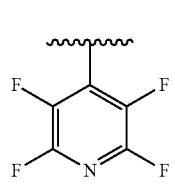 B29
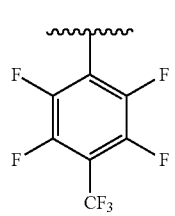 B30
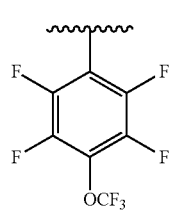 B31
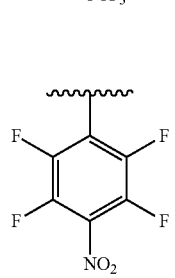 B32
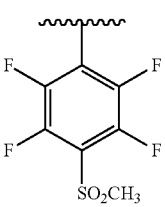 B33
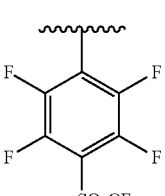 B34
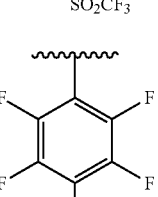 B35
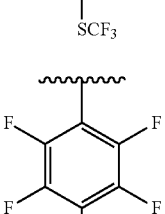 B36
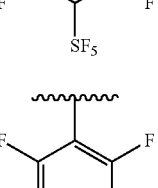 B37
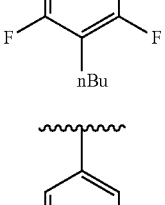 B38
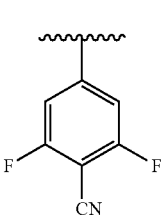 B39
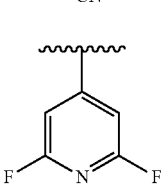 B40

-continued
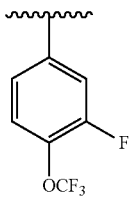 B41
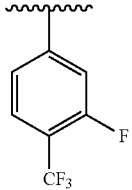 B42
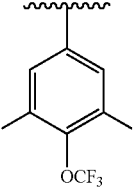 B43
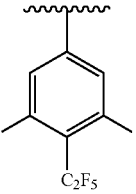 B44
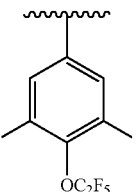 B45
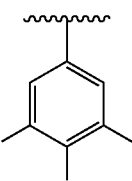 B46
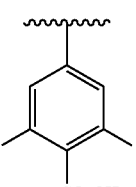 B47
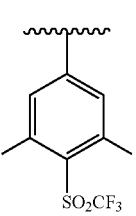 B48
-continued
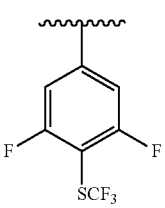 B49
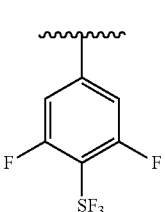 B50
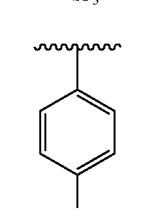 B51
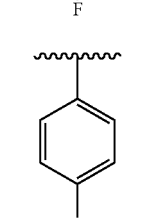 B52
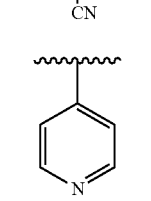 B53
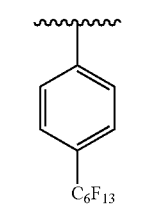 B54
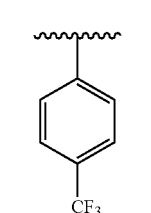 B55
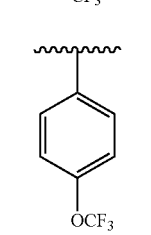 B56

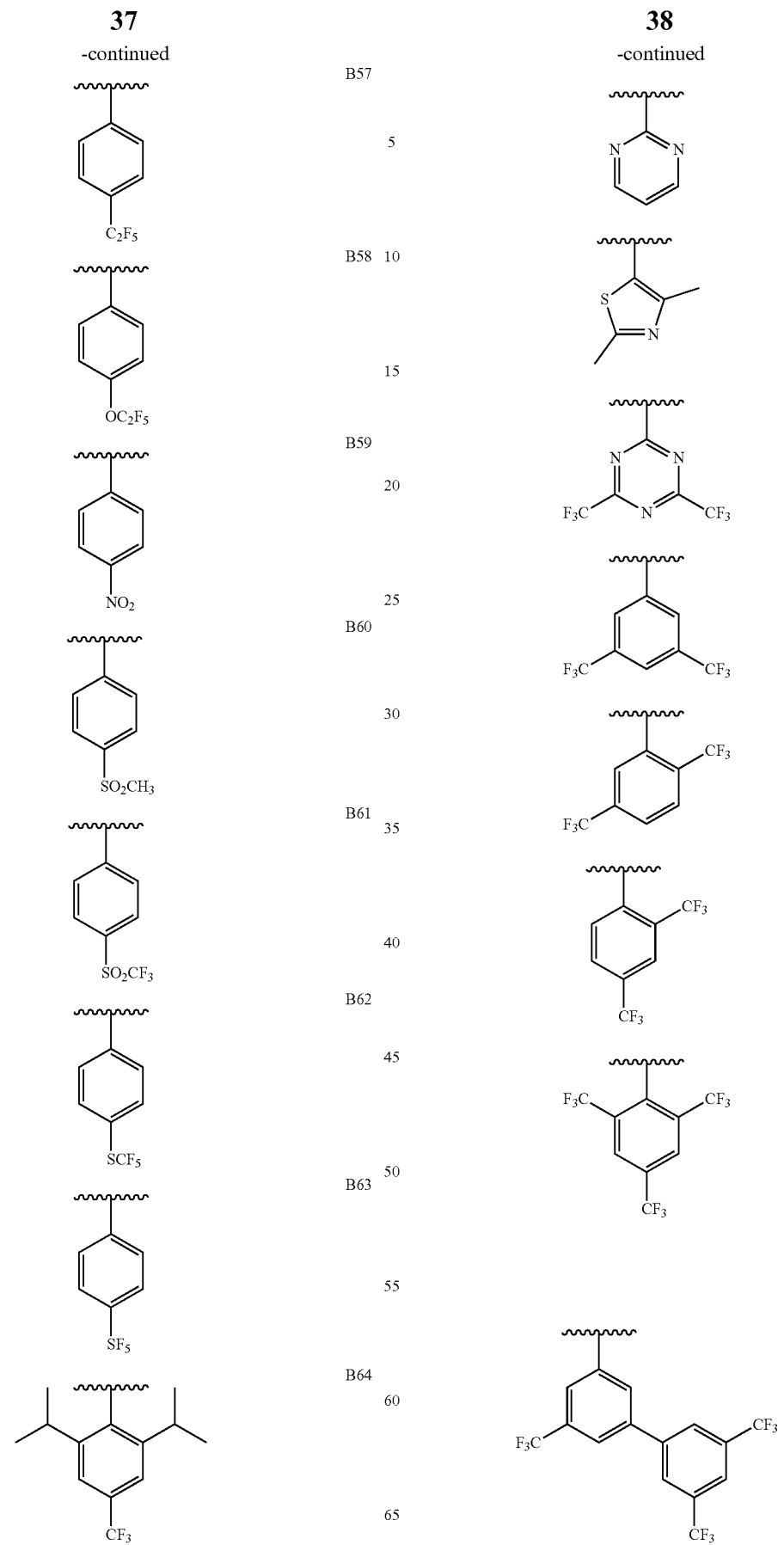

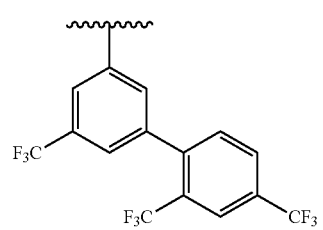
B73
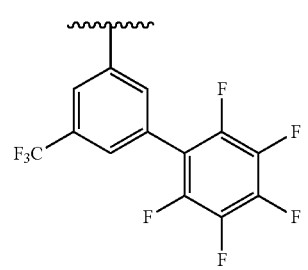
B74
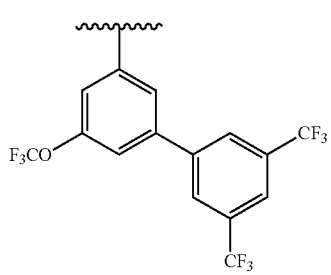
B75
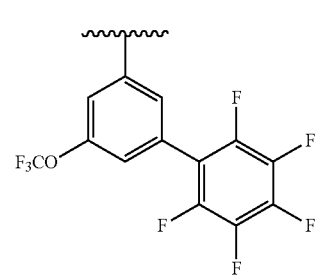
B76
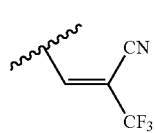
B77
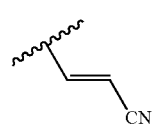
B78
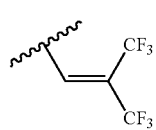
B79
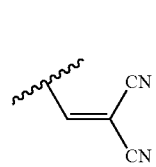
B80
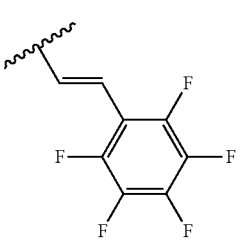
B81
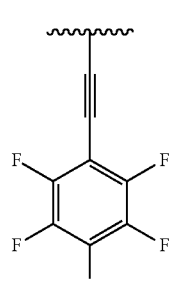
B82
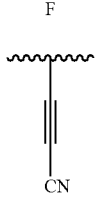
B83
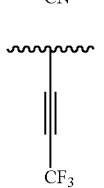
B84
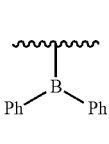
B85
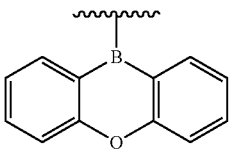
B86
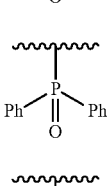
B87
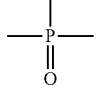
B88
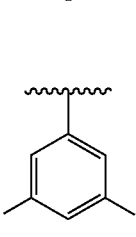
B89

-continued

B90, B91, B92, B93, B94, B95, B96, B97

-continued

B98, B99, B100, B101, B102, B103, B104, B105, B106

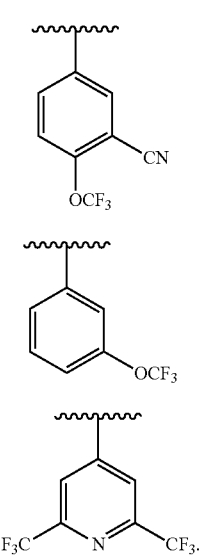

B107

B108

B109

According to an embodiment of the present disclosure, the compound is selected from the group consisting of Compound I-1 to Compound I-128, Compound II-1 to Compound II-128, Compound III-1 to Compound III-64, Compound IV-1 to Compound IV-128, Compound V-1 to Compound V-128, Compound VI-1 to Compound VI-64, Compound VII-1 to Compound VII-64, Compound VIII-1 to Compound VIII-128, Compound IX-1 to Compound IX-128, Compound X-1 to Compound X-128, Compound XI-1 to Compound XI-128, Compound XII-1 to Compound XII-128, Compound XIII-1 to Compound XIII-128, Compound XIV-1 to Compound XIV-128, Compound XV-1 to Compound XV-128, Compound XVI-1 to Compound XVI-128, Compound XVII-1 to Compound XVII-128, Compound XVIII-1 to Compound XVIII-128, Compound XIX-1 to Compound XIX-128;

Wherein the specific structure of Compound I-1 to Compound I-128, Compound II-1 to Compound II-128, Compound III-1 to Compound III-64, Compound IV-1 to Compound IV-128, Compound V-1 to Compound V-128, Compound VI-1 to Compound VI-64, Compound VII-1 to Compound VII-64, Compound VIII-1 to Compound VIII-128, Compound IX-1 to Compound IX-128, Compound X-1 to Compound X-128, Compound XI-1 to Compound XI-128, Compound XII-1 to Compound XII-128, Compound XIII-1 to Compound XIII-128, Compound XIV-1 to Compound XIV-128, Compound XV-1 to Compound XV-128, Compound XVI-1 to Compound XVI-128, Compound XVII-1 to Compound XVII-128, Compound XVIII-1 to Compound XVIII-128, Compound XIX-1 to Compound XIX-128 is set forth in claim 18.

According to an embodiment of the present disclosure, an electroluminescent device is also disclosed, which comprises:

an anode, a cathode, and an organic layer disposed between the anode and the cathode, wherein the organic layer comprises a compound having a structure of $B(A)_2$ is disclosed, wherein A has a structure of Formula 1:

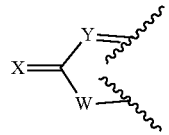

Formula 1 wherein,

X is, at each occurrence identically or differently, selected from the group consisting of O, S, Se, NR' and CR"R'";

Y is, at each occurrence identically or differently, selected from the group consisting of $CR_Y$ and N;

W is, at each occurrence identically or differently, selected from the group consisting of O, S, Se and $NR_N$;

wherein, B is selected from a substituted or unsubstituted conjugated unsaturated fused aryl ring having 10 to 30 ring atoms, or a substituted or unsubstituted conjugated unsaturated fused heteroaryl ring having 10 to 30 ring atoms, or the structure represented by Formula 2 to Formula 8, or the combination thereof:

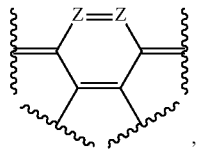

Formula 2

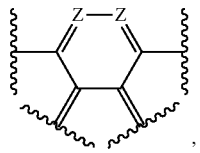

Formula 3

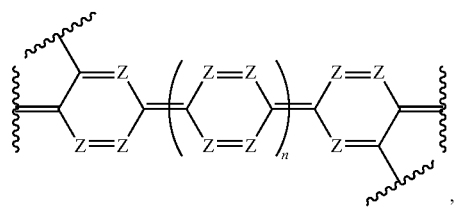

Formula 4

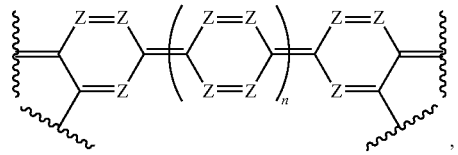

Formula 5

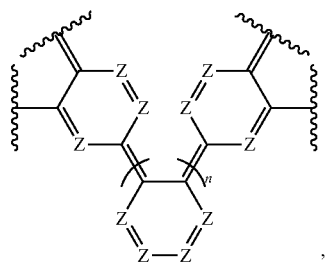

Formula 6

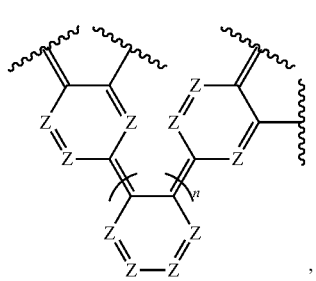

Formula 7

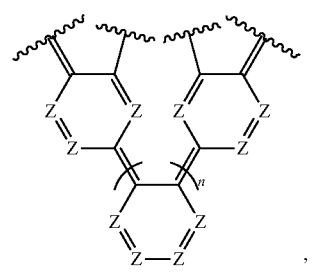

Formula 8 wherein B fused with every A through a single bond and a double bond;

wherein Z is, at each occurrence identically or differently, selected from the group consisting of CR and N; n is, at each occurrence identically or differently, selected from 0, 1, or 2;

wherein, R, R', R", R"', $R_N$ and $R_Y$ are, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, sulfanyl, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein at least one of R, R', R", R"', $R_N$ and $R_Y$ is a group having at least one electron-withdrawing group; and any two adjacent substituents R, R', R", R"', $R_N$ and $R_Y$ can be optionally joined to form a ring;

wherein, when B is selected form Formula 2 or Formula 3, and all of Y are $CR_Y$, X is, at each occurrence identically or differently, selected from the group consisting of S, Se, NR' and CR"R"'.

According to an embodiment of the present disclosure, in the device, the organic layer is a hole injection layer or a hole transporting layer, and the hole injection layer or the hole transporting layer is formed from the compound having the structure of $B(A)_2$ alone.

According to an embodiment of the present disclosure, in the device, the organic layer is a hole injection layer or a hole transporting layer, and the hole injection layer or the hole transporting layer further comprise a at least one hole transporting material, and the hole injection layer is doped with the compound having the structure of $B(A)_2$; and wherein the molar doping ratio of the compound having the structure of $B(A)_2$ to the hole transporting material is from 10000:1 to 1:10000.

According to an embodiment of the present disclosure, in the device, the organic layer is a hole injection layer or a hole transporting layer, and wherein the molar doping ratio of the compound having the structure of $B(A)_2$ to the hole transporting material is from 10:1 to 1:100.

According to an embodiment of the present disclosure, wherein the hole injection layer or the hole transporting layer further comprise a at least one hole transporting material, wherein the hole transporting material comprises a compound having a triarylamine unit, a spirobifluorene compound, a pentacene compound, an oligothiophene compound, an oligophenyl compound, an oligophenylene vinyl compound, an oligofluorene compound, a porphyrin complex or a metal phthalocyanine complex.

According to an embodiment of the present disclosure, the electroluminescent device comprises a plurality of stacks disposed between the anode and the cathode, wherein the stacks comprise a first light-emitting layer and a second light-emitting layer, wherein the first stack comprises a first light-emitting layer, and the second stack comprises a second light-emitting layer, and a charge generation layer is disposed between the first stack and the second stack, wherein the charge generation layer comprises a p-type charge generation layer and an n-type charge generation layer;

wherein the organic layer comprising the compound having the structure of $B(A)_2$ is the p-type charge generation layer; preferably, the p-type charge generation layer further comprises at least one hole transporting material, wherein the molar doping ratio of the compound to the hole transporting material is from 10000:1 to 1:10000.

According to an embodiment of the present disclosure, wherein in the p-type charge generation layer, the molar doping ratio of the compound to the hole transporting material is from 10:1 to 1:100.

According to an embodiment of the present disclosure, the p-type charge generation layer is formed by doping the compound in at least one hole transporting material, wherein the hole transporting material comprises a compound having a triarylamine unit, a spirobifluorene compound, a pentacene compound, an oligothiophene compound, an oligophenyl compound, an oligophenylene vinyl compound, an oligofluorene compound, a porphyrin complex or a metal phthalocyanine complex.

According to an embodiment of the present disclosure, the charge generation layer further includes a buffer layer disposed between the p-type charge generation layer and the n-type charge generation layer, wherein the buffer layer comprises the compound having the structure of $B(A)_2$.

According to an embodiment of the present disclosure, the electroluminescent devices are fabricated via vacuum deposition methods.

According to another embodiment of the present disclosure, a compound formulation is also disclosed, which comprises a compound having the structure of $B(A)_2$. The specific structure of the compound is shown in any of the foregoing embodiments.

Combination with Other Materials

The materials described herein as used for a particular layer in an organic light emitting device may be used in combination with a wide variety of other materials present in the device. The combinations of these materials are described in more detail in U.S. Pat. App. No. 20160359122A1 at paragraphs 0132-0161, which are incorporated by reference in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, compounds disclosed herein may be used in combination with a wide variety of hosts, transporting layers, blocking layers, injection layers, electrodes and other layers that may be present. The combination of these materials is described in detail in paragraphs 0080-0101 of U.S. Pat. App. No. 20150349273, which are incorporated by reference in its entirety. The materials described or referred to the disclosure are non-limiting examples of materials that may be useful in combination with the compounds disclosed herein, and one of skill in the art can readily consult the literature to identify other materials that may be useful in combination.

In the embodiments of material synthesis, the materials can be synthesized according to known literature synthesis methods, for example, US20190181349A1 or by methods well known to the person skilled in the art. Synthetic products were structurally confirmed and tested for properties using one or more conventional equipment in the art (including, but not limited to, nuclear magnetic resonance instrument produced by BRUKER, liquid chromatograph produced by SHIMADZU, liquid chromatography-mass spectrometer produced by SHIMADZU, gas chromatography-mass spectrometer produced by SHIMADZU, differential scanning calorimeters produced by SHIMADZU, fluorescence spectrophotometer produced by SHANGHAI LENGGUANG TECH., electrochemical workstation produced by WUHAN CORRTEST, and sublimation apparatus produced by ANHUI BEQ, etc.) by methods well known to the persons skilled in the art. In the embodiments of the device, the characteristics of the device were also tested using conventional equipment in the art (including, but not limited to, evaporator produced by ANGSTROM ENGINEERING, optical testing system produced by SUZHOU FATAR, life testing system produced by SUZHOU FATAR, and ellipsometer produced by BEIJING ELLITOP, etc.) by methods well known to the persons skilled in the art. As the persons skilled in the art are aware of the above-mentioned equipment use, test methods and other related contents, the inherent data of the sample can be obtained with certainty and without influence, so the above related contents are not further described in this disclosure.

In one embodiment, the LUMO values of selected disclosure compounds are obtained by DFT calculation [GAUSS-09, B3LYP/6-311G(d)], and related compounds and their LUMO values are shown below:

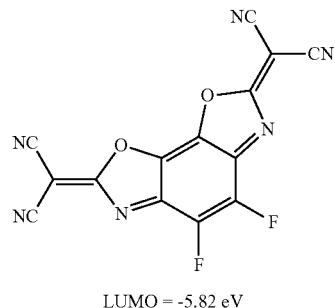

I-1

LUMO = -5.82 eV

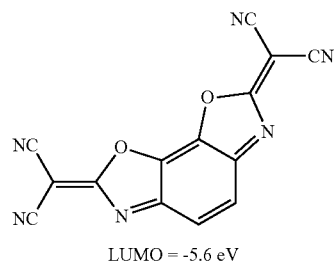

I-2

LUMO = -5.6 eV

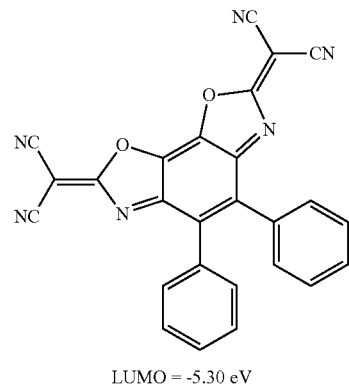

I-3

LUMO = -5.30 eV

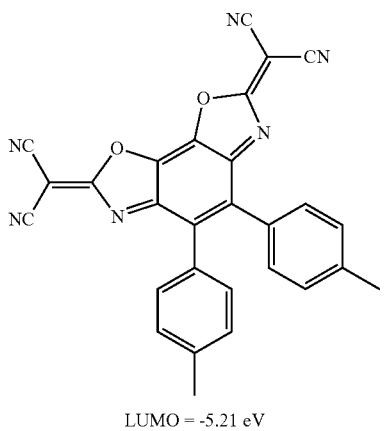

I-4

LUMO = -5.21 eV

-continued
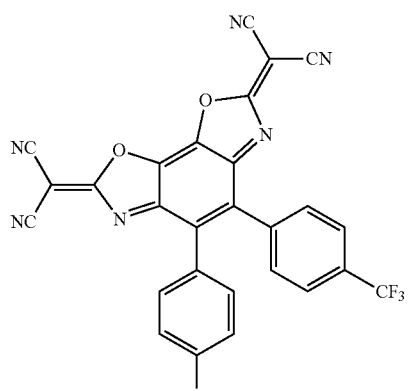
I-8
LUMO = −5.60 eV
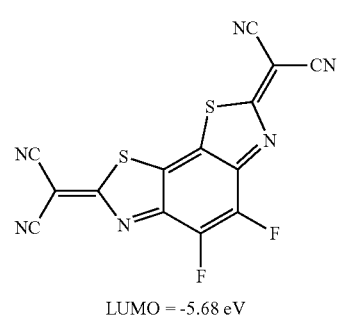
I-17
LUMO = −5.68 eV
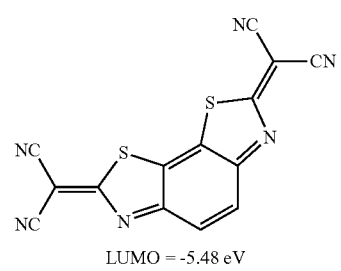
I-18
LUMO = −5.48 eV
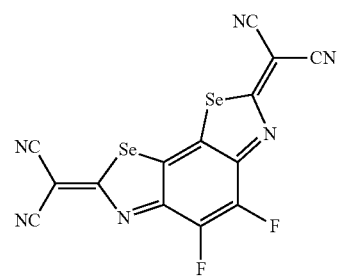
I-33
LUMO = −5.61 eV
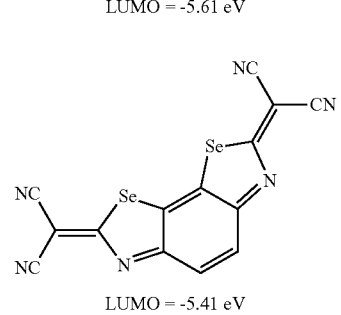
I-34
LUMO = −5.41 eV
-continued
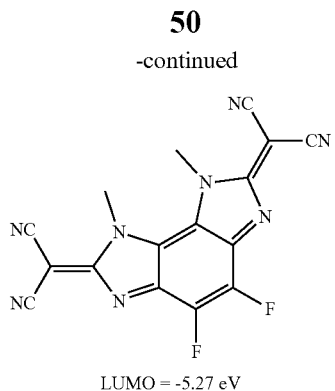
I-49
LUMO = −5.27 eV
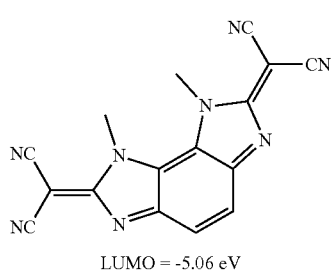
I-50
LUMO = −5.06 eV
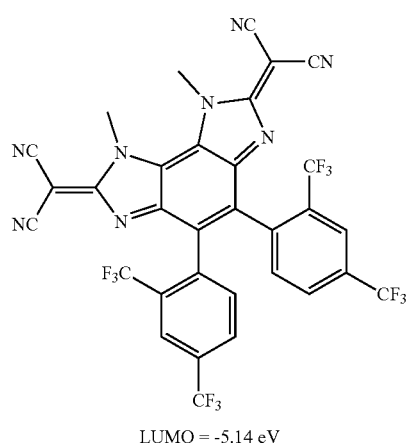
I-60
LUMO = −5.14 eV
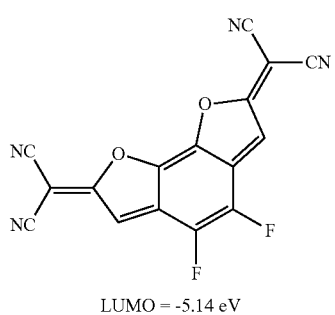
I-65
LUMO = −5.14 eV I-76
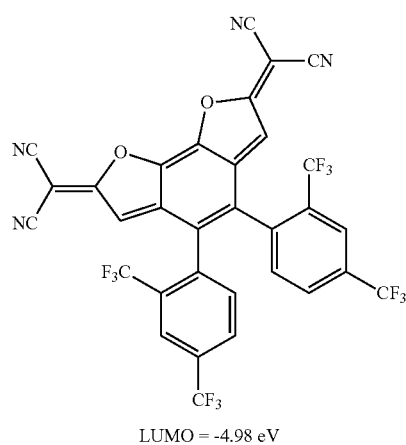
LUMO = −4.98 eV
II-1
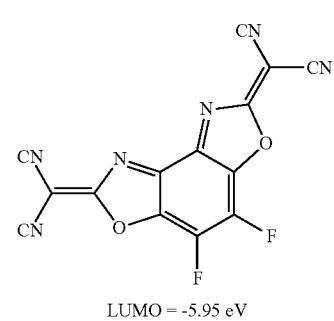
LUMO = −5.95 eV
II-2
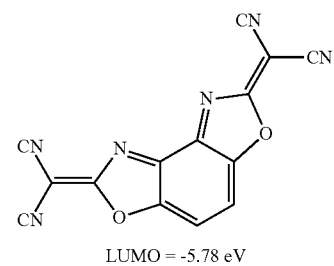
LUMO = −5.78 eV
II-3
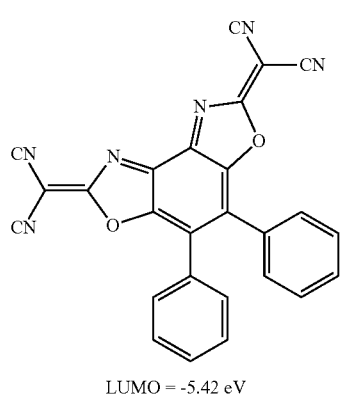
LUMO = −5.42 eV
II-4
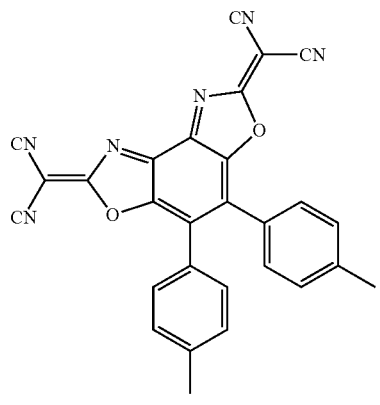
LUMO = −5.31 eV
II-8
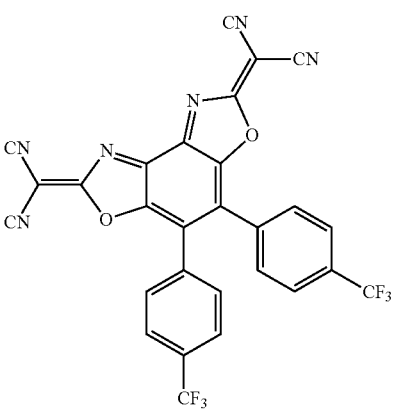
LUMO = −5.75 eV
II-17
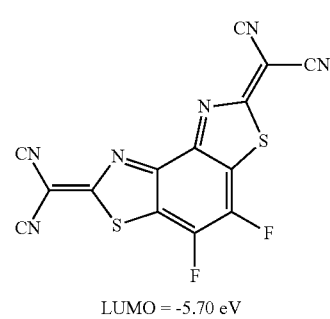
LUMO = −5.70 eV
II-18
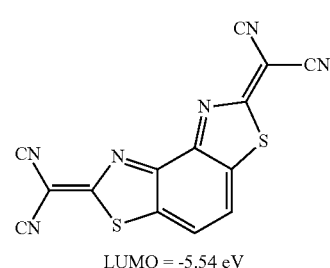
LUMO = −5.54 eV II-33
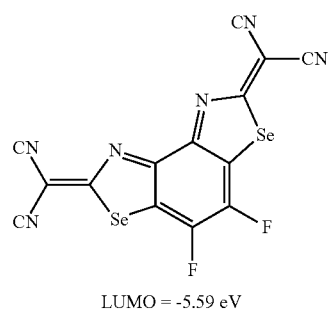
LUMO = −5.59 eV
II-34
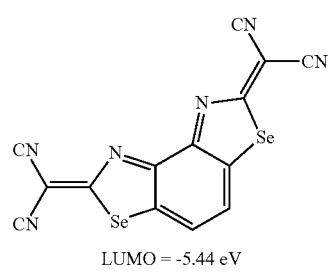
LUMO = −5.44 eV
II-49
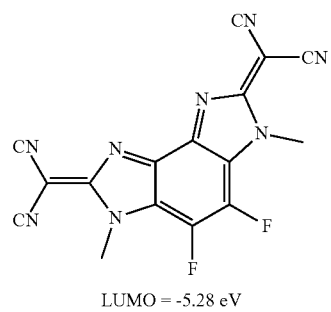
LUMO = −5.28 eV
II-50
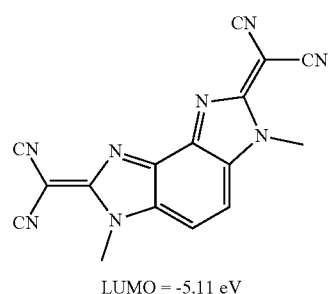
LUMO = −5.11 eV
II-60
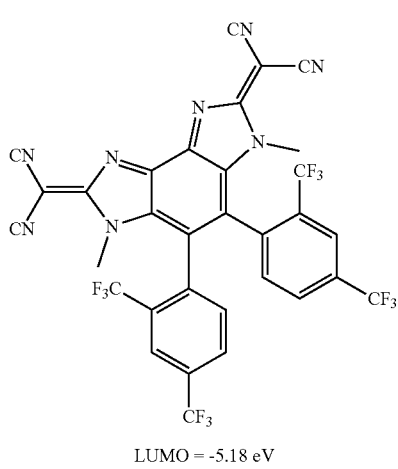
LUMO = −5.18 eV
II-65
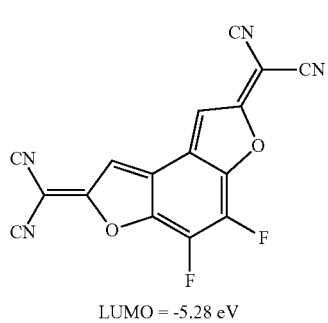
LUMO = −5.28 eV
III-1
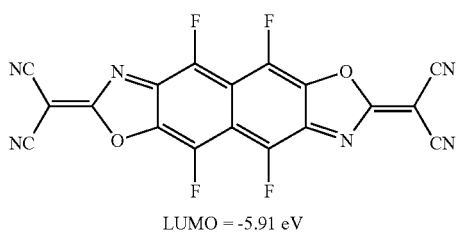
LUMO = −5.91 eV
III-2
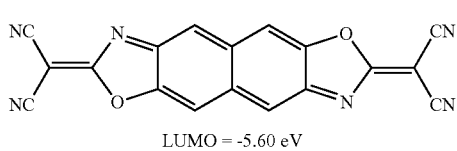
LUMO = −5.60 eV
III-3
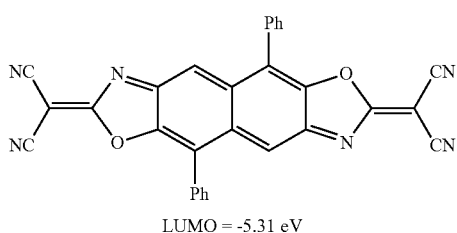
LUMO = −5.31 eV
III-4
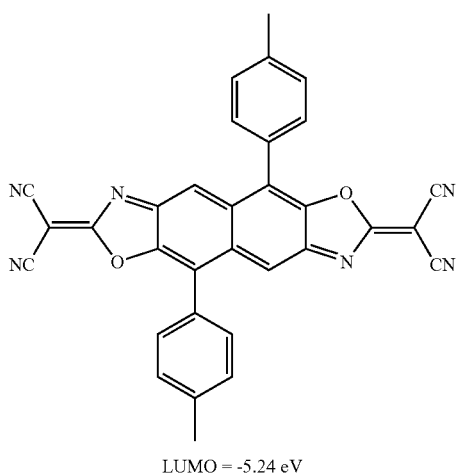
LUMO = −5.24 eV -continued
III-8
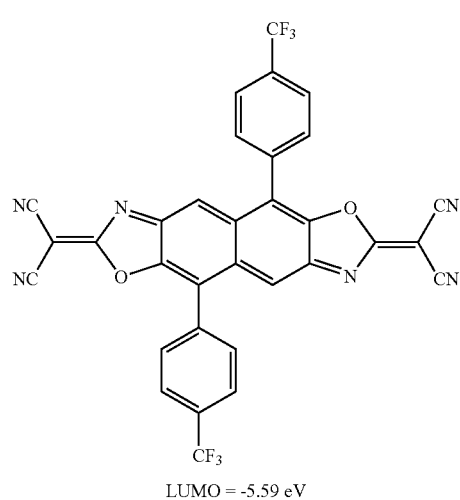
LUMO = −5.59 eV
III-17
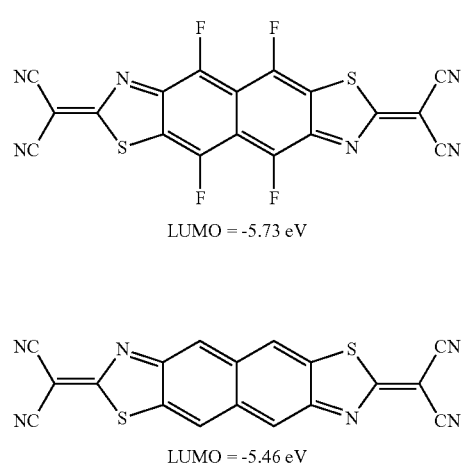
LUMO = −5.73 eV
III-18
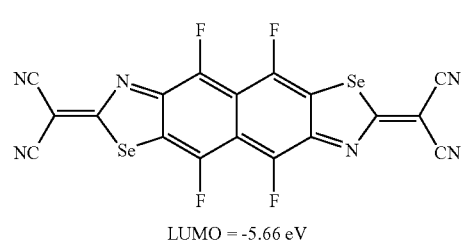
LUMO = −5.46 eV
III-33
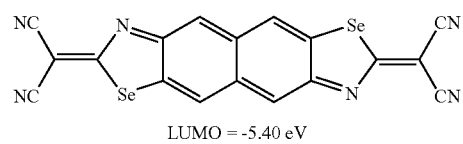
LUMO = −5.66 eV
III-34
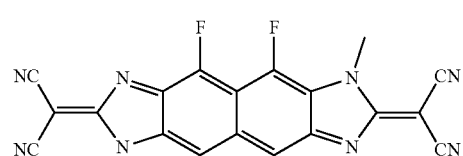
LUMO = −5.40 eV
III-49
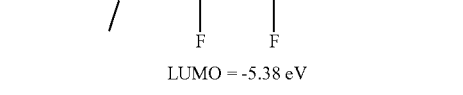
LUMO = −5.38 eV
-continued
III-50
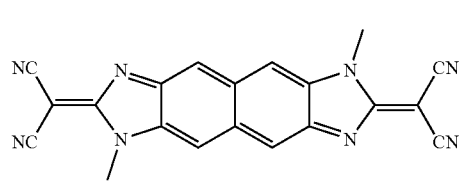
LUMO = −5.06 eV
III-60
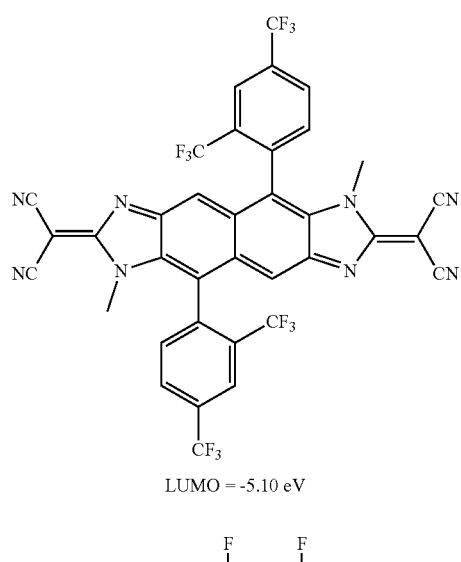
LUMO = −5.10 eV
IV-1
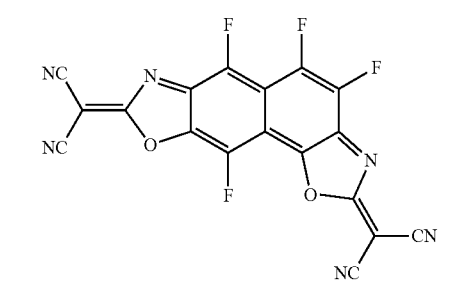
LUMO = −5.87 eV
IV-2
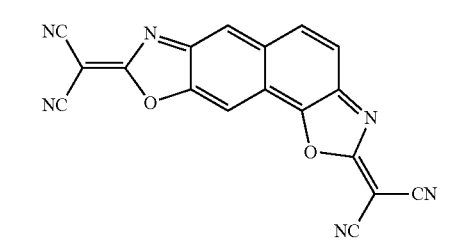
LUMO = −5.54 eV
IV-3
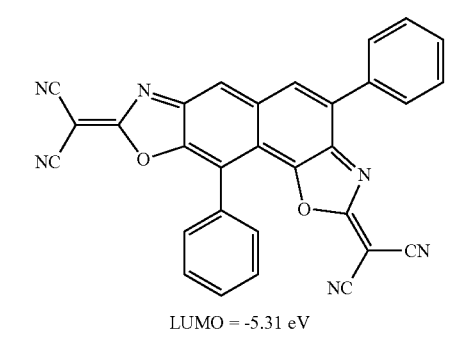
LUMO = −5.31 eV -continued
IV-4
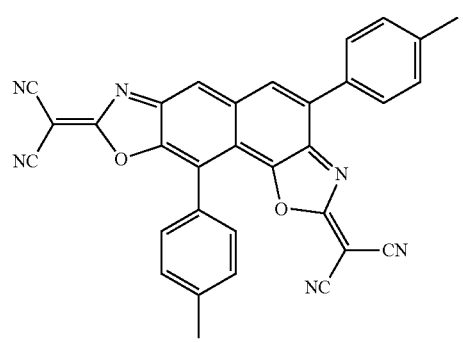
LUMO = -5.24 eV
IV-8
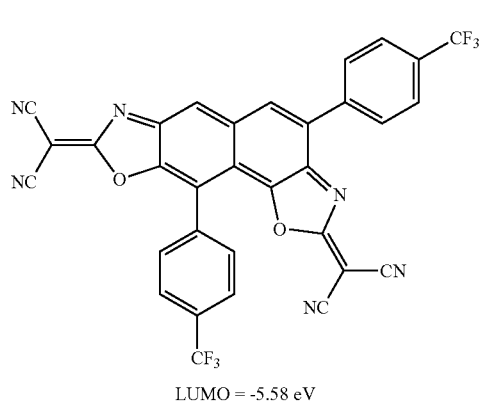
LUMO = -5.58 eV
IV-17
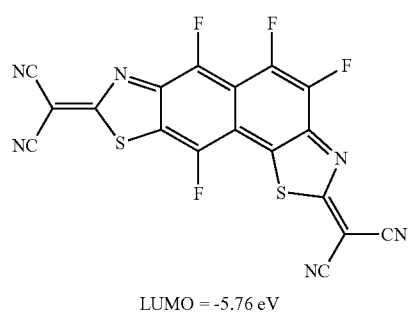
LUMO = -5.76 eV
IV-18
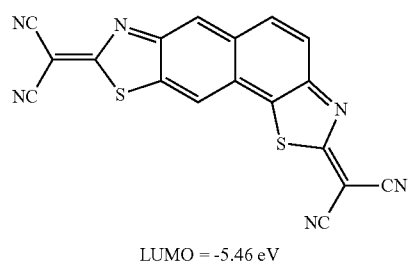
LUMO = -5.46 eV
-continued
IV-33
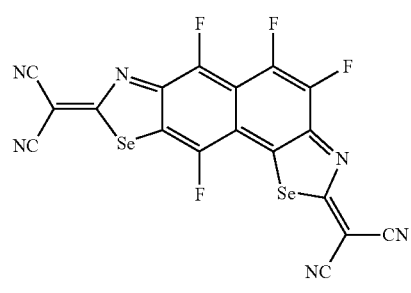
LUMO = -5.69 eV
IV-34
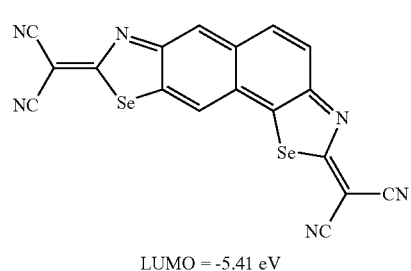
LUMO = -5.41 eV
IV-49
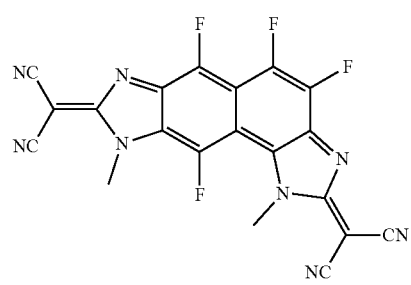
LUMO = -5.40 eV
IV-50
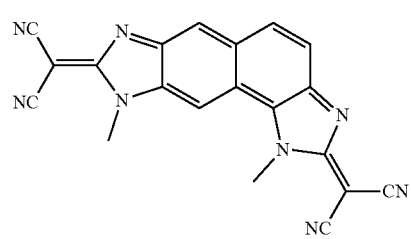
LUMO = -5.08 eV
IV-60
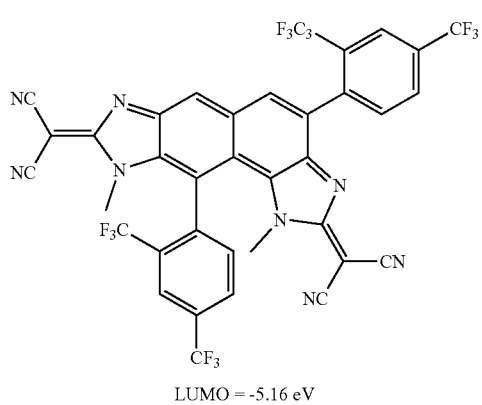
LUMO = -5.16 eV

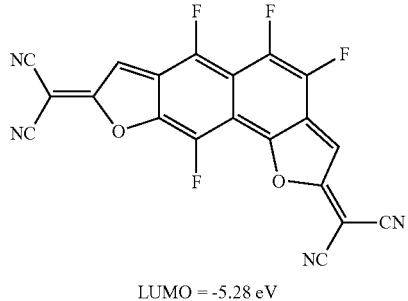
IV-65
LUMO = -5.28 eV
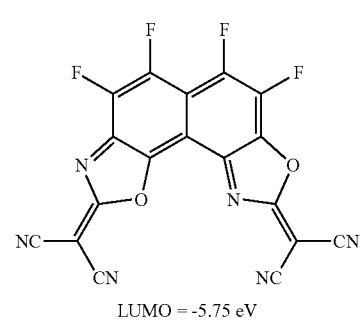
V-1
LUMO = -5.75 eV
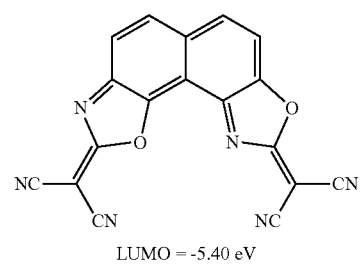
V-2
LUMO = -5.40 eV
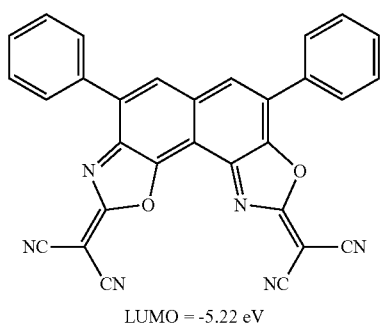
V-3
LUMO = -5.22 eV
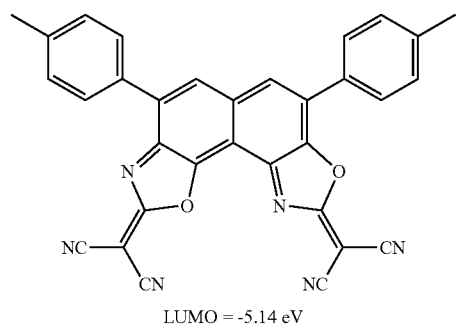
V-4
LUMO = -5.14 eV
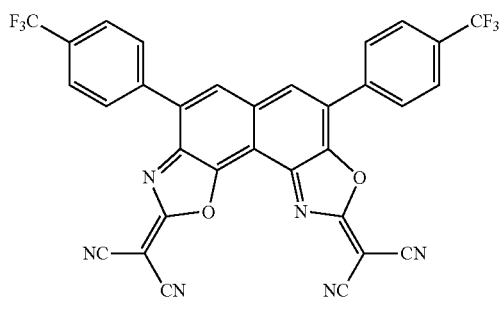
V-8
LUMO = -5.50 eV
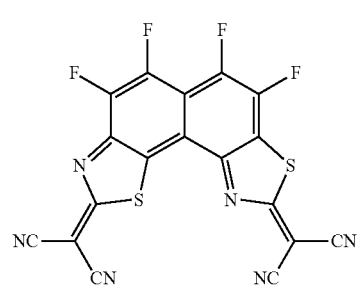
V-17
LUMO = -5.64 eV
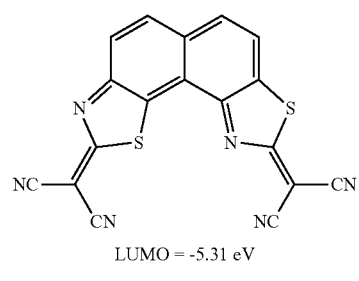
V-18
LUMO = -5.31 eV
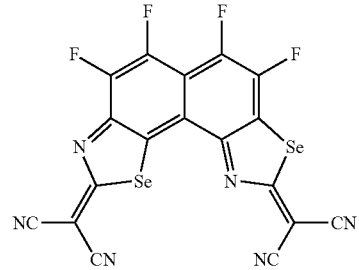
V-33
LUMO = -5.56 eV
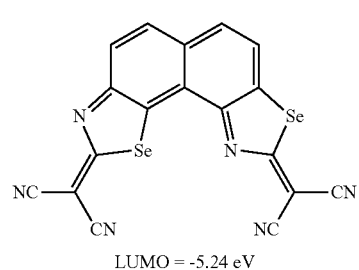
V-34
LUMO = -5.24 eV -continued
V-49
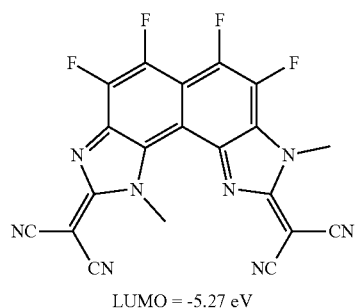
LUMO = −5.27 eV
V-60
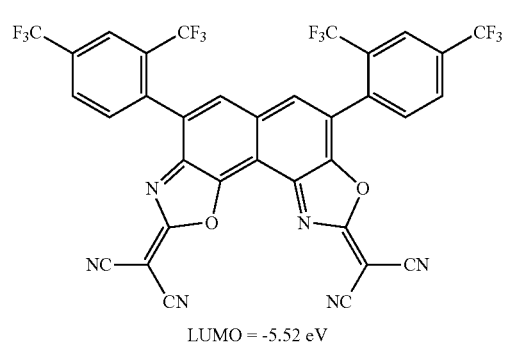
LUMO = −5.52 eV
VI-1
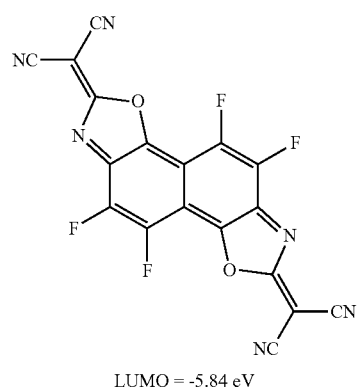
LUMO = −5.84 eV
VI-2
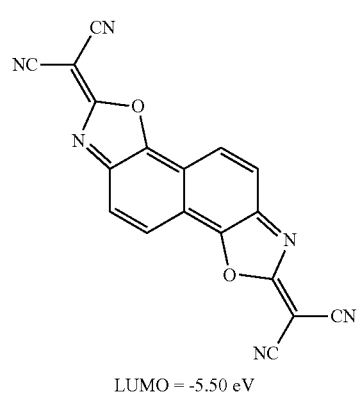
LUMO = −5.50 eV
-continued
VI-3
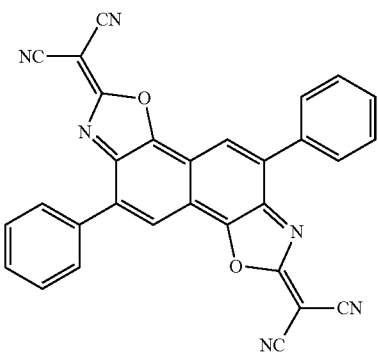
LUMO = −5.33 eV
VI-4
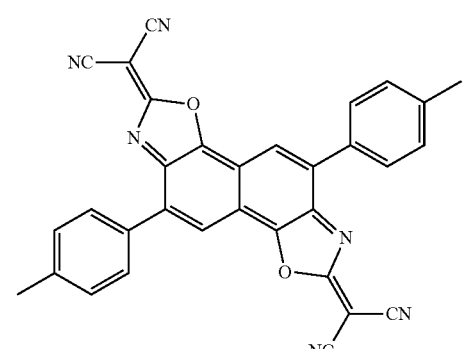
LUMO = −5.26 eV
VI-8
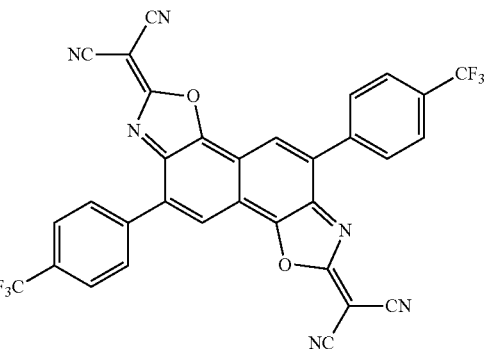
LUMO = −5.61 eV
VI-17
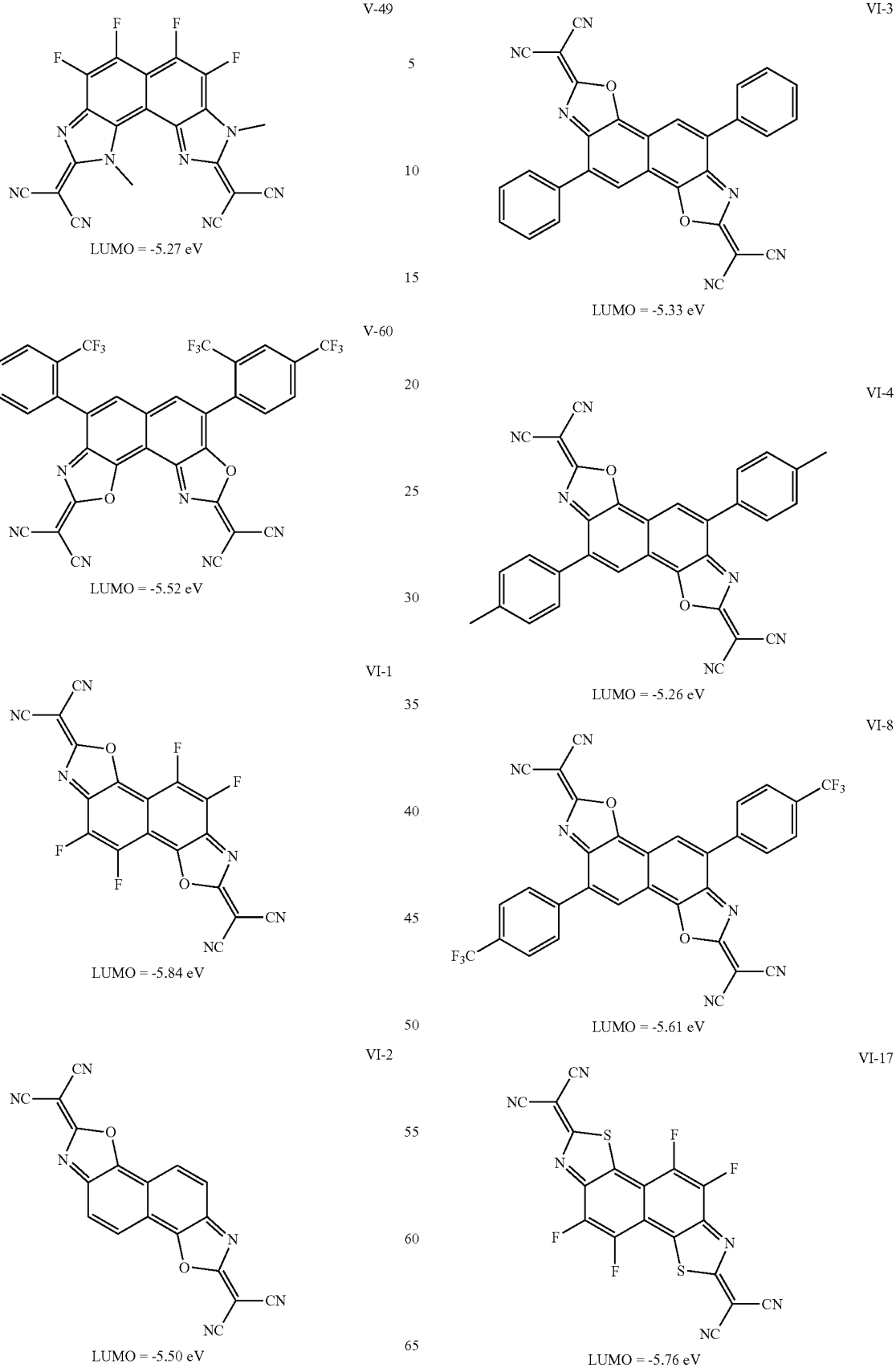
LUMO = −5.76 eV VI-18
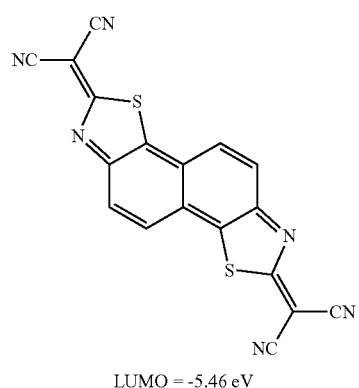
LUMO = −5.46 eV
VI-33
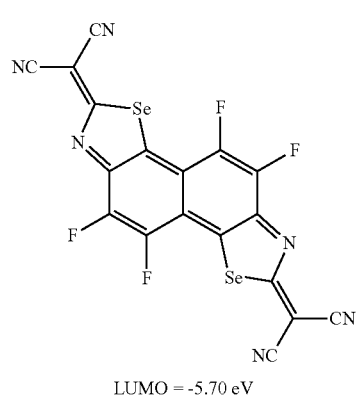
LUMO = −5.70 eV
VI-34
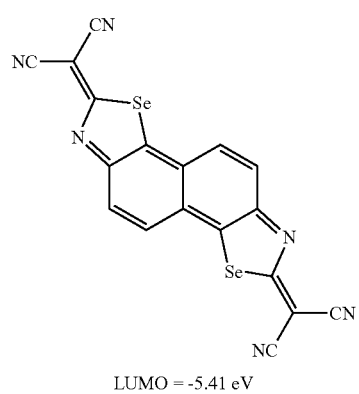
LUMO = −5.41 eV
VII-1
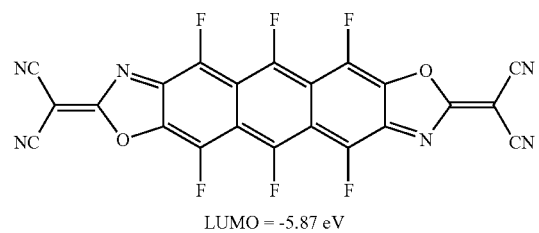
LUMO = −5.87 eV
VII-2
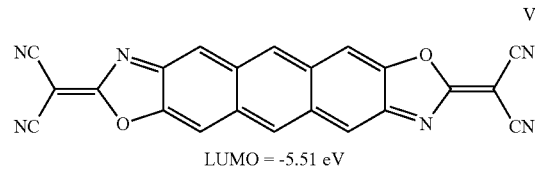
LUMO = −5.51 eV
VII-17
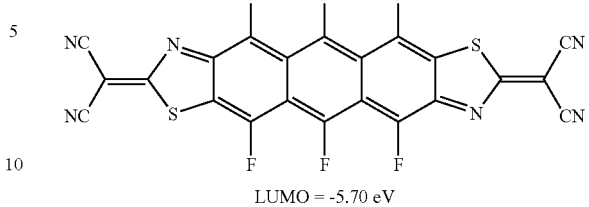
LUMO = −5.70 eV
VII-18
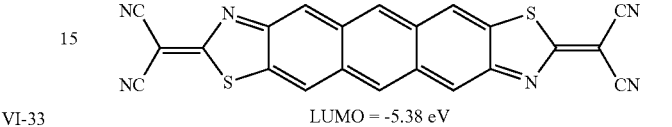
LUMO = −5.38 eV
VII-33
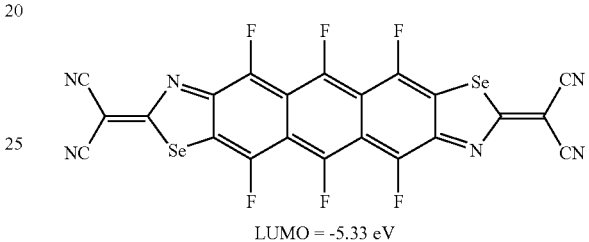
LUMO = −5.33 eV
VII-34
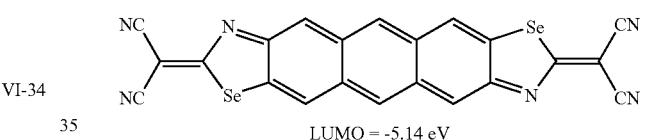
LUMO = −5.14 eV
VII-44
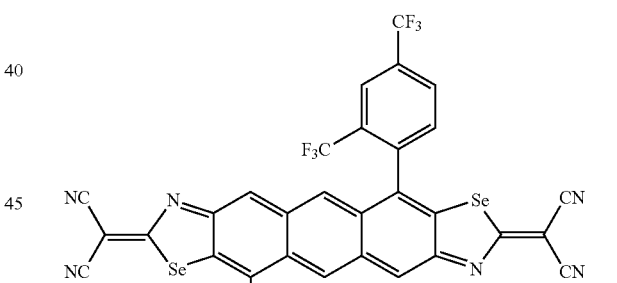
LUMO = −5.38 eV
VII-49
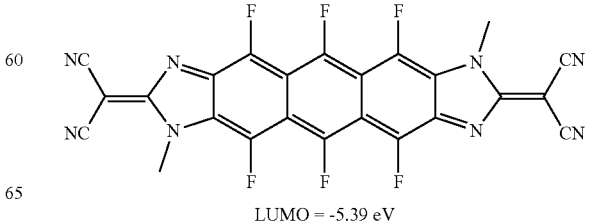
LUMO = −5.39 eV -continued
VII-50
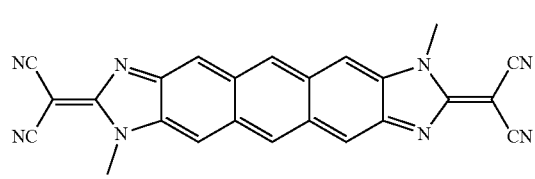
LUMO = −5.04 eV
VII-60
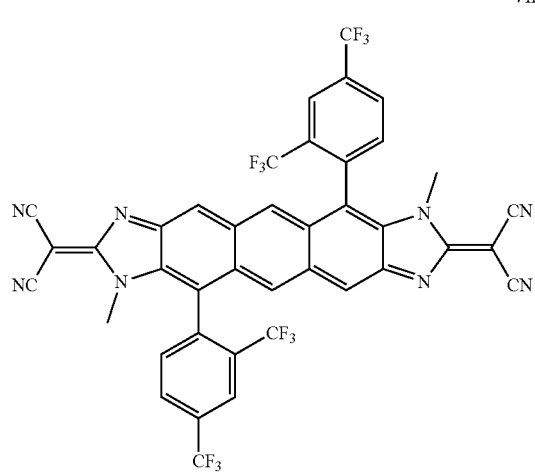
LUMO = −5.10 eV
VIII-1
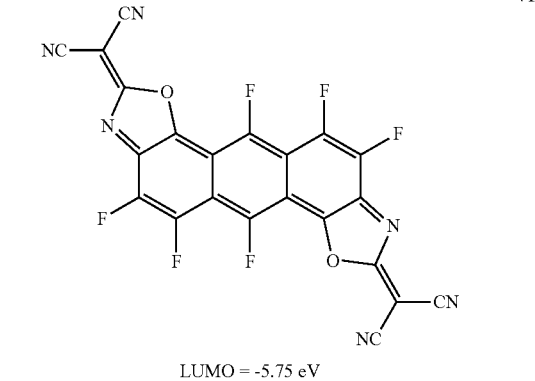
LUMO = −5.75 eV
VIII-2
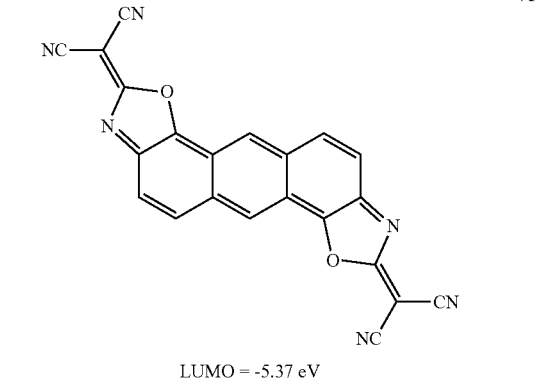
LUMO = −5.37 eV
-continued
VIII-3
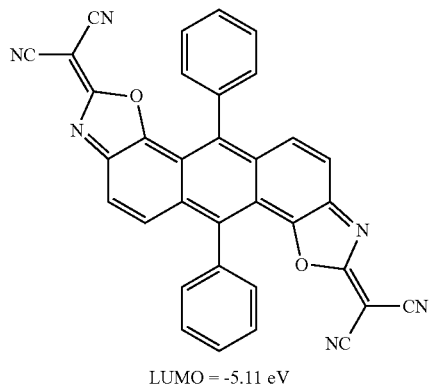
LUMO = −5.11 eV
VIII-8
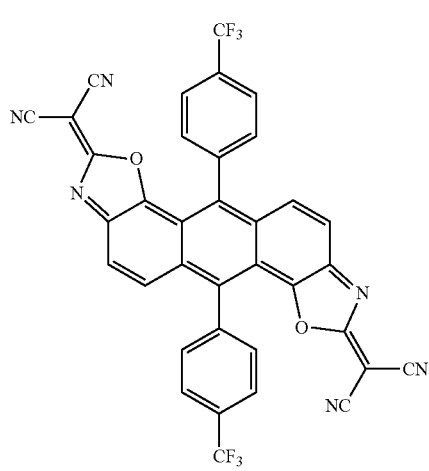
LUMO = −5.35 eV
VIII-12
LUMO = −5.41 eV -continued
VIII-17
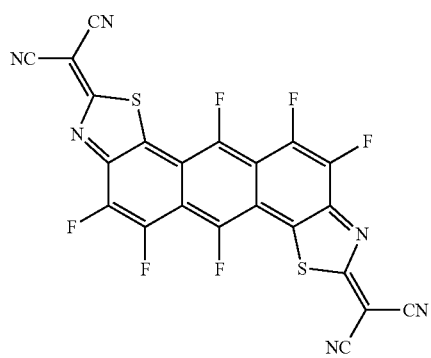
LUMO = −5.72 eV
VIII-18
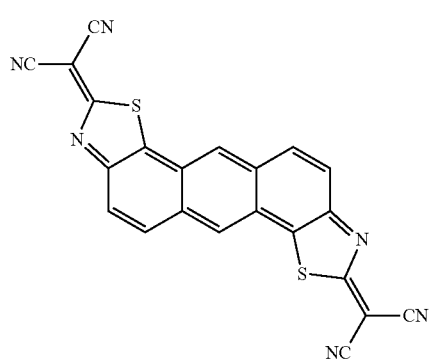
LUMO = −5.36 eV
VIII-33
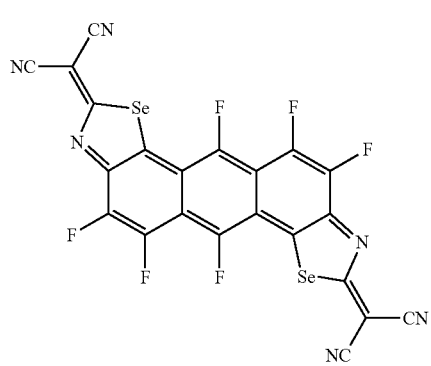
LUMO = −5.67 eV
VIII-34
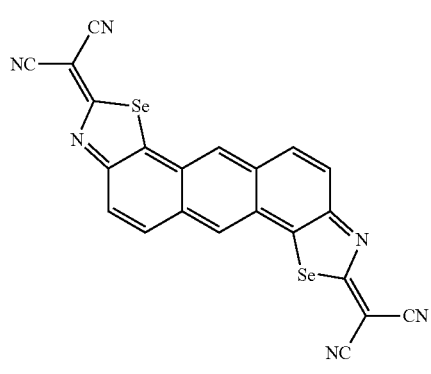
LUMO = −5.32 eV
-continued
VIII-49
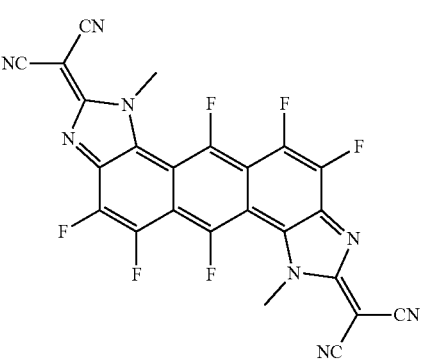
LUMO = −5.37 eV
IX-1
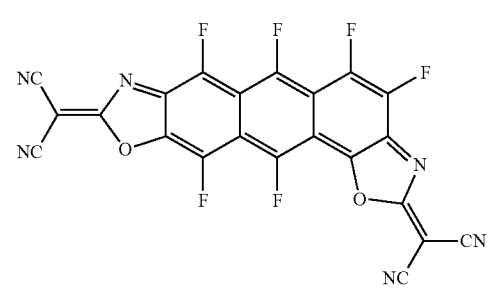
LUMO = −5.81 eV
IX-2
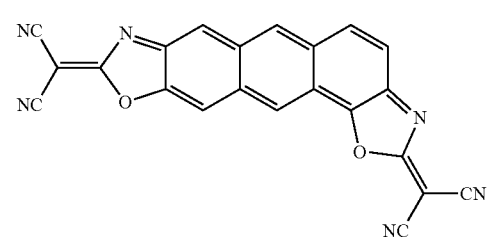
LUMO = −5.44 eV
IX-3
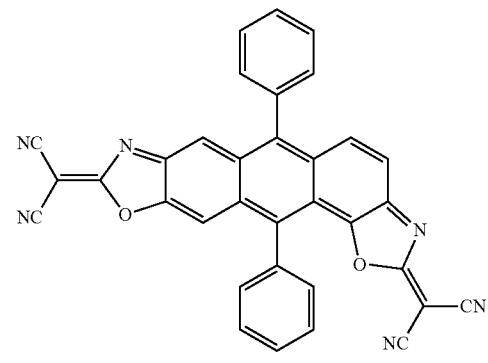
LUMO = −5.20 eV -continued
IX-8
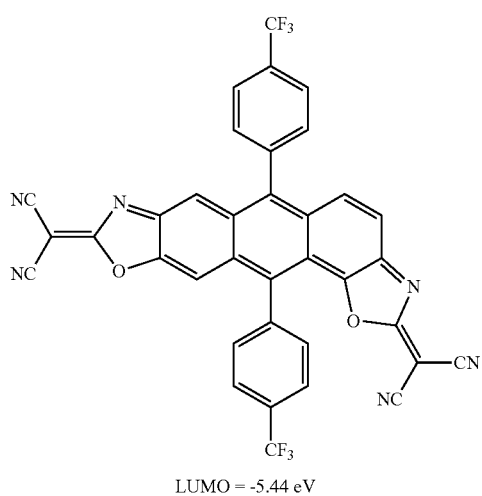
LUMO = -5.44 eV
IX-17
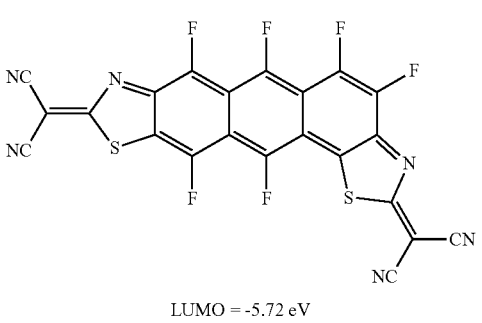
LUMO = -5.72 eV
IX-18
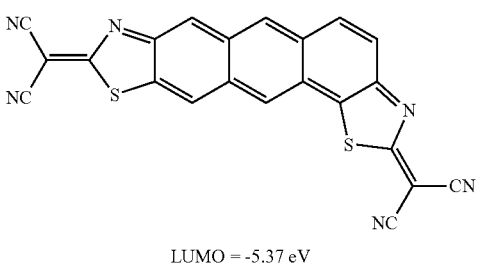
LUMO = -5.37 eV
IX-34
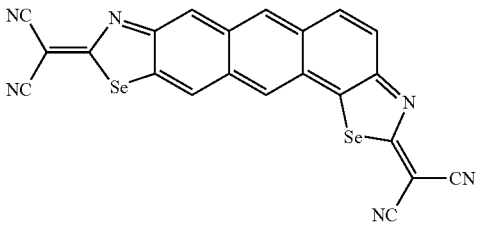
LUMO = -5.34 eV
IX-50
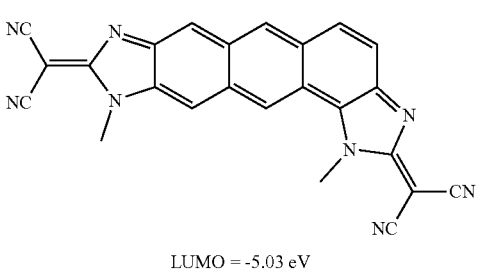
LUMO = -5.03 eV
-continued
IX-60
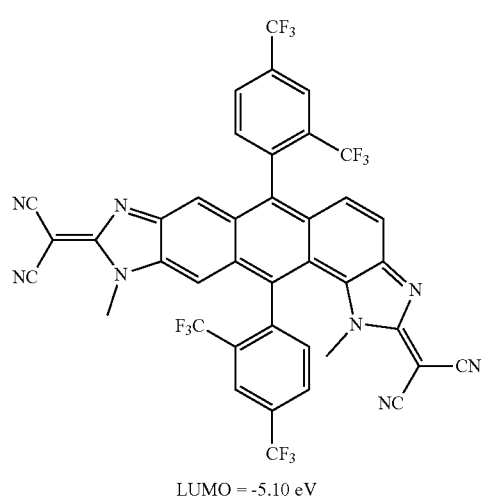
LUMO = -5.10 eV
X-1
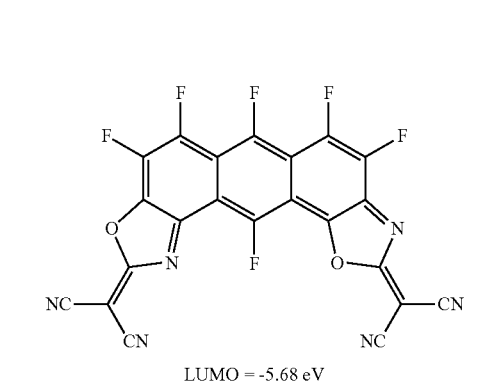
LUMO = -5.68 eV
X-2
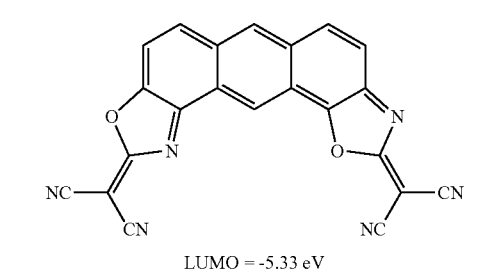
LUMO = -5.33 eV
X-3
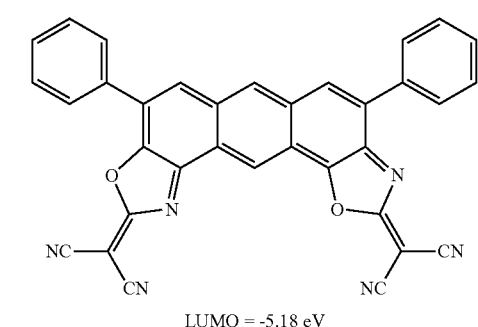
LUMO = -5.18 eV -continued
X-4
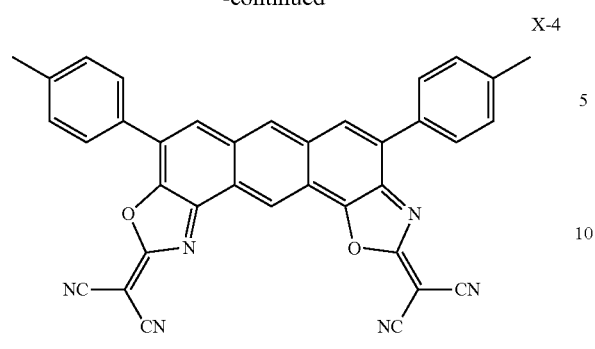
LUMO = −5.11 eV
X-8
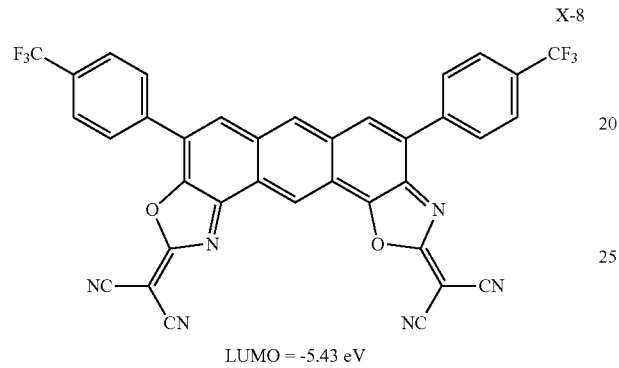
LUMO = −5.43 eV
X-12
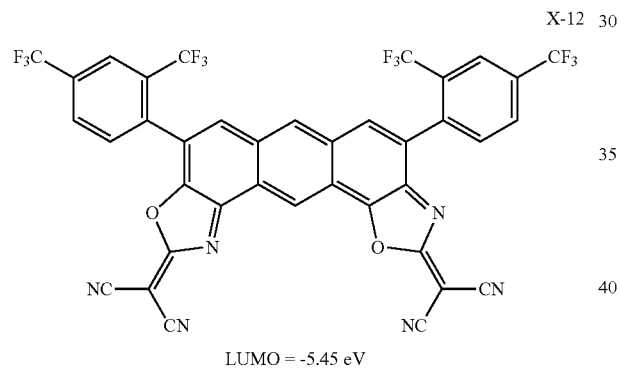
LUMO = −5.45 eV
X-17
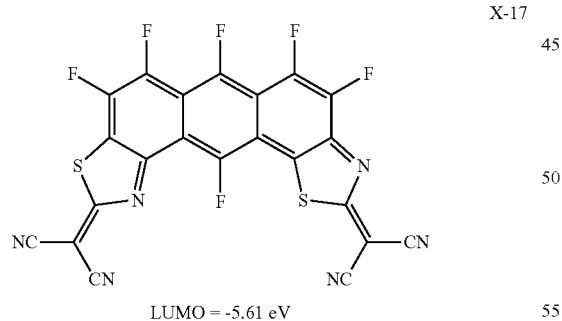
LUMO = −5.61 eV
X-18
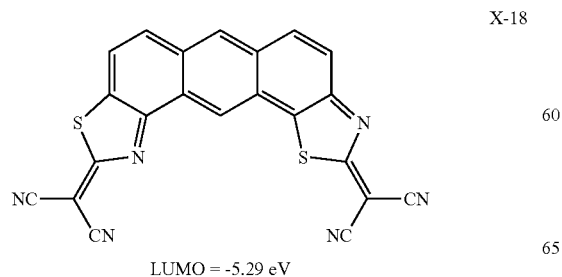
LUMO = −5.29 eV
-continued
X-33
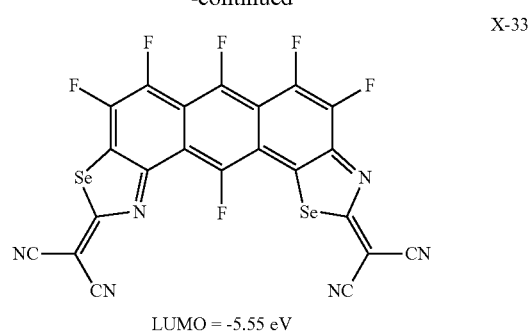
LUMO = −5.55 eV
X-34
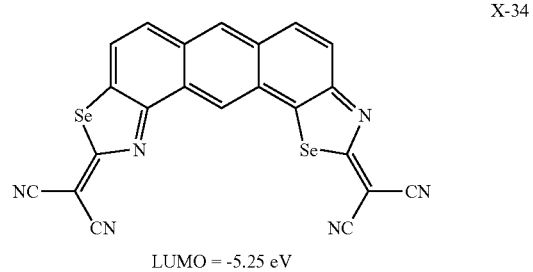
LUMO = −5.25 eV
X-49
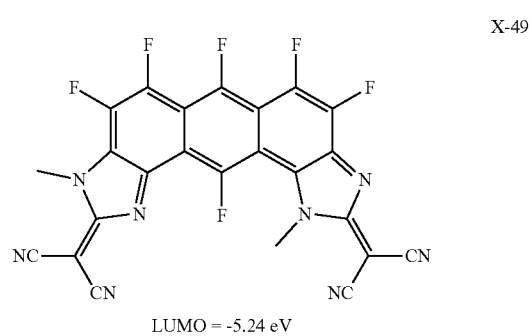
LUMO = −5.24 eV
XI-1
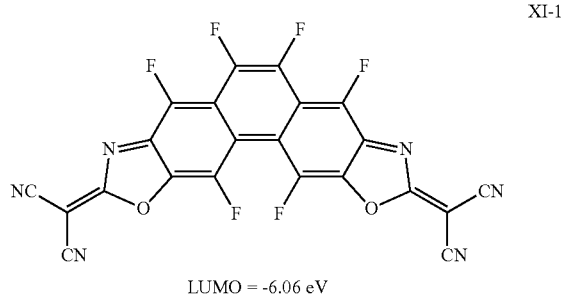
LUMO = −6.06 eV
XI-2
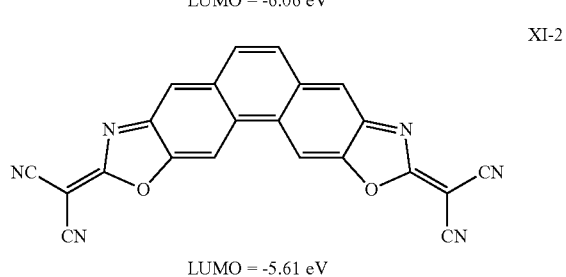
LUMO = −5.61 eV XI-17
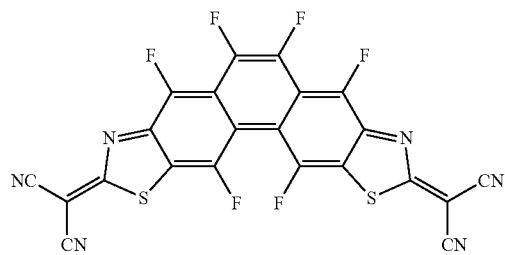
LUMO = −5.93 eV
XI-18
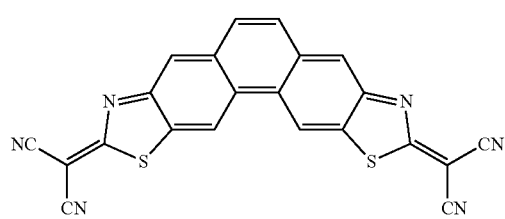
LUMO = −5.52 eV
XI-33
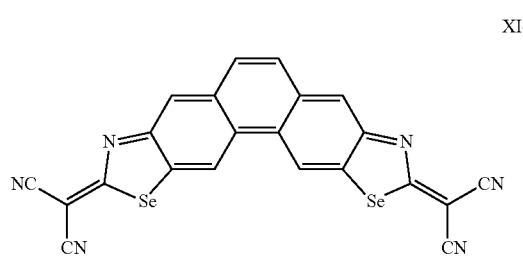
LUMO = −5.48 eV
XI-34
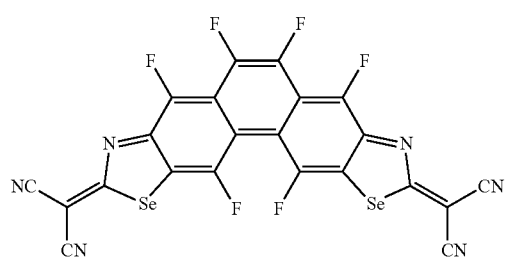
LUMO = −5.87 eV
XI-49
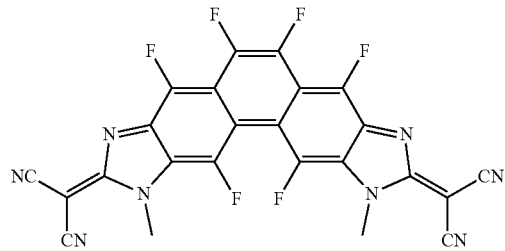
LUMO = −5.60 eV
XI-50
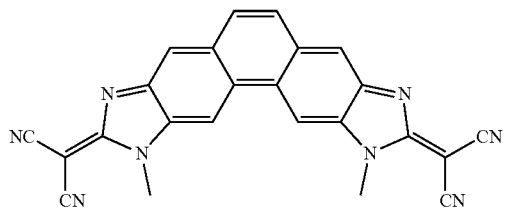
LUMO = −5.17 eV
XI-66
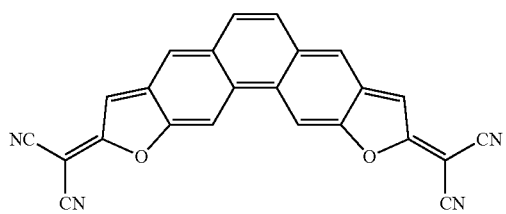
LUMO = −5.05 eV
XII-1
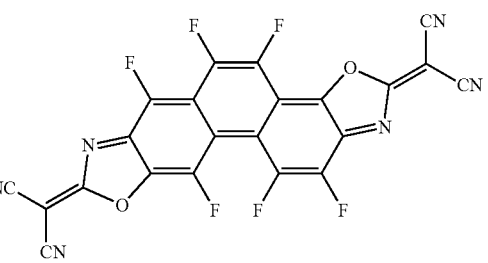
LUMO = −6.03 eV
XII-2
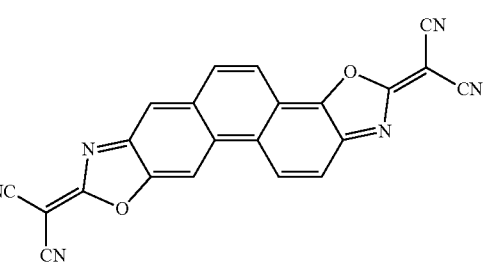
LUMO = −5.58 eV
XII-17
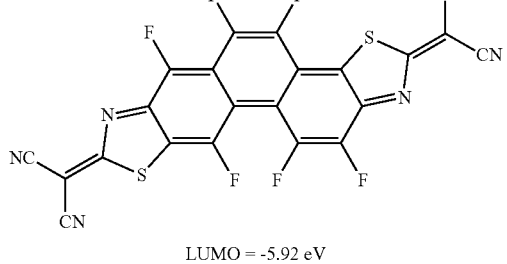
LUMO = −5.92 eV XII-18
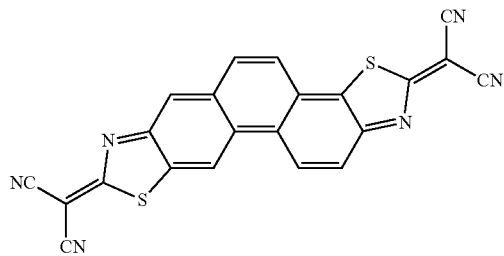
LUMO = -5.51 eV
XII-33
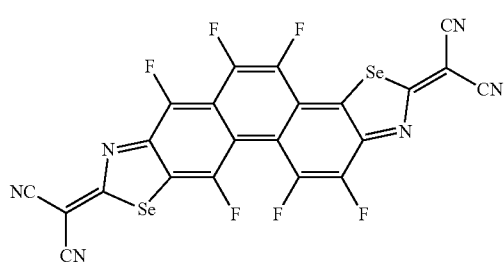
LUMO = -5.86 eV
XII-34
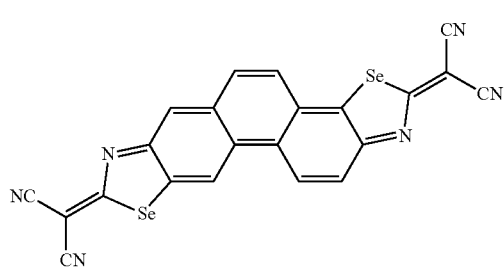
LUMO = -5.47 eV
XII-49
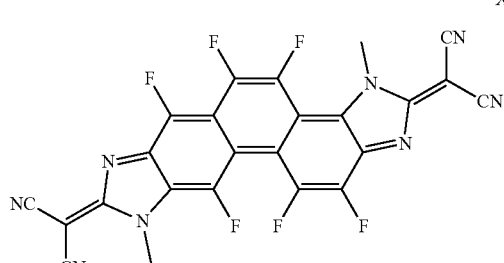
LUMO = -5.58 eV
XII-50
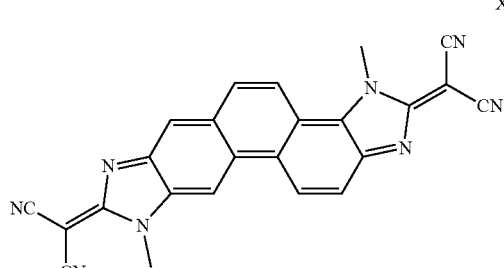
LUMO = -5.14 eV
XII-60
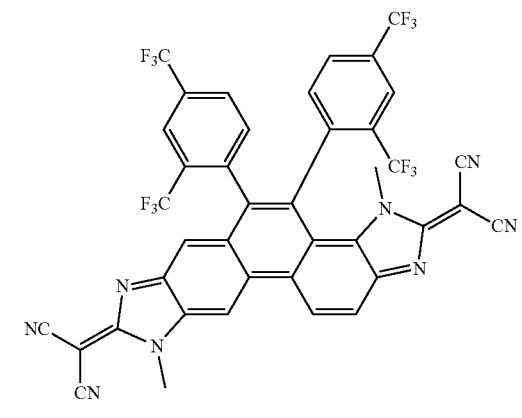
LUMO = -5.25 eV
XIII-1
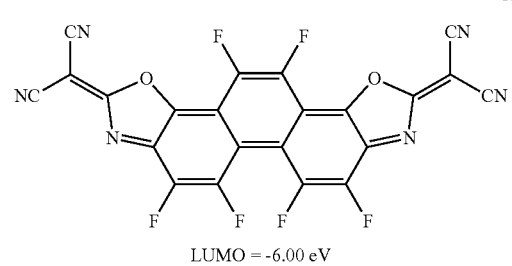
LUMO = -6.00 eV
XIII-2
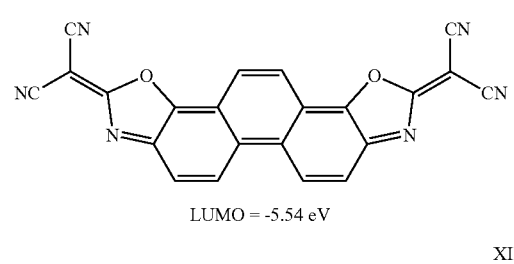
LUMO = -5.54 eV
XIII-17
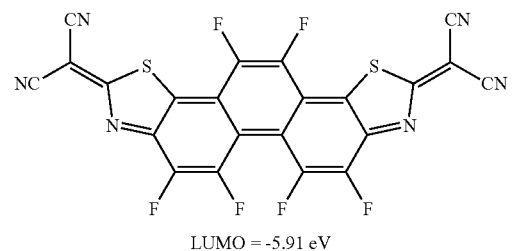
LUMO = -5.91 eV
XIII-18
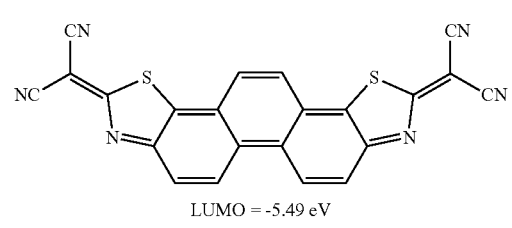
LUMO = -5.49 eV -continued
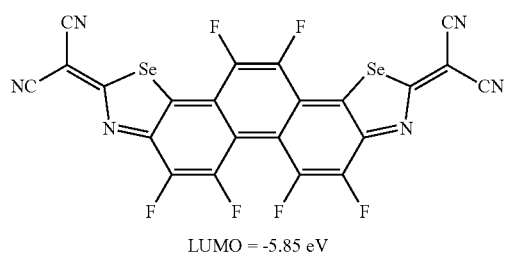
XIII-33
LUMO = −5.85 eV
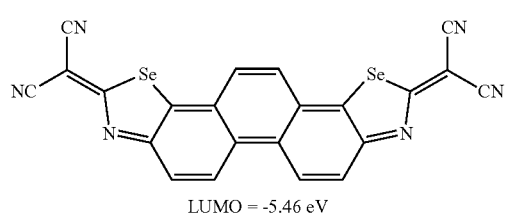
XIII-34
LUMO = −5.46 eV
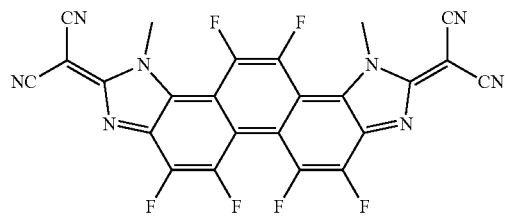
XIII-49
LUMO = −5.57 eV
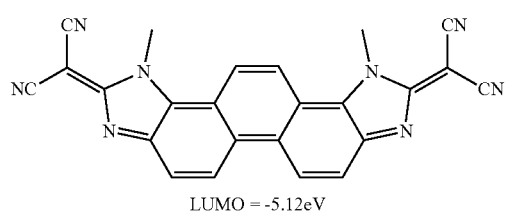
XIII-50
LUMO = −5.12 eV
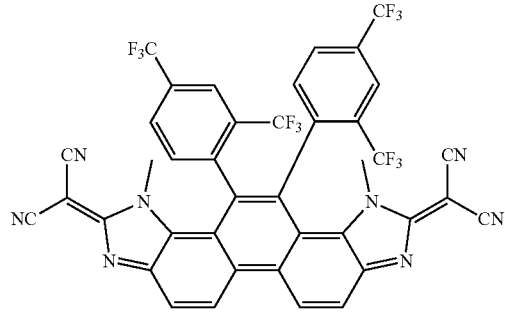
XIII-60
LUMO = −5.24 eV
-continued
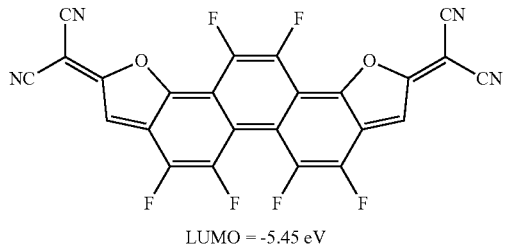
XIII-65
LUMO = −5.45 eV
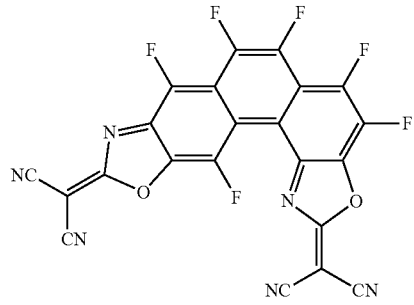
XIV-1
LUMO = −5.98 eV
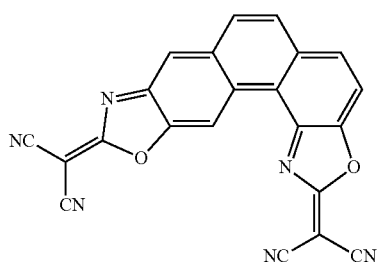
XIV-2
LUMO = −5.55 eV
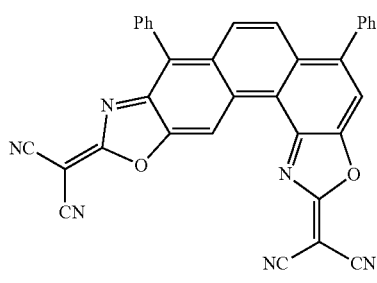
XIV-3
LUMO = −5.34 eV
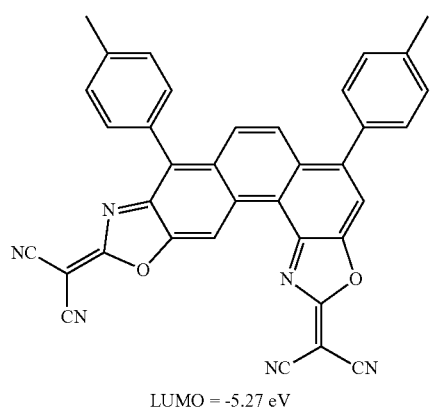
XIV-4
LUMO = −5.27 eV XIV-8
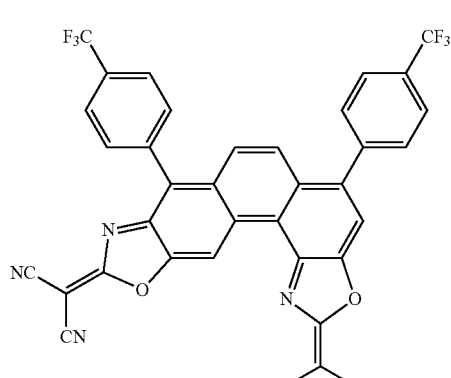
LUMO = −5.61 eV
XIV-17
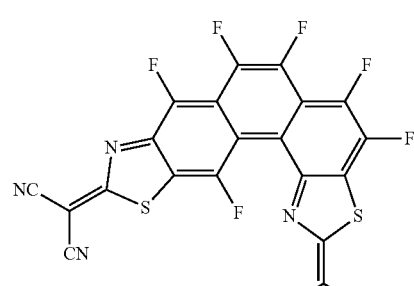
LUMO = −5.83 eV
XIV-18
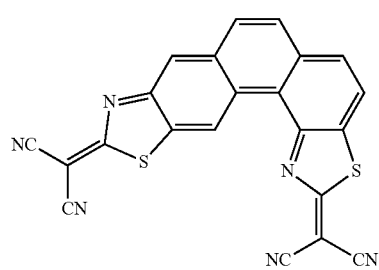
LUMO = −5.45 eV
XIV-33
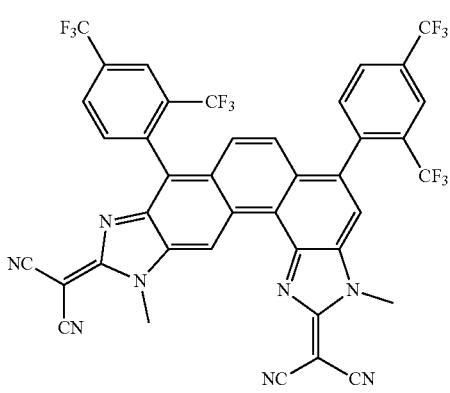
LUMO = −5.77 eV
XIV-34
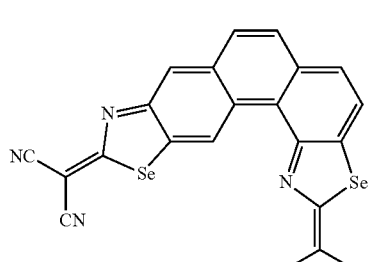
LUMO = −5.40 eV
XIV-49
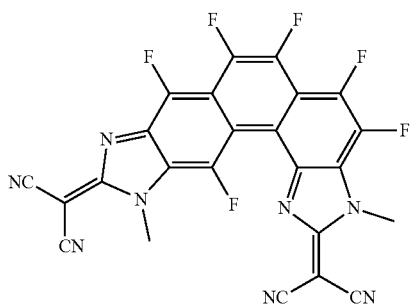
LUMO = −5.49 eV
XIV-50
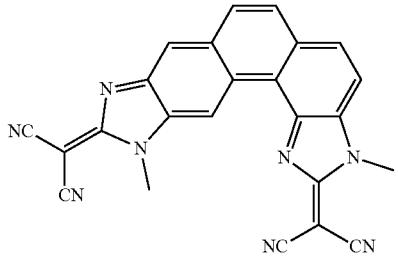
LUMO = −5.07 eV
XIV-60
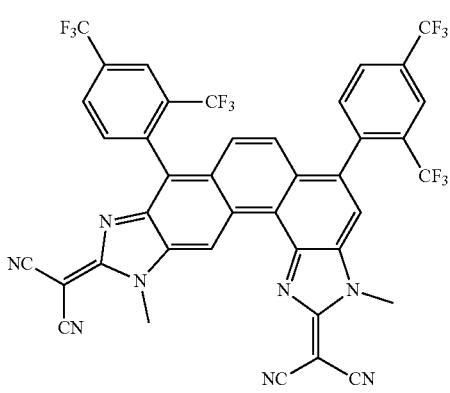
LUMO = −5.22 eV -continued
XIV-66
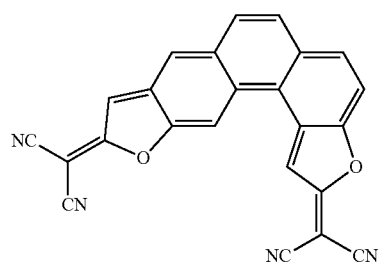
LUMO = −5.09 eV
XIV-76
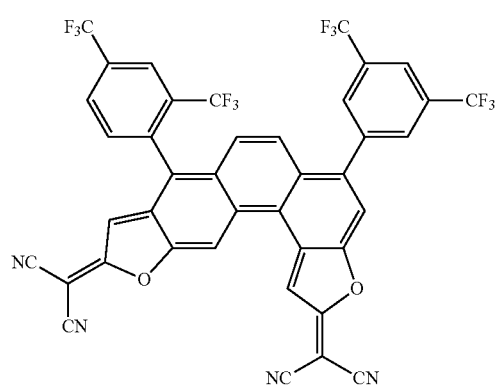
LUMO = −5.25 eV
XV-1
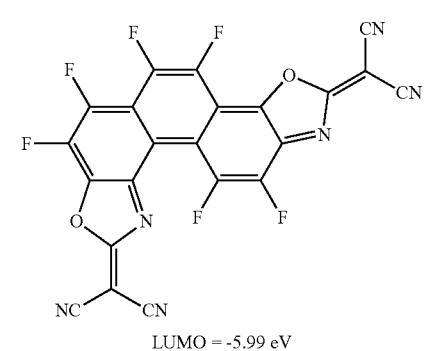
LUMO = −5.99 eV
XV-2
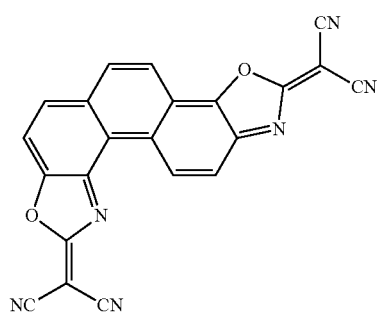
LUMO = −5.60 eV
XV-17
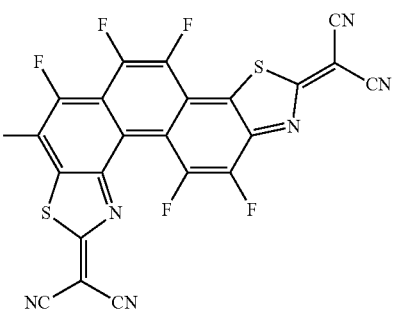
LUMO = −5.83 eV
XV-18
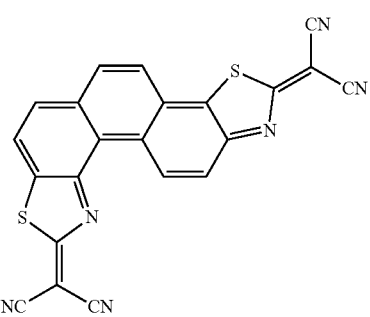
LUMO = −5.49 eV
XV-33
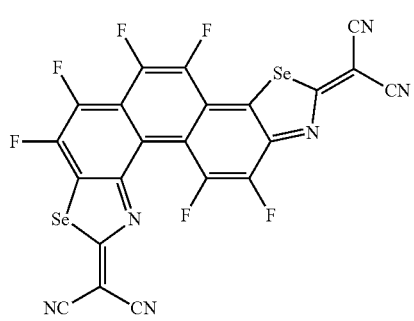
LUMO = −5.76 eV
XV-34
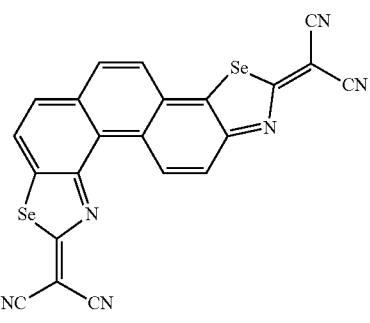
LUMO = −5.44 eV XV-49
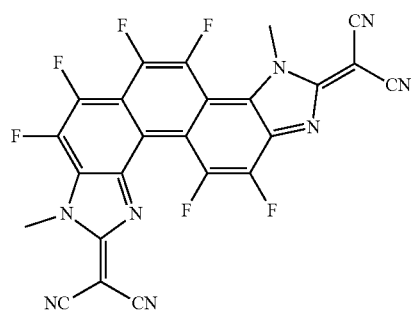
LUMO = -5.47 eV
XV-50
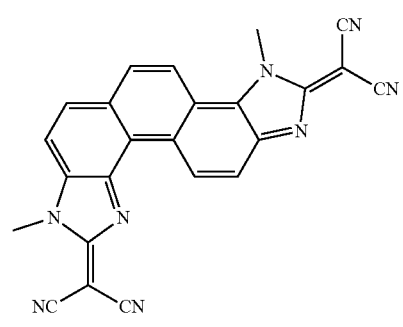
LUMO = -5.10 eV
XV-60
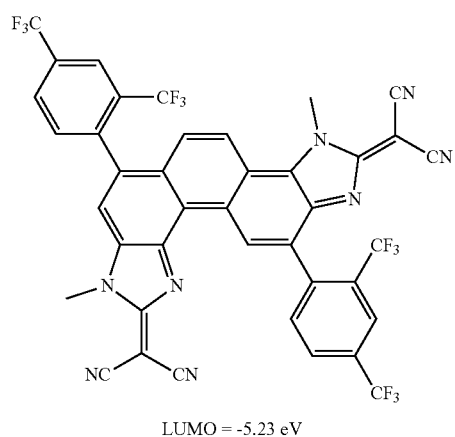
LUMO = -5.23 eV
XV-66
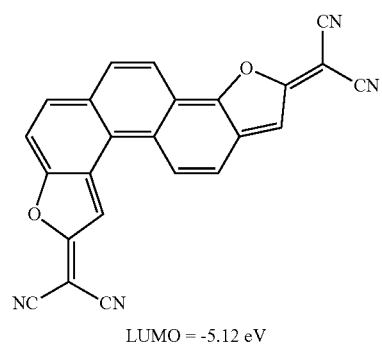
LUMO = -5.12 eV
XV-76
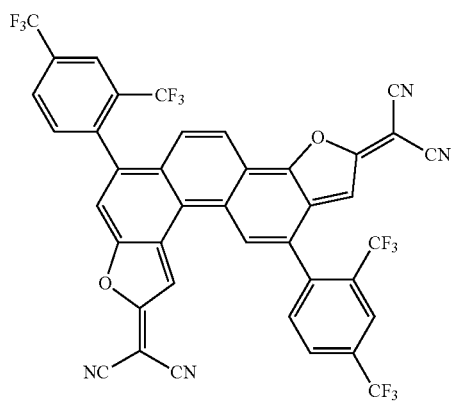
LUMO = -5.22 eV
XVI-1
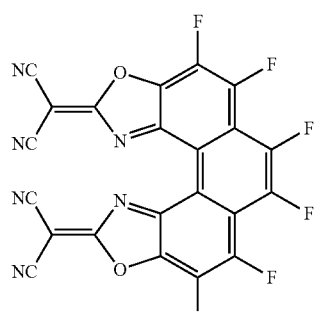
LUMO = -5.86 eV
XVI-2
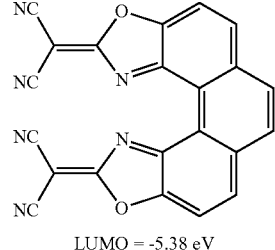
LUMO = -5.38 eV
XVI-17
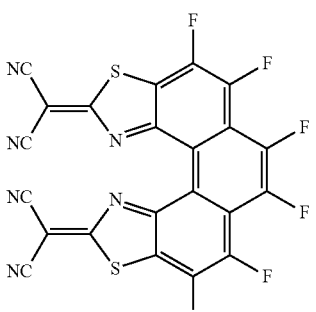
LUMO = -5.59 eV -continued
XVI-18
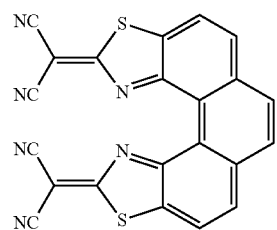
LUMO = −5.34 eV
XVI-33
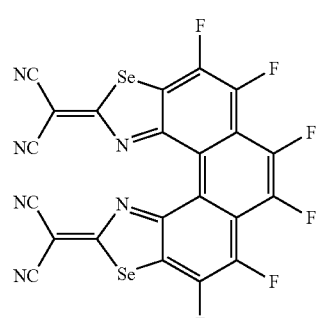
LUMO = −5.53 eV
XVI-34
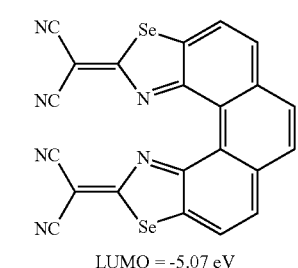
LUMO = −5.07 eV
XVI-44
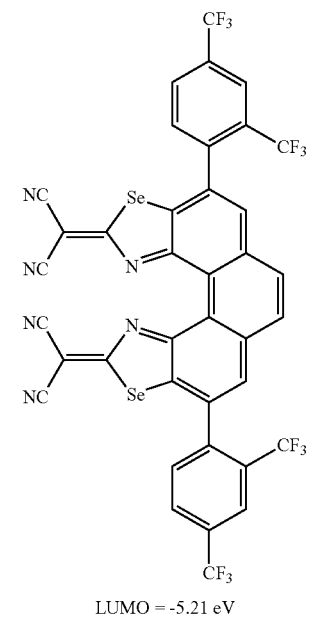
LUMO = −5.21 eV
-continued
XVI-49
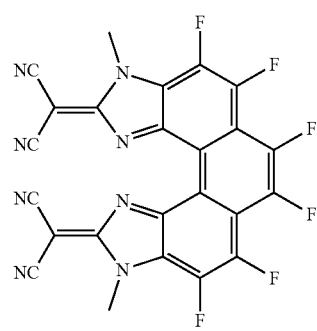
LUMO = −5.27 eV
XVI-66
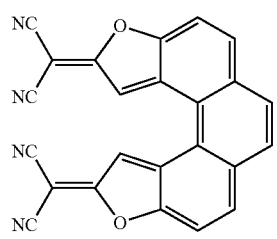
LUMO = −5.14 eV
XVI-76
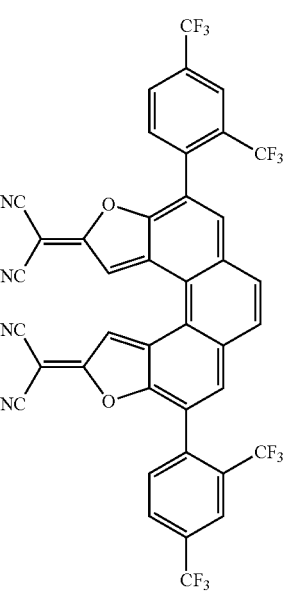
LUMO = −5.28 eV
XVI-82
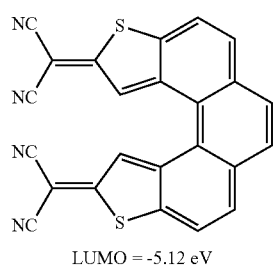
LUMO = −5.12 eV XVI-92
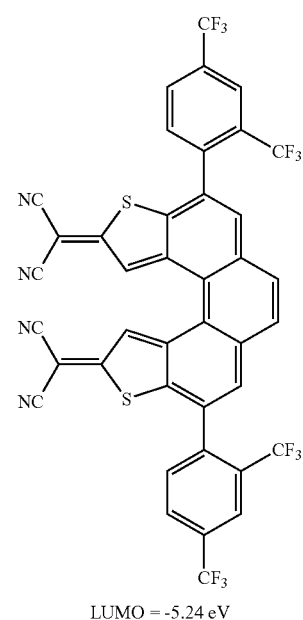
LUMO = −5.24 eV
XVII-1
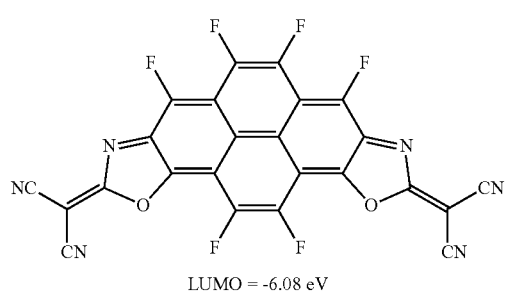
LUMO = −6.08 eV
XVII-2
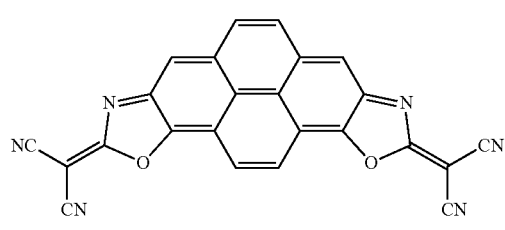
LUMO = −5.63 eV
XVII-17
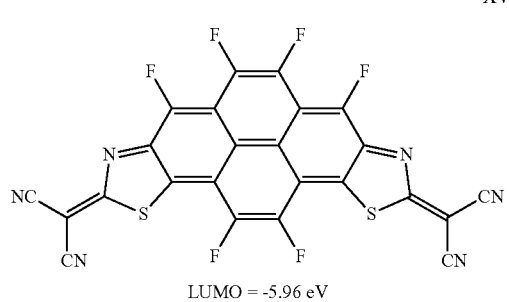
LUMO = −5.96 eV
XVII-18
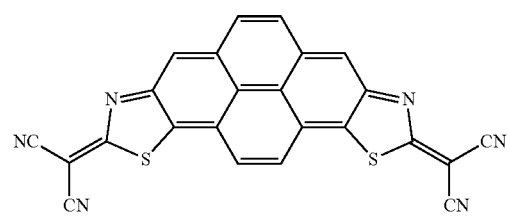
LUMO = −5.56 eV
XVII-33
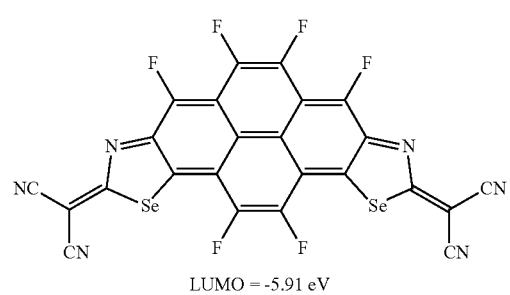
LUMO = −5.91 eV
XVII-34
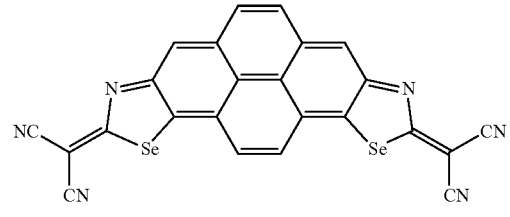
LUMO = −5.53 eV
XVII-49
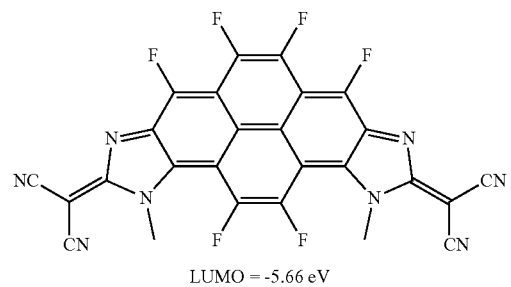
LUMO = −5.66 eV
XVII-50
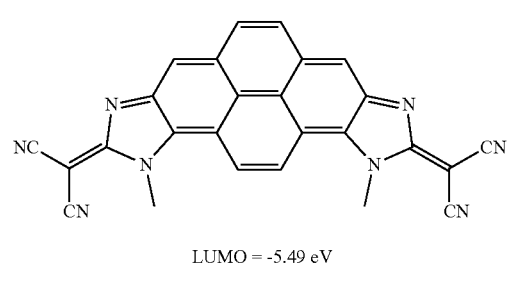
LUMO = −5.49 eV -continued
XVII-66
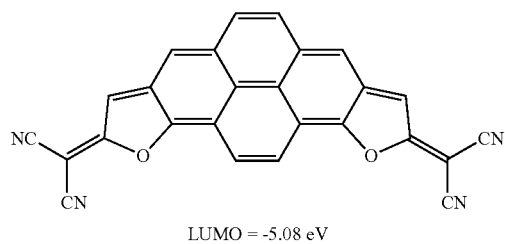
LUMO = -5.08 eV
XVII-76
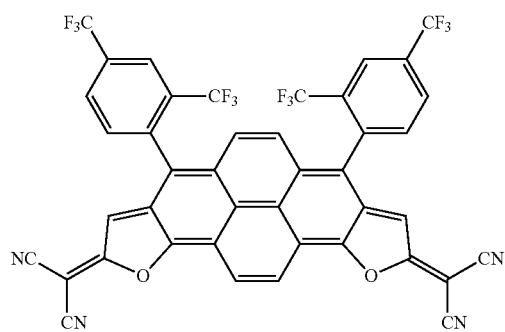
LUMO = -5.18 eV
XVIII-1
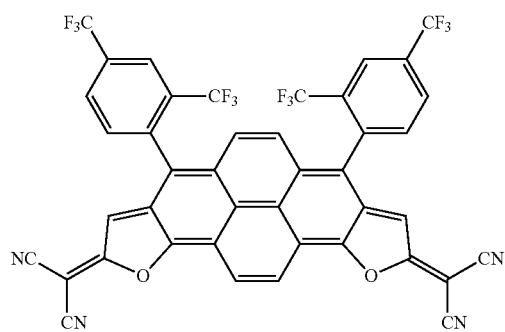
LUMO = -6.08 eV
XVIII-2
LUMO = -5.63 eV
XVIII-17
LUMO = -5.97 eV
-continued
XVIII-18
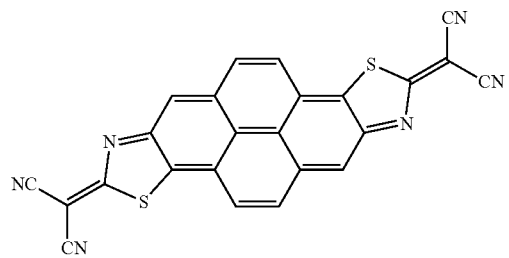
LUMO = -5.57 eV
XVIII-33
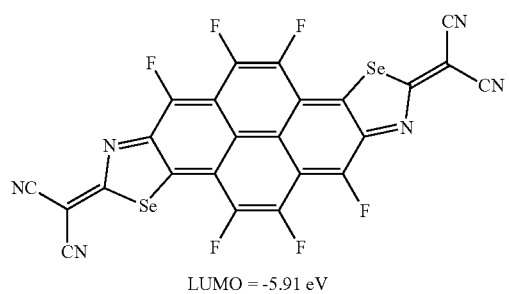
LUMO = -5.91 eV
XVIII-34
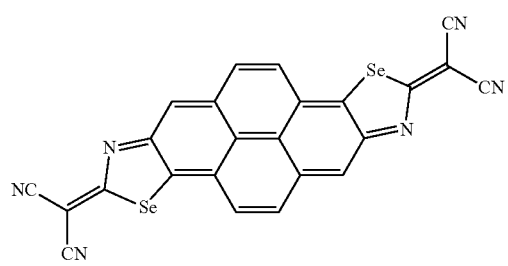
LUMO = -5.53 eV
XVIII-49
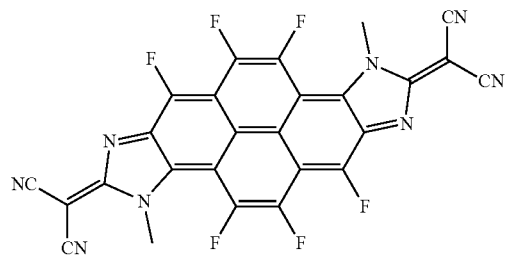
LUMO = -5.65 eV
XVIII-50
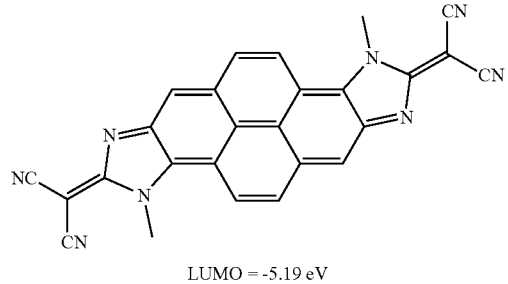
LUMO = -5.19 eV -continued
XVIII-66
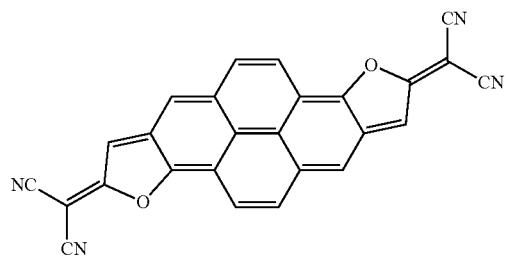
LUMO = -5.08 eV
XVIII-76
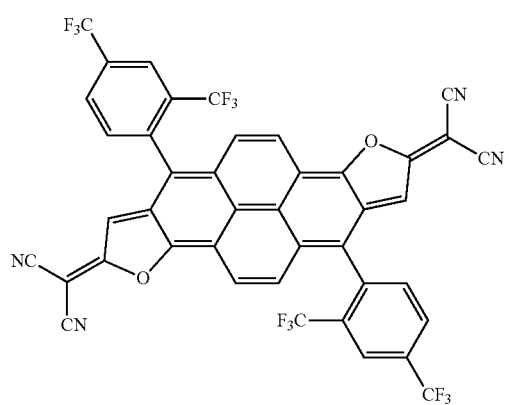
LUMO = -5.19 eV
XIX-1
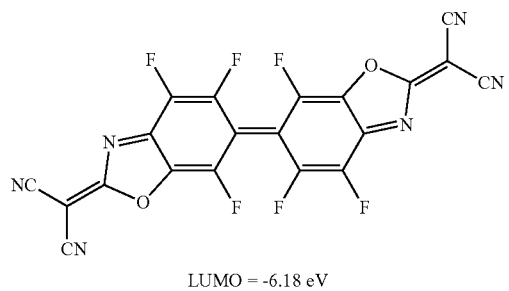
LUMO = -6.18 eV
XIX-2
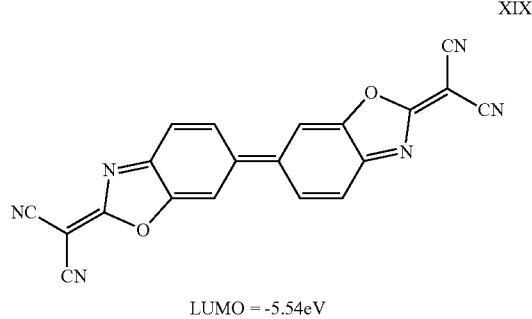
LUMO = -5.54 eV
-continued
XIX-17
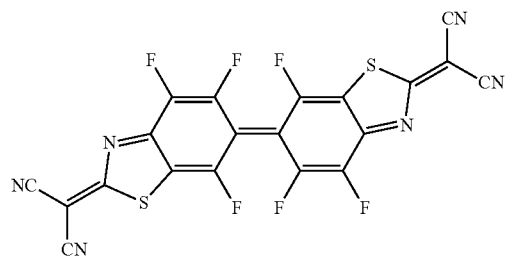
LUMO = -6.06 eV
XIX-18
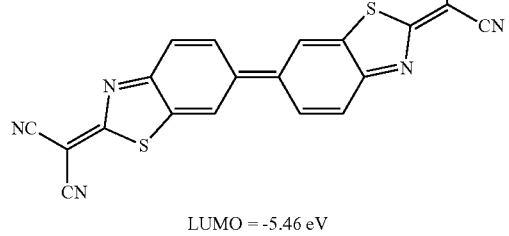
LUMO = -5.46 eV
XIX-33
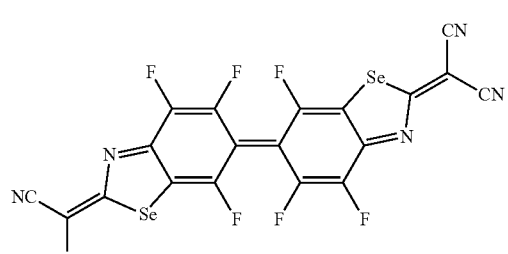
LUMO = -6.00 eV
XIX-34
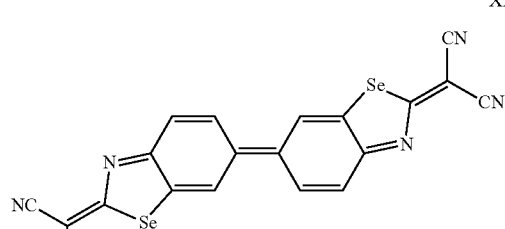
LUMO = -5.42 eV
XIX-49
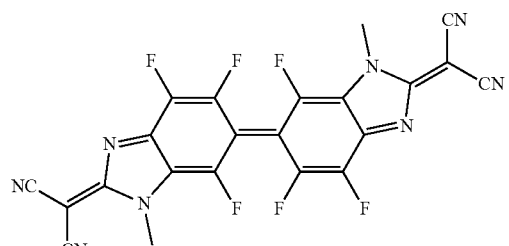
LUMO = -5.69 eV -continued

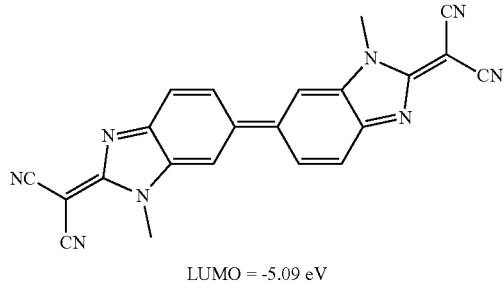

XIX-50

LUMO = -5.09 eV

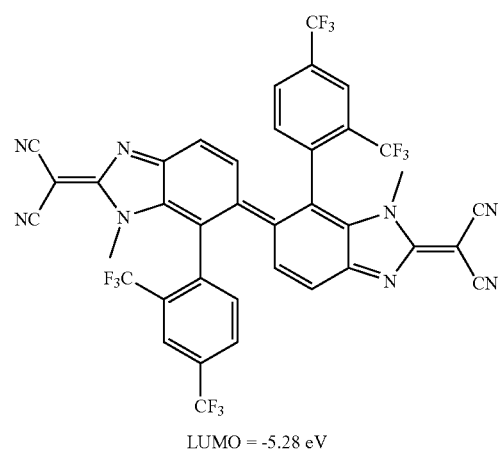

XIX-60

LUMO = -5.28 eV

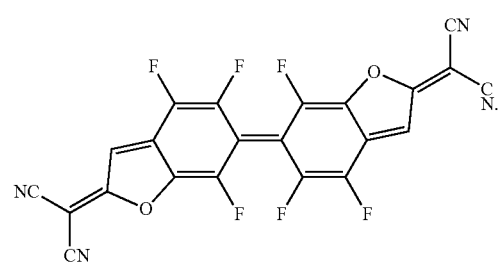

XIX-65

LUMO = -5.62 eV

In order to further prove the deep LUMO property of the compounds disclosed in the present disclosure, Compound III-12 was synthesized, and its LUMO energy level was tested.

MATERIAL SYNTHESIS EXAMPLE

The method for preparing a compound in the present disclosure is not limited herein. Typically, the following compounds are taken as examples without limitations, and synthesis routes and preparation methods thereof are described below:

Step 1: Synthesis of Intermediate III-12-A

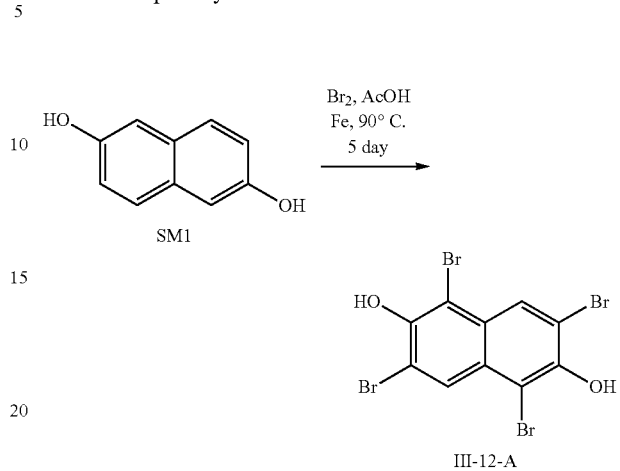

To a 2 L two-necked round bottom flask, the SM1 (29.2 g, 182 mmol), AcOH (900 mL), $Br_2$ (116.7 g, 729 mmol) and Fe powder (1.17 g, 21 mmol) were added sequentially. The reaction was reacted for 24 h at 90° C. and cooled to room temperature. Then, bromine (116.7 g, 729 mmol) was added additionally to the mixture and reacted continually for 3 days at 90° C. After the completion, the reaction was cooled with an ice bath. The reaction solution was poured into $H_2O$ (3 L) and filtered to give the crude product. The crude product was purified by being slurried in n-heptane: MTBE (methyl tert-butyl ether)=10:1, and filtered to obtain a black solid of intermediate III-12-A (40 g, yield of 46%).

Step 2: Synthesis of Intermediate III-12-B

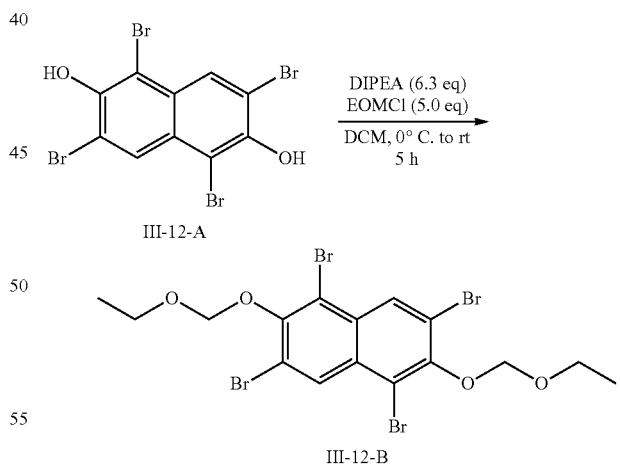

To a 250 mL two-necked round bottom flask, the intermediate III-12-A (35 g, 73.6 mmol), DCM (350 mL) and DIPEA (diisopropylethylamine, 60 g, 464 mmol) were added sequentially. The mixture was cooled in an ice bath. EOMCl (chloromethyl ethyl ether, 34.8 g, 368 mmol) was added dropwisely to the mixture and reacted for 2-3 h at room temperature. After the completion monitored with TLC, the reaction solution was added with $H_2O$ (100 mL), extracted with DCM and concentrated the organic phase.

The residue was purified via column chromatography to afford the intermediate III-12-B (34.4 g, yield of 79%) as a white solid.

Step 3: Synthesis of Intermediate III-12-C

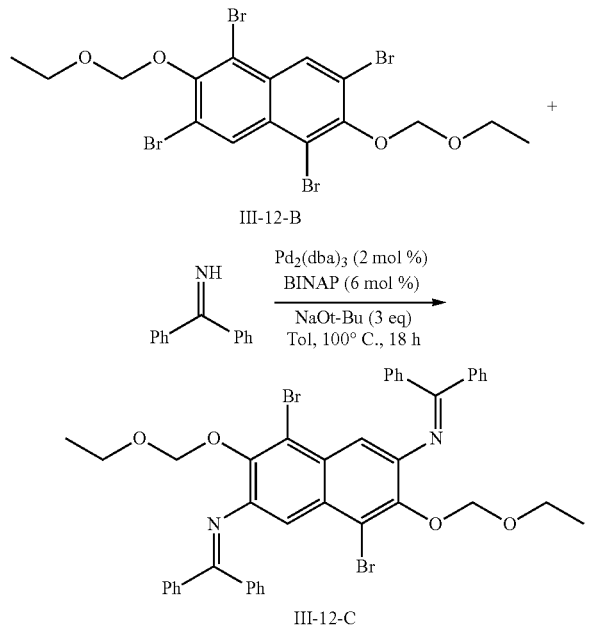

To a 2 L two-necked round bottom flask, the intermediate III-12-B (27 g, 45.61 mmol), NaOt-Bu (13.23 g, 137.7 mmol), Pd$_2$(dba)$_3$ (810 mg, 0.8845 mmol) and BINAP (2,2'-Bis(diphenylphosphino)-1,1'-binaphthyl, 1.7 g, 2.730 mmol) were added sequentially. Then, the gas of reaction flask was replaced with nitrogen for three times, the mixture was added with degassed toluene (1 L) and benzophenone imine (20.52 g, 114.04 mmol), reacted for 18 h at 100° C. The mixture was cooled to room temperature, filtered through a silica gel layer. The silica gel layer was washed with dichloromethane, and the filtrate was concentrated and filtered to obtain a crude product. The crude product was purified by being slurried in 500 mL of methanol at 60° C. for 1 h, and filtered to obtain a yellow solid III-12-C (31 g, yield of 86%).

Step 4: Synthesis of Intermediate III-12-D

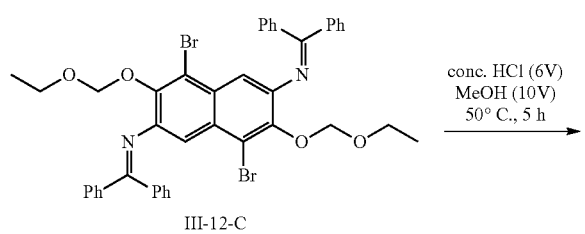

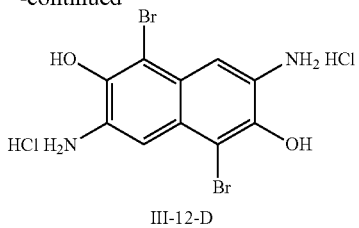

Intermediate III-12-C (31 g, 39.11 mmol) was added to a 1 L two-necked round bottom flask, and the gas of reaction flask was replaced with nitrogen for three times. MeOH (300 mL) and conc. HCl (180 mL) were added to the reaction flask, and the reaction was reacted for 6 h at 50° C. After the completion monitored with TLC, the reaction solution was filtered to afford the intermediate III-12-D (16 g, yield of 100%) as a white solid.

Step 5: Synthesis of Intermediate III-12-E

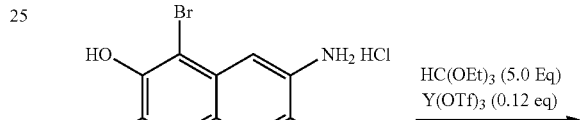

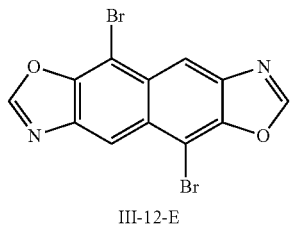

To a 1 L two-necked round bottom flask, the intermediate III-12-D (15 g, 35.64 mmol) and Y(OTf)$_3$ (2.3 g, 4.29 mmol) were added. Then, the gas of reaction flask was replaced with nitrogen for three times, the mixture was added with degassed DMSO (150 mL) and HC(OEt)$_3$ (26.4 g, 178.2 mmol), and reacted for 6 h at 120° C. The mixture was cooled to room temperature, washed with 300 mL of mixed solvents of n-heptane and dichloromethane (1:1, v/v), and then the mixture was filtered to obtain light brown solid intermediate III-12-E (10.1 g, yield of 77%).

Step 6: Synthesis of Intermediate III-12-F

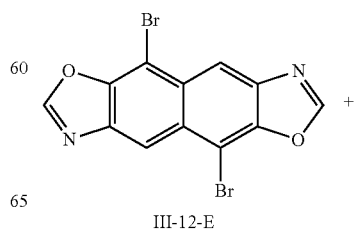

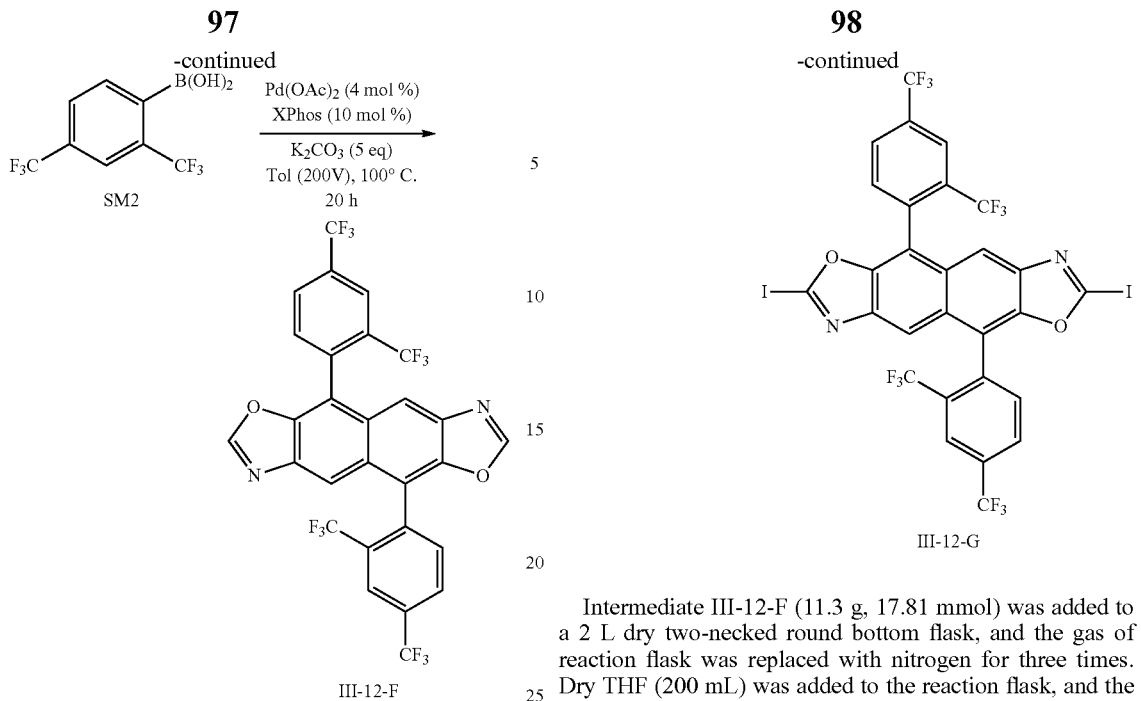

To a 2 L two-necked round bottom flask, the intermediate III-12-E (5 g, 13.59 mmol), SM2 (14.02 g, 54.36 mmol), K$_2$CO$_3$ (9.4 g, 67.95 mmol), Pd(OAc)$_2$ (122 mg, 0.554 mmol) and XPhos (650 mg, 1.36 mmol) were added sequentially. Then, the gas of reaction flask was replaced with nitrogen for three times, the mixture was added with degassed toluene (1 L), warmed to 100° C. and reacted for 20 h. After the completion, the mixture was cooled to room temperature, filtered through a silica gel layer. The silica gel layer was washed with dichloromethane, and the filtrate was concentrated and purified via column chromatography to afford the intermediate III-12-F (12.3 g, yield of 71%) as a white solid. $^1$H NMR (400 MHz, Chloroform-d) δ 8.25 (s, 2H), 8.13 (s, 2H), 8.10-8.02 (m, 2H), 7.88 (s, 2H), 7.73 (d, J=7.9 Hz, 2H).

Step 7: Synthesis of Intermediate III-12-G

Intermediate III-12-F (11.3 g, 17.81 mmol) was added to a 2 L dry two-necked round bottom flask, and the gas of reaction flask was replaced with nitrogen for three times. Dry THF (200 mL) was added to the reaction flask, and the reaction was cooled to −20~−10° C. with dry ice/ethanol bath. TMPMgCl LiCl (2,2,6,6-Tetramethylpiperidinylmagnesium chloride lithium chloride, 1.0 mol/L in THF, 54 mL, 54 mmol) was added to the mixture and the reaction was reacted for 1 h at the same temperature. Then, I$_2$ (18.08 g, 71.25 mmol) was added to the reaction mixture and stirring was continued for 1 h. After the completion monitored with TLC, the mixture was added with saturated Na$_2$SO$_3$ solution, extracted with EA and the organic phase was concentrated. The residue was purified via column chromatography to afford the intermediate III-12-G (11.4 g, yield of 72%) as a white solid. $^1$H NMR (400 MHz, Chloroform-d) δ 8.24 (s, 2H), 8.06 (dd, J=8.3, 1.8 Hz, 2H), 7.72 (s, 2H), 7.69 (d, J=8.0 Hz, 2H).

Step 8: Synthesis of Intermediate III-12-H

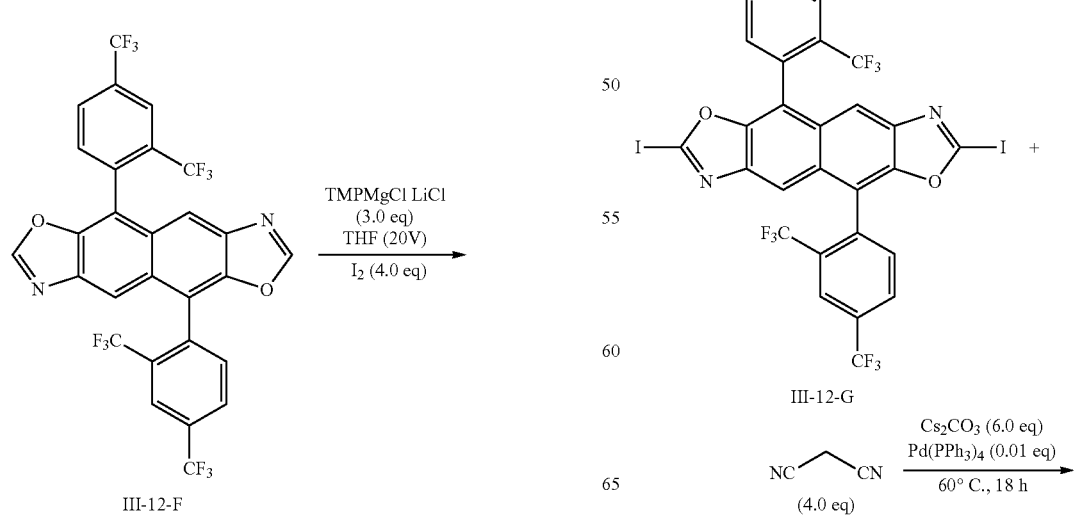

-continued

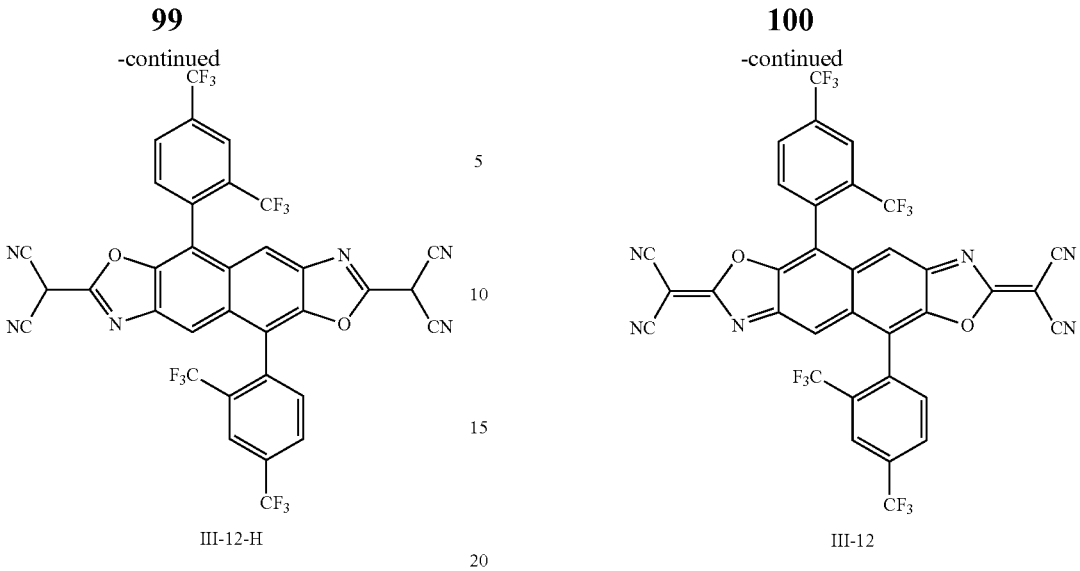

III-12-H

III-12

To a 500 mL dry two-necked round bottom flask, the intermediate III-12-G (4.3 g, 4.852 mmol), malononitrile (1.28 g, 19.41 mmol), $Cs_2CO_3$ (9.48 g, 29.11 mmol) and $Pd(PPh_3)_4$ (56 mg, 0.0485 mmol) were added sequentially. Then, the gas of reaction flask was replaced with nitrogen for three times. The mixture was added with DMAc (N,N-dimethylacetamide, 60 mL), warmed to 60° C. and reacted for 18 h. After the completion monitored with HPLC, the reaction system was cooled to room temperature. HCl (2 N, 50 mL) and $H_2O$ (100 mL) were added to the mixture, and then a large amount of solid was precipitated and the solid was obtained by filtration. The solid was washed with $H_2O$, slurried with MeCN (100 mL) at 60° C. for 18 h, and the mixture was filtered to obtain a white solid. The white solid was purified by being slurried in DCM (100 mL) at 40° C. for 2 h and filtered to obtain the intermediate III-12-H (3.42 g, yield of 92%) as a white solid. $^1H$ NMR (400 MHz, DMSO-$d_6$) δ 8.39 (s, 2H), 8.32 (dd, J=8.2, 1.9 Hz, 2H), 7.93 (d, J=8.0 Hz, 2H), 6.87 (s, 2H).

Step 9: Synthesis of Compound III-12

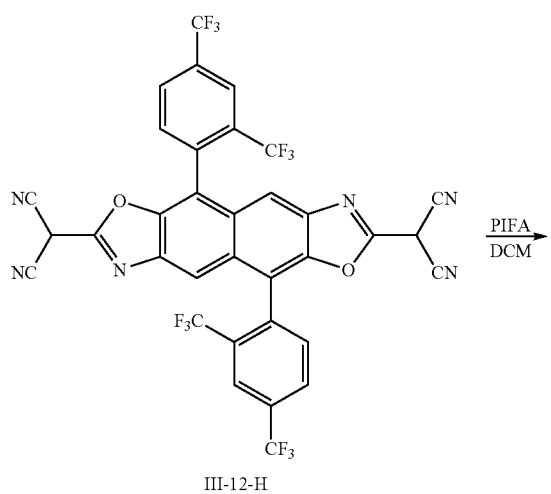

III-12-H

To a 500 mL dry single-necked round bottom flask, the intermediate III-12-H (5 g, 6.558 mmol), DCM (125 mL) and PIFA (4.23 g, 9.836 mmol) were added sequentially. The reaction was reacted for 3 days and filtered directly to give a black solid. The black solid was washed twice with DCM to afford the Compound III-12 (3 g, yield of 60%) as a black solid. $^1H$ NMR (400 MHz, Acetone-$d_6$) δ 8.43 (s, 2H), 8.37 (d, J=9.0 Hz, 2H), 8.00 (d, J=7.9 Hz, 2H), 7.31 (s, 2H).

The electrochemical property of the compounds of the present disclosure was tested via cyclic voltammetry (CV method). The test uses the electrochemical workstation model CorrTest CS120 produced by WUHAN CORRTEST Instrument Co., Ltd., and used three electrode working system: platinum disk electrode as working electrode, Ag/$AgNO_3$ electrode as reference electrode, platinum wire electrode as auxiliary electrode. Using anhydrous DCM or anhydrous DMF as the solvent and 0.1 mol/L tetrabutylammonium hexafluorophosphate as the supporting electrolyte, the target compound was prepared into a $10^{-3}$ mol/L solution, and nitrogen gas was bubbled into the solution for 10 min deoxygenation before the test. Instrument parameter settings: the scan rate is 100 mV/s, the potential interval is 0.5 mV, and the test scope is from 1 V to −0.5 V.

The LUMO values of selected compound of the present disclosure is tested via CV method. The LUMO energy level of the Compound III-12 tested via the CV method in anhydrous DCM is −5.21 eV. Using the same CV method, the LUMO energy level of the commercial hole injection layer material HATCN in anhydrous DCM is −4.33 eV, the LUMO energy level of the commercial p-dopant material $F_4$-TCNQ in anhydrous DCM is −4.95 eV, and the LUMO energy level of NDP-9 in anhydrous DCM is −5.03 eV. The structures of HATCN, $F_4$-TCNQ and NDP-9 are shown as below:

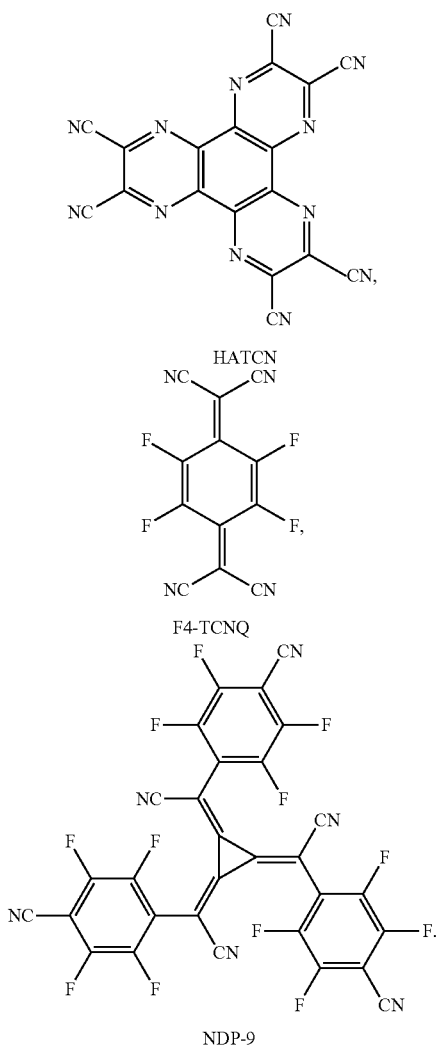

By comparison, it can be seen that the LUMO energy level of Compound III-12 is 0.9 eV deeper than HATCN, and is 0.3 eV deeper than F4-TCNQ, and is 0.2 eV deeper than commercial p-dopant material NDP-9, so it is certain that Compound III-12 has extremely electron-deficient property and it is an excellent electron acceptor material and charge transfer material. These data also show that Compound III-12 has greater potential and excellent application prospects in electroluminescent devices, whether as a hole injection layer material or a p-dopant material.

The difference between the tested LUMO value (−5.21 eV) and the LUMO value calculated by DFT (−5.60 eV) of the Compound III-12 of the present disclosure is 0.4 eV. The difference between tested LUMO value (−4.33 eV) and the LUMO value calculated by DFT (−4.80 eV) of HATCN is 0.47 eV. The difference between the tested LUMO value (−4.94 eV) and the LUMO value calculated by DFT (−5.50 eV) of F4-TCNQ is 0.56 eV. The difference between the tested LUMO value (−5.03 eV) and the LUMO value calculated by DFT (−5.49 eV) of NDP-9 is 0.45 eV. Based on the above comparison, it can be seen that for compounds with different skeletons, the difference between the tested data by CV method and the calculated data by DFT is about 0.5 eV, which shows that the DFT calculation results have high reference value. According to the aforementioned DFT calculation results of the compounds of the present disclosure, it can be seen that the compounds of the present disclosure have very deep LUMO energy level, so they are excellent electron acceptor materials and charge transfer materials. They also have the potential to be excellent hole injection materials and p-dopant materials, and have very broad industrial application prospects.

It is understood that the various embodiments described herein are by way of example only, and are not intended to limit the scope of the invention. The present disclosure as claimed may therefore include variations from the particular examples and preferred embodiments described herein, as will be apparent to one of skill in the art. Many of the materials and structures described herein may be substituted with other materials and structures without deviating from the spirit of the invention. It is understood that various theories as to why the invention works are not intended to be limited.

The invention claimed is:

1. A compound having a structure of B(A)$_2$, wherein A has a structure of Formula 1:

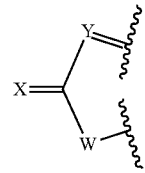

Formula 1 wherein,

X is, at each occurrence identically or differently, selected from the group consisting of O, S, Se, NR' and CR"R'";

Y is N;

W is, at each occurrence identically or differently, selected from the group consisting of O, S, Se and NR$_N$;

wherein, B is selected from a substituted or unsubstituted conjugated unsaturated fused aryl ring having 10 to 30 ring atoms, or a substituted or unsubstituted conjugated unsaturated fused heteroaryl ring having 10 to 30 ring atoms, or selected from the structure represented by one of Formula 2 to Formula 8, or combinations thereof:

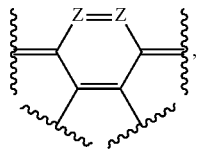

Formula 2

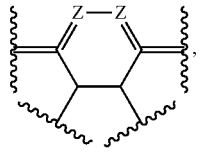

Formula 3

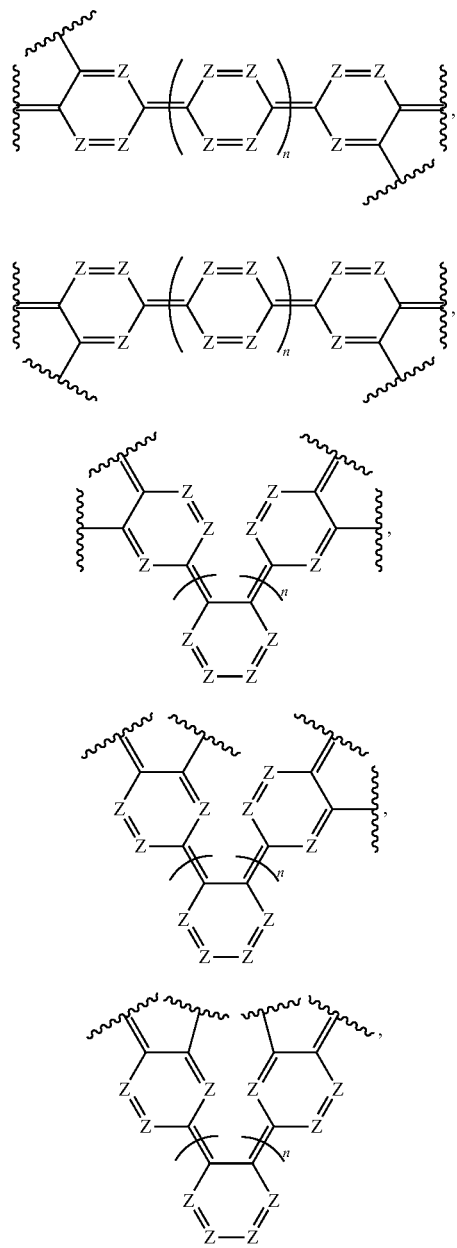

Formula 4

Formula 5

Formula 6

Formula 7

Formula 8 wherein B is fused with each of A through a single bond and a double bond;

wherein Z is, at each occurrence, identically or differently, selected from the group consisting of CR and N;

n is, at each occurrence, identically or differently, selected from 0, 1, or 2;

wherein, R, R', R", R'" and $R_N$ are, at each occurrence, identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, sulfanyl, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein at least one of R, R', R", R'" and $R_N$ is a group having at least one electron-withdrawing group;

any two adjacent substituents R, R', R", R'" and $R_N$ can be optionally joined to form a ring.

2. The compound according to claim 1, wherein when B is selected from Formula 2 or Formula 3, the compound is selected from the structure of Formula I or Formula II:

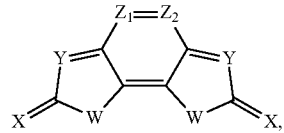

Formula I

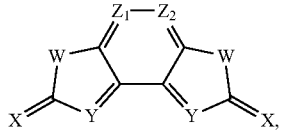

Formula II wherein, $Z_1$ and $Z_2$ are, at each occurrence identically or differently, selected from the group consisting of CR and N;

wherein, X is, at each occurrence identically or differently, selected from the group consisting of O, S, Se, NR' and CR"R'";

wherein, Y is N;

wherein, W is, at each occurrence identically or differently, selected from the group consisting of O, S, Se and $NR_N$;

wherein, R, R', R", R'" and $R_N$ are, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, sulfanyl, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein at least one of R, R', R", R'" and $R_N$ is a group having at least one electron-withdrawing group; and any two adjacent substituents R, R', R", R'" and $R_N$ can be optionally joined to form a ring;

or wherein when B is selected from a substituted or unsubstituted conjugated unsaturated fused aryl ring having 10 to 30 ring atoms, or a substituted or unsubstituted conjugated unsaturated fused heteroaryl ring having 10 to 30 ring atoms, the compound is selected from the structure of any one of Formula III to Formula XVIII:

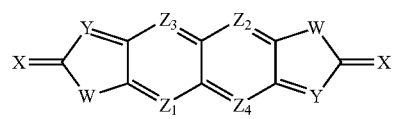

Formula III

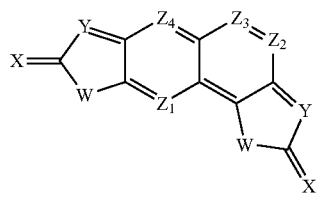

Formula IV

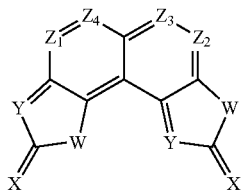

Formula V

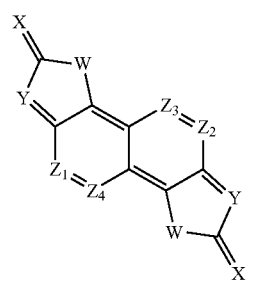

Formula VI

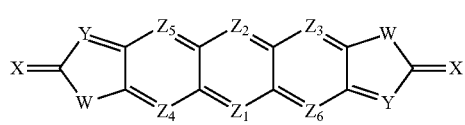

Formula VII

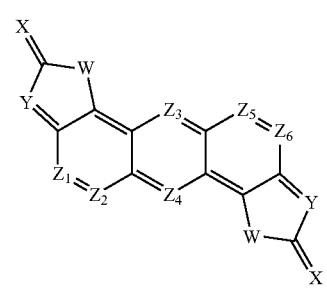

Formula VIII

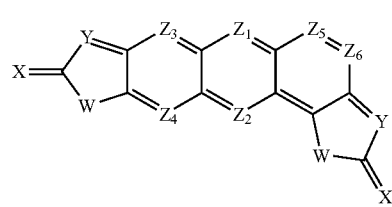

Formula IX

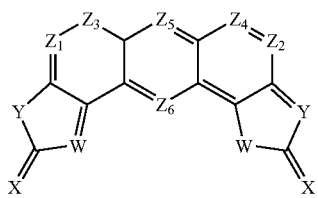

Formula X

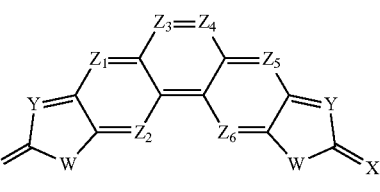

Formula XI

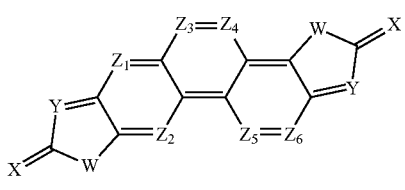

Formula XII

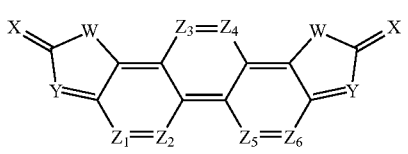

Formula XIII

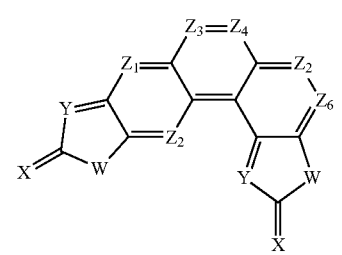

Formula XIV

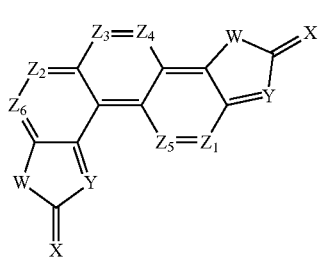

Formula XV

Formula XVI

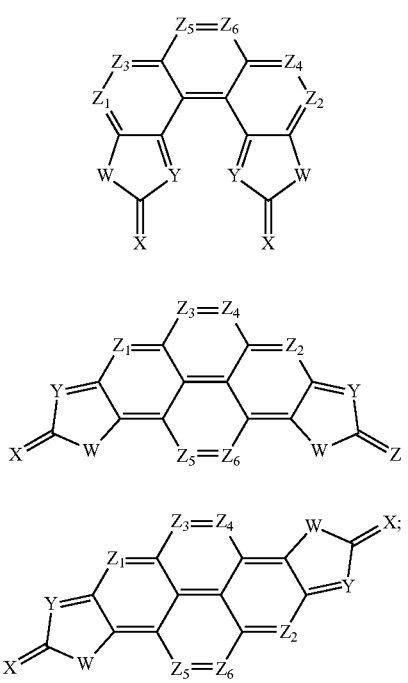

Formula XVII

Formula XVIII wherein,
X is, at each occurrence identically or differently, selected from the group consisting of O, S, Se, NR' and CR"R'";
Y is N;
W is, at each occurrence identically or differently, selected from the group consisting of O, S, Se and $NR_N$;
wherein $Z_1$ to $Z_6$ are, at each occurrence identically or differently, selected from the group consisting of CR and N;
wherein, R, R', R", R'" and $R_N$ are, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, sulfanyl, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;
wherein at least one of R, R', R", R'" and $R_N$ is a group having at least one electron-withdrawing group;
any two adjacent substituents R, R', R", R'" and $R_N$ can be optionally joined to form a ring;
or wherein when B is selected from Formula 4 to Formula 8, n is 0 or 1, and the compound has the structure of any one of Formula XIX to Formula XXIV:

Formula XIX

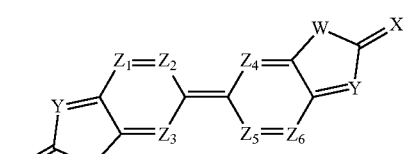

Formula XX

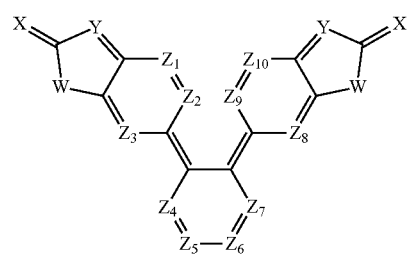

Formula XXI

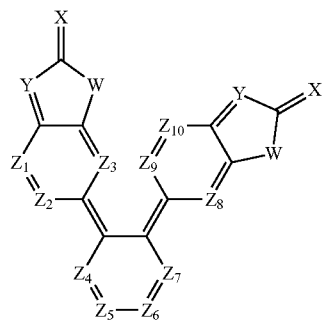

Formula XXII

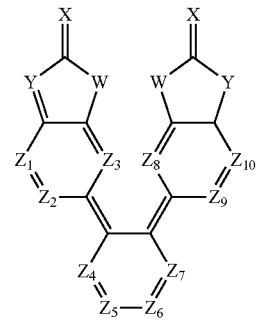

Formula XXIII

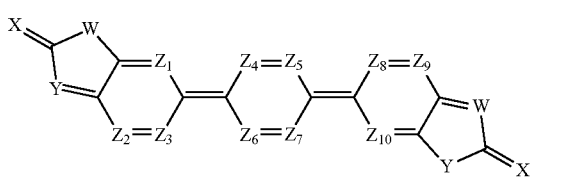

Formula XXIV

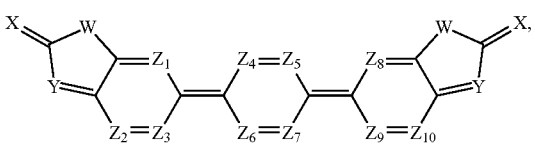

wherein,
X is, at each occurrence identically or differently, selected from the group consisting of O, S, Se, NR' and CR"R'";
Y is N;
W is, at each occurrence identically or differently, selected from the group consisting of O, S, Se and $NR_N$;

wherein $Z_1$ to $Z_{10}$ are, at each occurrence identically or differently, selected from the group consisting of CR and N;

wherein, R, R', R", R"', and $R_N$ are, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, sulfanyl, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein at least one of R, R', R", R"' and $R_N$ is a group having at least one electron-withdrawing group; and any two adjacent substituents R, R', R", R"' and $R_N$ can be optionally joined to form a ring.

3. The compound according to claim 1, wherein X is, at each occurrence identically or differently, selected from S, Se, NR' or CR"R"'.

4. The compound according to claim 1, wherein W is, at each occurrence identically or differently, selected from O, S or Se.

5. The compound according to claim 1, wherein W is, at each occurrence identically or differently, selected from $NR_N$, $R_N$ is, at each occurrence identically or differently, selected from the group consisting of a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof.

6. The compound according to claim 1, wherein at least one of Z is selected from N.

7. The compound according to claim 2, wherein in the Formula I to Formula XXII, at least one of $Z_1$ to $Z_x$ is selected from N, x in $Z_x$ corresponds to the largest number of Z existing in Formula I to Formula XXII.

8. The compound according to claim 1, wherein Z is, at each occurrence identically or differently, selected from CR.

9. The compound according to claim 1, wherein at least one of R, R', R" and R"' is the group having at least one electron-withdrawing group.

10. The compound according to claim 1, wherein the Hammett's constant of the electron-withdrawing group is ≥0.05.

11. The compound according to claim 1, wherein the electron-withdrawing group is selected from the group consisting of halogen, nitroso, nitro, acyl, carbonyl, a carboxylic acid group, an ester group, cyano, isocyano, SCN, OCN, $SF_5$, boranyl, sulfinyl, sulfonyl, phosphoroso, an aza-aromatic ring group, or is any one of an alkyl group having 1 to 20 carbon atoms, a cycloalkyl group having 3 to 20 ring carbon atoms, a heteroalkyl group having 1 to 20 carbon atoms, an arylalkyl group having 7 to 30 carbon atoms, an alkoxyl group having 1 to 20 carbon atoms, an aryloxy group having 6 to 30 carbon atoms, an alkenyl group having 2 to 20 carbon atoms, an alkynyl group having 2 to 20 carbon atoms, an aryl group having 6 to 30 carbon atoms, a heteroaryl group having 3 to 30 carbon atoms, an alkylsilyl group having 3 to 20 carbon atoms and an arylsilyl group having 6 to 20 carbon atoms which are substituted with one or more of halogen, nitroso, nitro, acyl, carbonyl, carboxylic acid group, ester group, cyano, isocyano, SCN, OCN, $SF_5$, boranyl, sulfinyl, sulfonyl, phosphoroso, aza-aromatic ring group, and combinations thereof.

12. The compound according to claim 2, wherein X is, at each occurrence identically or differently, selected from the group consisting of the following structures:

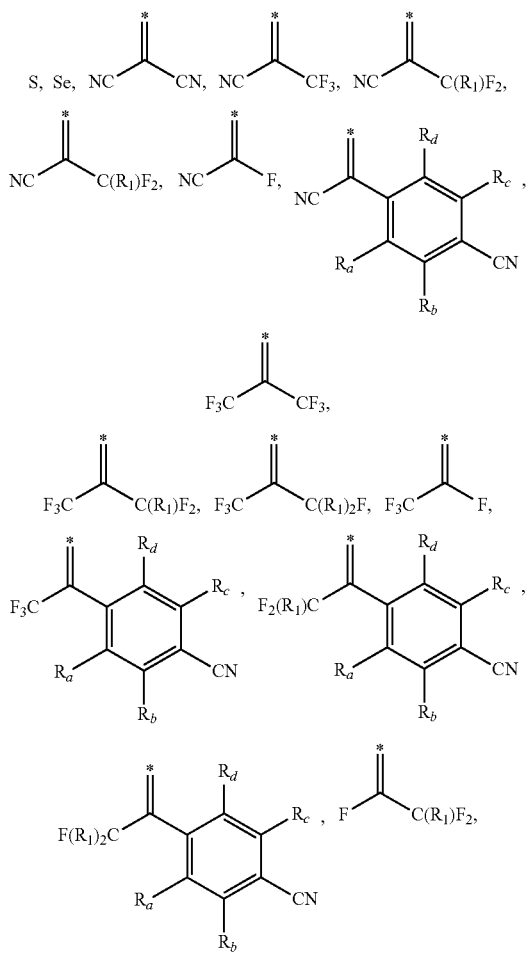

-continued

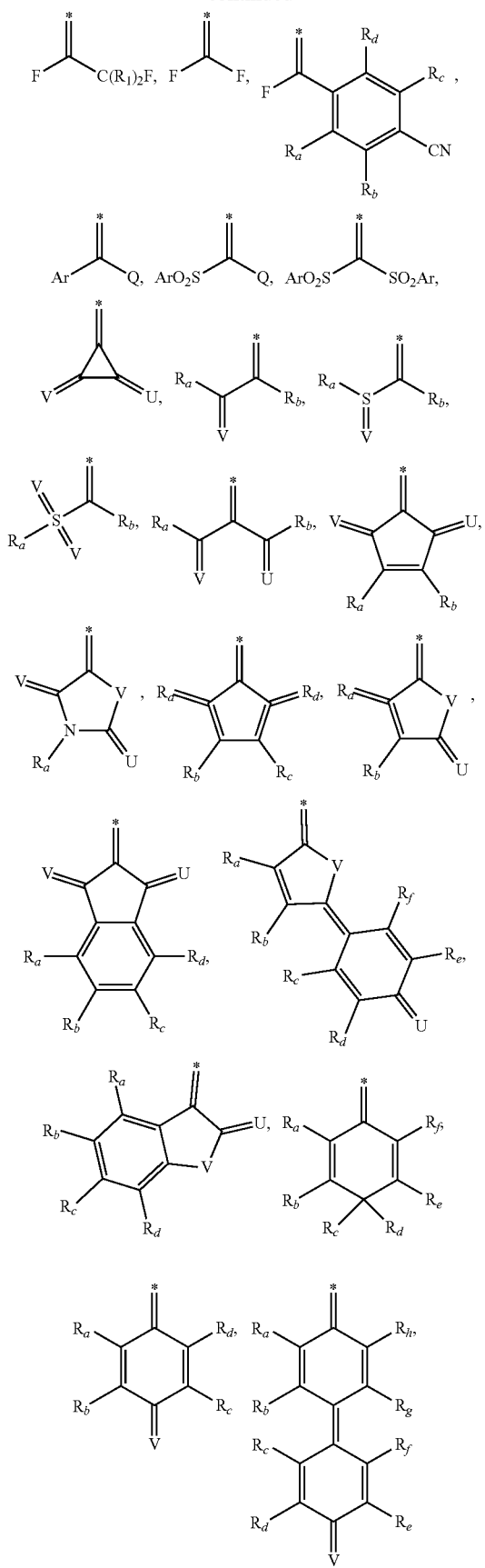

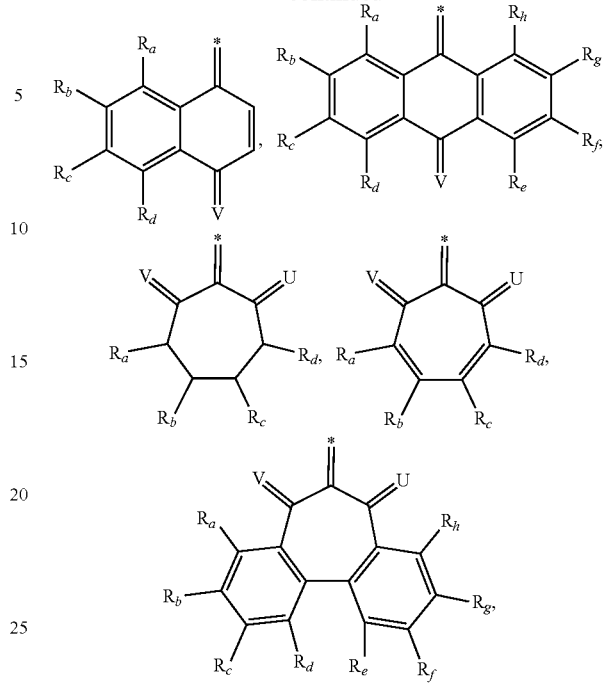

wherein R₁ is selected, at each occurrence, identically or differently, from the group consisting of hydrogen, deuterium, halogen, nitroso, nitro, acyl, carbonyl, a carboxylic acid group, an ester group, cyano, isocyano, SCN, OCN, SF₅, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein V and U are selected, at each occurrence, identically or differently, from the group consisting of $CR_xR_u$, $NR_v$, O, S and Se;

wherein Ar is selected, at each occurrence, identically or differently, from a substituted or unsubstituted aryl group having 6 to 30 carbon atoms, and a substituted or unsubstituted heteroaryl group having 3 to 30 carbon atoms;

wherein Q, $R_a$, $R_b$, $R_c$, $R_d$, $R_e$, $R_f$, $R_g$, $R_h$, $R_v$ and $R_u$ are selected, at each occurrence, identically or differently, from the group consisting of hydrogen, deuterium, halogen, nitroso, nitro, acyl, carbonyl, a carboxylic acid group, an ester group, cyano, isocyano, SCN, OCN, SF₅, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein Q is a group having at least one electron-withdrawing group, and for any one of the structures, when one or more of $R_a$, $R_b$, $R_c$, $R_d$, $R_e$, $R_f$, $R_g$, $R_h$, $R_v$ and $R_u$ is(are) appear, at least one of $R_a$, $R_b$, $R_c$, $R_d$, $R_e$, $R_f$, $R_g$, $R_h$, $R_v$ and $R_u$ is a group having at least one electron-withdrawing group.

13. The compound according to claim 2, wherein X is, at each occurrence identically or differently, selected from the group consisting of:

A1

S, Se, NC CN,

A2

A3

A4

A5

NC SCN,

A6

NC CF₃,

A7

14. The compound according to claim 13, wherein R is, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, sulfanyl, an unsubstituted alkyl group having 1 to 20 carbon atoms, an unsubstituted cycloalkyl group having 3 to 20 ring carbon atoms, an unsubstituted alkoxyl group having 1 to 20 carbon atoms, an unsubstituted alkenyl group having 2 to 20 carbon atoms, an unsubstituted aryl group having 6 to 30 carbon atoms, and an unsubstituted heteroaryl group having 3 to 30 carbon atoms, and any one of an alkyl group having 1 to 20 carbon atoms, a cycloalkyl group having 3 to 20 ring carbon atoms, an alkoxyl group having 1 to 20 carbon atoms, an alkenyl group having 2 to 20 carbon atoms, an aryl group having 6 to 30 carbon atoms and a heteroaryl group having 3 to 30 carbon atoms which are substituted with one or more groups selected from the group consisting of halogen, nitroso, nitro, acyl, carbonyl, a carboxylic acid group, an ester group, cyano, isocyano, SCN, OCN, $SF_5$, boranyl, sulfinyl, sulfonyl, phosphoroso, and combinations thereof.

15. The compound according to claim 13, wherein R is, at each occurrence identically or differently, selected from the group consisting of:

B1

F—

B2

—CF₃

B3

—OCF₃

B4

—C₂F₅

B5

—OC₂F₅

B6

—CN

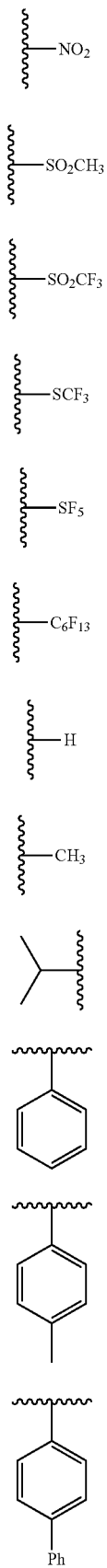
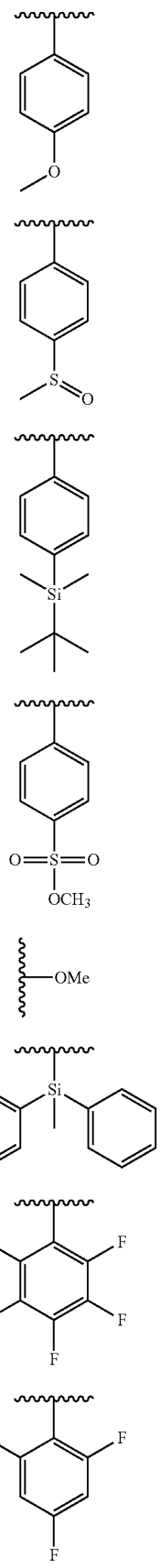

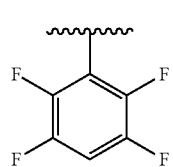 B27
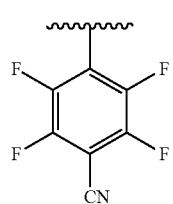 B28
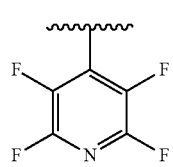 B29
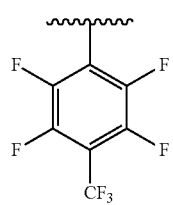 B30
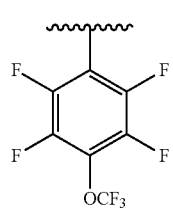 B31
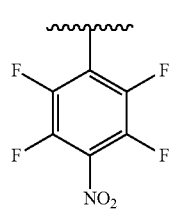 B32
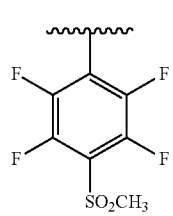 B33
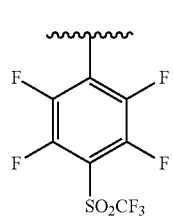 B34
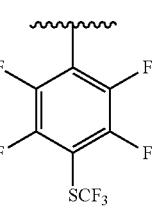 B35
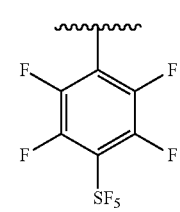 B36
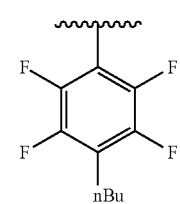 B37
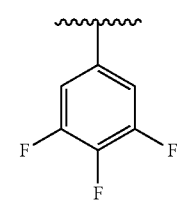 B38
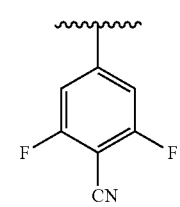 B39
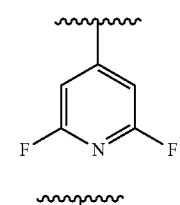 B40
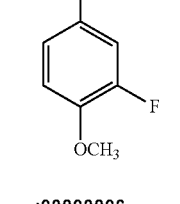 B41
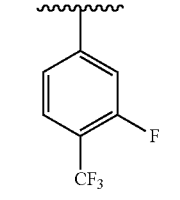 B42

-continued
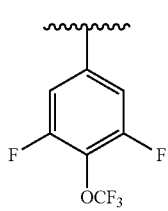 B43
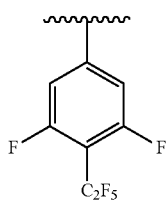 B44
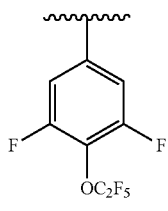 B45
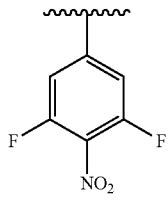 B46
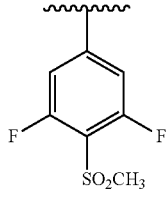 B47
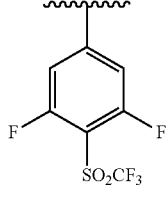 B48
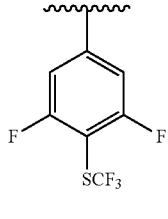 B49
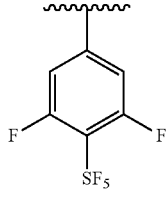 B50
-continued
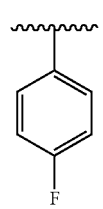 B51
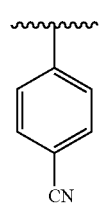 B52
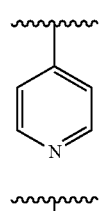 B53
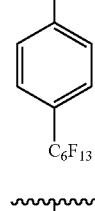 B54
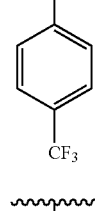 B55
 B56
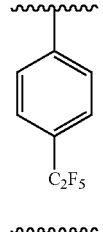 B57
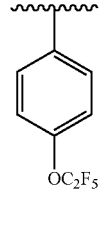 B58

-continued
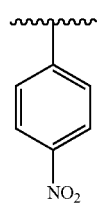 B59
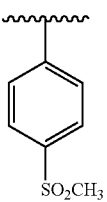 B60
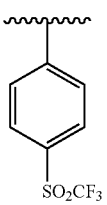 B61
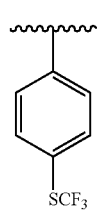 B62
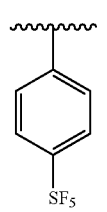 B63
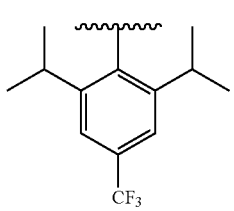 B64
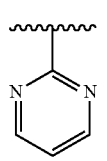 B65
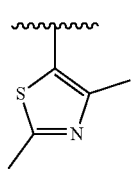 B66
-continued
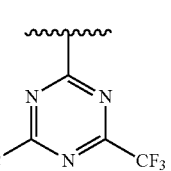 B67
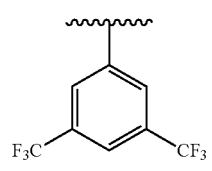 B68
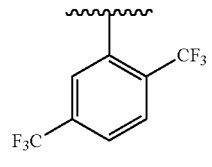 B69
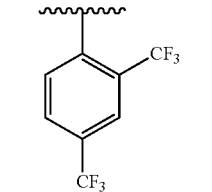 B70
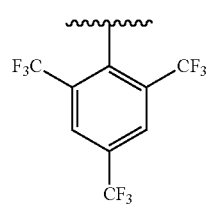 B71
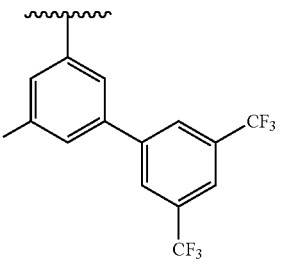 B72
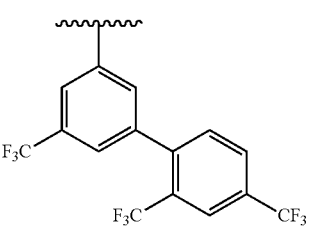 B73

-continued
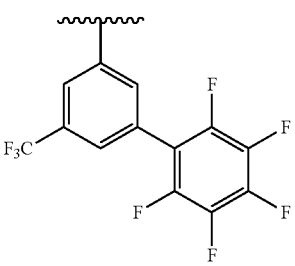 B74
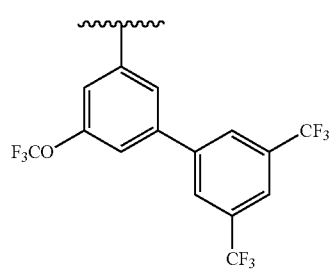 B75
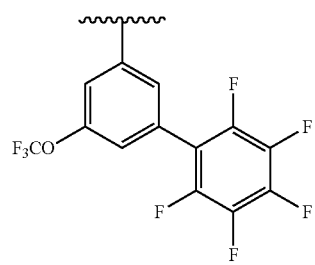 B76
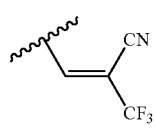 B77
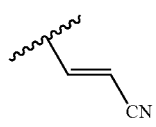 B78
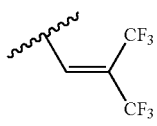 B79
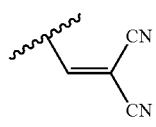 B80
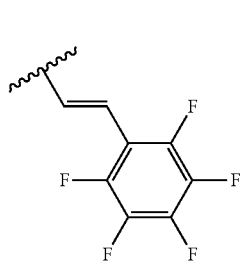 B81
-continued
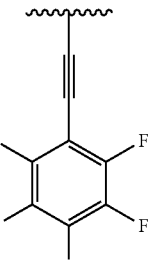 B82
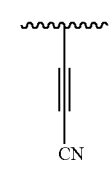 B83
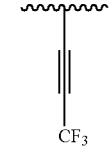 B84
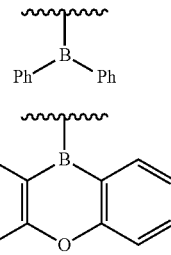 B85
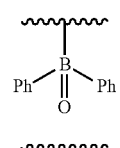 B86
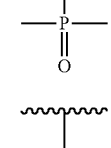 B87
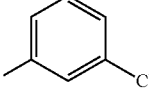 B88
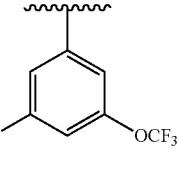 B89
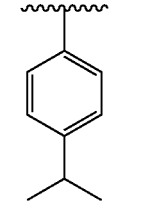 B90
B91

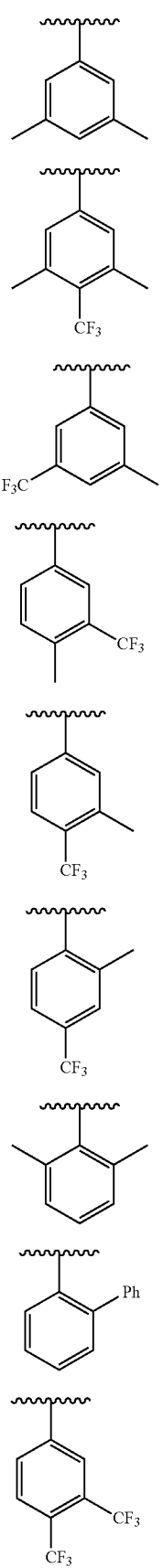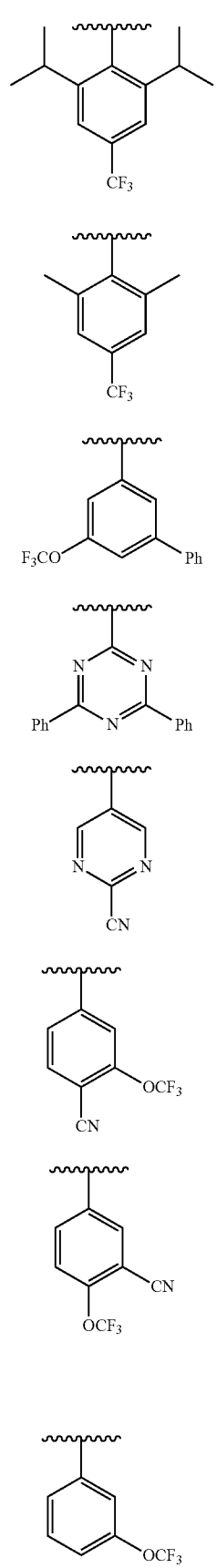

-continued

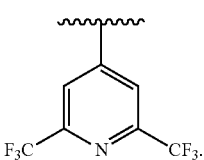
B109

16. The compound according to claim 15, wherein the compound is selected from the group consisting of Compound I-1 to Compound I-64, Compound II-1 to Compound II-64, Compound III-1 to Compound III-64, Compound IV-1 to Compound IV-64, Compound V-1 to Compound V-64, Compound VI-1 to Compound VI-64, Compound VII-1 to Compound VII-64, Compound VIII-1 to Compound VIII-64, Compound IX-1 to Compound IX-64, Compound X-1 to Compound X-64, Compound XI-1 to Compound XI-64, Compound XII-1 to Compound XII-64, Compound XIII-1 to Compound XIII-64, Compound XIV-1 to Compound XIV-64, Compound XV-1 to Compound XV-64, Compound XVI-1 to Compound XVI-64, Compound XVII-1 to Compound XVII-64, Compound XVIII-1 to Compound XVIII-64, Compound XIX-1 to Compound XIX-64:

wherein, Compound I-1 to Compound I-64 have the structure of Formula I:

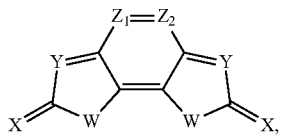

Formula I in Formula I, both of X are the same, both of Y are the same, both of W are the same, $Z_1$ and $Z_2$ are the same, and X, Y, W, $Z_1$ and $Z_2$ are correspondingly selected from the atoms or groups as shown in the following table:

| No. | X | Y | W | $Z_1 = Z_2$ | No. | X | Y | W | $Z_1 = Z_2$ |
|---|---|---|---|---|---|---|---|---|---|
| I-1 | A1 | N | O | C-B1 | I-2 | A1 | N | O | C-B13 |
| I-3 | A1 | N | O | C-B16 | I-4 | A1 | N | O | C-B17 |
| I-5 | A1 | N | O | C-B25 | I-6 | A1 | N | O | C-B52 |
| I-7 | A1 | N | O | C-B54 | I-8 | A1 | N | O | C-B55 |
| I-9 | A1 | N | O | C-B63 | I-10 | A1 | N | O | C-B68 |
| I-11 | A1 | N | O | C-B69 | I-12 | A1 | N | O | C-B70 |
| I-13 | A1 | N | O | C-B71 | I-14 | A1 | N | O | C-B89 |
| I-15 | A1 | N | O | C-B90 | I-16 | A1 | N | O | C-B91 |
| I-17 | A1 | N | S | C-B1 | I-18 | A1 | N | S | C-B13 |
| I-19 | A1 | N | S | C-B16 | I-20 | A1 | N | S | C-B17 |
| I-21 | A1 | N | S | C-B25 | I-22 | A1 | N | S | C-B52 |
| I-23 | A1 | N | S | C-B54 | I-24 | A1 | N | S | C-B55 |
| I-25 | A1 | N | S | C-B63 | I-26 | A1 | N | S | C-B68 |
| I-27 | A1 | N | S | C-B69 | I-28 | A1 | N | S | C-B70 |
| I-29 | A1 | N | S | C-B71 | I-30 | A1 | N | S | C-B89 |
| I-31 | A1 | N | S | C-B90 | I-32 | A1 | N | S | C-B91 |
| I-33 | A1 | N | Se | C-B1 | I-34 | A1 | N | Se | C-B13 |
| I-35 | A1 | N | Se | C-B16 | I-36 | A1 | N | Se | C-B17 |
| I-37 | A1 | N | Se | C-B25 | I-38 | A1 | N | Se | C-B52 |
| I-39 | A1 | N | Se | C-B54 | I-40 | A1 | N | Se | C-B55 |
| I-41 | A1 | N | Se | C-B63 | I-42 | A1 | N | Se | C-B68 |
| I-43 | A1 | N | Se | C-B69 | I-44 | A1 | N | Se | C-B70 |
| I-45 | A1 | N | Se | C-B71 | I-46 | A1 | N | Se | C-B89 |
| I-47 | A1 | N | Se | C-B90 | I-48 | A1 | N | Se | C-B91 |
| I-49 | A1 | N | NMe | C-B1 | I-50 | A1 | N | NMe | C-B13 |
| I-51 | A1 | N | NMe | C-B16 | I-52 | A1 | N | NMe | C-B17 |
| I-53 | A1 | N | NMe | C-B25 | I-54 | A1 | N | NMe | C-B52 |
| I-55 | A1 | N | NMe | C-B54 | I-56 | A1 | N | NMe | C-B55 |
| I-57 | A1 | N | NMe | C-B63 | I-58 | A1 | N | NMe | C-B68 |
| I-59 | A1 | N | NMe | C-B69 | I-60 | A1 | N | NMe | C-B70 |
| I-61 | A1 | N | NMe | C-B71 | I-62 | A1 | N | NMe | C-B89 |
| I-63 | A1 | N | NMe | C-B90 | I-64 | A1 | N | NMe | C-B91 | wherein, Compound II-1 to Compound II-64 have the structure of Formula II:

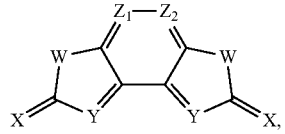

Formula II in Formula II, both of X are the same, both of Y are the same, both of W are the same, $Z_1$ and $Z_2$ are the same, and X, Y, W, $Z_1$ and $Z_2$ are correspondingly selected from the atoms or groups as shown in the following table:

| No. | X | Y | W | $Z_1 = Z_2$ | No. | X | Y | W | $Z_1 = Z_2$ |
|---|---|---|---|---|---|---|---|---|---|
| II-1 | A1 | N | O | C-B1 | II-2 | A1 | N | O | C-B13 |
| II-3 | A1 | N | O | C-B16 | II-4 | A1 | N | O | C-B17 |
| II-5 | A1 | N | O | C-B25 | II-6 | A1 | N | O | C-B52 |
| II-7 | A1 | N | O | C-B54 | II-8 | A1 | N | O | C-B55 |
| II-9 | A1 | N | O | C-B63 | II-10 | A1 | N | O | C-B68 |
| II-11 | A1 | N | O | C-B69 | II-12 | A1 | N | O | C-B70 |
| II-13 | A1 | N | O | C-B71 | II-14 | A1 | N | O | C-B89 |
| II-15 | A1 | N | O | C-B90 | II-16 | A1 | N | O | C-B91 |
| II-17 | A1 | N | S | C-B1 | II-18 | A1 | N | S | C-B13 |
| II-19 | A1 | N | S | C-B16 | II-20 | A1 | N | S | C-B17 |
| II-21 | A1 | N | S | C-B25 | II-22 | A1 | N | S | C-B52 |
| II-23 | A1 | N | S | C-B54 | II-24 | A1 | N | S | C-B55 |
| II-25 | A1 | N | S | C-B63 | II-26 | A1 | N | S | C-B68 |
| II-27 | A1 | N | S | C-B69 | II-28 | A1 | N | S | C-B70 |
| II-29 | A1 | N | S | C-B71 | II-30 | A1 | N | S | C-B89 |
| II-31 | A1 | N | S | C-B90 | II-32 | A1 | N | S | C-B91 |
| II-33 | A1 | N | Se | C-B1 | II-34 | A1 | N | Se | C-B13 |
| II-35 | A1 | N | Se | C-B16 | II-36 | A1 | N | Se | C-B17 |
| II-37 | A1 | N | Se | C-B25 | II-38 | A1 | N | Se | C-B52 |
| II-39 | A1 | N | Se | C-B54 | II-40 | A1 | N | Se | C-B55 |
| II-41 | A1 | N | Se | C-B63 | II-42 | A1 | N | Se | C-B68 |
| II-43 | A1 | N | Se | C-B69 | II-44 | A1 | N | Se | C-B70 |
| II-45 | A1 | N | Se | C-B71 | II-46 | A1 | N | Se | C-B89 |
| II-47 | A1 | N | Se | C-B90 | II-48 | A1 | N | Se | C-B91 |
| II-49 | A1 | N | NMe | C-B1 | II-50 | A1 | N | NMe | C-B13 |
| II-51 | A1 | N | NMe | C-B16 | II-52 | A1 | N | NMe | C-B17 |
| II-53 | A1 | N | NMe | C-B25 | II-54 | A1 | N | NMe | C-B52 |
| II-55 | A1 | N | NMe | C-B54 | II-56 | A1 | N | NMe | C-B55 |
| II-57 | A1 | N | NMe | C-B63 | II-58 | A1 | N | NMe | C-B68 |
| II-59 | A1 | N | NMe | C-B69 | II-60 | A1 | N | NMe | C-B70 |
| II-61 | A1 | N | NMe | C-B71 | II-62 | A1 | N | NMe | C-B89 |
| II-63 | A1 | N | NMe | C-B90 | II-64 | A1 | N | NMe | C-B91 | wherein, Compound III-1 to Compound III-64 have the structure of Formula III:

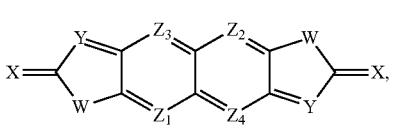

Formula III in Formula III, both of X are the same, both of Y are the same, both of W are the same, $Z_1$ and $Z_2$ are the same, $Z_3$ and $Z_4$ are the same, and X, Y, W, $Z_1$, $Z_2$, $Z_3$ and $Z_4$ are correspondingly selected from the atoms or groups as shown in the following table:

| No. | X | Y | W | $Z_1 = Z_2$ | $Z_3 = Z_4$ | No. | X | Y | W | $Z_1 = Z_2$ | $Z_3 = Z_4$ |
|---|---|---|---|---|---|---|---|---|---|---|---|
| III-1 | A1 | N | O | C-B1 | C-B1 | III-2 | A1 | N | O | C-B13 | C-B13 |
| III-3 | A1 | N | O | C-B16 | C-B13 | III-4 | A1 | N | O | C-B17 | C-B13 |
| III-5 | A1 | N | O | C-B25 | C-B13 | III-6 | A1 | N | O | C-B52 | C-B13 |
| III-7 | A1 | N | O | C-B54 | C-B13 | III-8 | A1 | N | O | C-B55 | C-B13 |
| III-9 | A1 | N | O | C-B63 | C-B13 | III-10 | A1 | N | O | C-B68 | C-B13 |
| III-11 | A1 | N | O | C-B69 | C-B13 | III-12 | A1 | N | O | C-B70 | C-B13 |
| III-13 | A1 | N | O | C-B71 | C-B13 | III-14 | A1 | N | O | C-B89 | C-B13 |
| III-15 | A1 | N | O | C-B90 | C-B13 | III-16 | A1 | N | O | C-B91 | C-B13 |
| III-17 | A1 | N | S | C-B1 | C-B1 | III-18 | A1 | N | S | C-B13 | C-B13 |
| III-19 | A1 | N | S | C-B16 | C-B13 | III-20 | A1 | N | S | C-B17 | C-B13 |
| III-21 | A1 | N | S | C-B25 | C-B13 | III-22 | A1 | N | S | C-B52 | C-B13 |
| III-23 | A1 | N | S | C-B54 | C-B13 | III-24 | A1 | N | S | C-B55 | C-B13 |
| III-25 | A1 | N | S | C-B63 | C-B13 | III-26 | A1 | N | S | C-B68 | C-B13 |
| III-27 | A1 | N | S | C-B69 | C-B13 | III-28 | A1 | N | S | C-B70 | C-B13 |
| III-29 | A1 | N | S | C-B71 | C-B13 | III-30 | A1 | N | S | C-B89 | C-B13 |
| III-31 | A1 | N | S | C-B90 | C-B13 | III-32 | A1 | N | S | C-B91 | C-B13 |
| III-33 | A1 | N | Se | C-B1 | C-B1 | III-34 | A1 | N | Se | C-B13 | C-B13 |
| III-35 | A1 | N | Se | C-B16 | C-B13 | III-36 | A1 | N | Se | C-B17 | C-B13 |
| III-37 | A1 | N | Se | C-B25 | C-B13 | III-38 | A1 | N | Se | C-B52 | C-B13 |
| III-39 | A1 | N | Se | C-B54 | C-B13 | III-40 | A1 | N | Se | C-B55 | C-B13 |
| III-41 | A1 | N | Se | C-B63 | C-B13 | III-42 | A1 | N | Se | C-B68 | C-B13 |
| III-43 | A1 | N | Se | C-B69 | C-B13 | III-44 | A1 | N | Se | C-B70 | C-B13 |
| III-45 | A1 | N | Se | C-B71 | C-B13 | III-46 | A1 | N | Se | C-B89 | C-B13 |
| III-47 | A1 | N | Se | C-B90 | C-B13 | III-48 | A1 | N | Se | C-B91 | C-B13 |
| III-49 | A1 | N | NMe | C-B1 | C-B1 | III-50 | A1 | N | NMe | C-B13 | C-B13 |
| III-51 | A1 | N | NMe | C-B16 | C-B13 | III-52 | A1 | N | NMe | C-B17 | C-B13 |
| III-53 | A1 | N | NMe | C-B25 | C-B13 | III-54 | A1 | N | NMe | C-B52 | C-B13 |
| III-55 | A1 | N | NMe | C-B54 | C-B13 | III-56 | A1 | N | NMe | C-B55 | C-B13 |
| III-57 | A1 | N | NMe | C-B63 | C-B13 | III-58 | A1 | N | NMe | C-B68 | C-B13 |
| III-59 | A1 | N | NMe | C-B69 | C-B13 | III-60 | A1 | N | NMe | C-B70 | C-B13 |
| III-61 | A1 | N | NMe | C-B71 | C-B13 | III-62 | A1 | N | NMe | C-B89 | C-B13 |
| III-63 | A1 | N | NMe | C-B90 | C-B13 | III-64 | A1 | N | NMe | C-B91 | C-B13 | wherein, Compound IV-1 to Compound IV-64 have the structure of Formula IV:

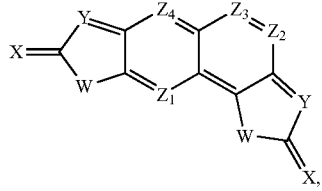

Formula IV in Formula IV, both of X are the same, both of Y are the same, both of W are the same, $Z_1$ and $Z_2$ are the same, $Z_3$ and $Z_4$ are the same, and X, Y, W, $Z_1$, $Z_2$, $Z_3$ and $Z_4$ are correspondingly selected from the atoms or groups as shown in the following table:

| No. | X | Y | W | $Z_1 = Z_2$ | $Z_3 = Z_4$ | No. | X | Y | W | $Z_1 = Z_2$ | $Z_3 = Z_4$ |
|---|---|---|---|---|---|---|---|---|---|---|---|
| IV-1 | A1 | N | O | C-B1 | C-B1 | IV-2 | A1 | N | O | C-B13 | C-B13 |
| IV-3 | A1 | N | O | C-B16 | C-B13 | IV-4 | A1 | N | O | C-B17 | C-B13 |
| IV-5 | A1 | N | O | C-B25 | C-B13 | IV-6 | A1 | N | O | C-B52 | C-B13 |
| IV-7 | A1 | N | O | C-B54 | C-B13 | IV-8 | A1 | N | O | C-B55 | C-B13 |
| IV-9 | A1 | N | O | C-B63 | C-B13 | IV-10 | A1 | N | O | C-B68 | C-B13 |
| IV-11 | A1 | N | O | C-B69 | C-B13 | IV-12 | A1 | N | O | C-B70 | C-B13 |
| IV-13 | A1 | N | O | C-B71 | C-B13 | IV-14 | A1 | N | O | C-B89 | C-B13 |
| IV-15 | A1 | N | O | C-B90 | C-B13 | IV-16 | A1 | N | O | C-B91 | C-B13 |
| IV-17 | A1 | N | S | C-B1 | C-B1 | IV-18 | A1 | N | S | C-B13 | C-B13 |
| IV-19 | A1 | N | S | C-B16 | C-B13 | IV-20 | A1 | N | S | C-B17 | C-B13 |
| IV-21 | A1 | N | S | C-B25 | C-B13 | IV-22 | A1 | N | S | C-B52 | C-B13 |
| IV-23 | A1 | N | S | C-B54 | C-B13 | IV-24 | A1 | N | S | C-B55 | C-B13 |
| IV-25 | A1 | N | S | C-B63 | C-B13 | IV-26 | A1 | N | S | C-B68 | C-B13 |
| IV-27 | A1 | N | S | C-B69 | C-B13 | IV-28 | A1 | N | S | C-B70 | C-B13 |
| IV-29 | A1 | N | S | C-B71 | C-B13 | IV-30 | A1 | N | S | C-B89 | C-B13 |
| IV-31 | A1 | N | S | C-B90 | C-B13 | IV-32 | A1 | N | S | C-B91 | C-B13 |
| IV-33 | A1 | N | Se | C-B1 | C-B1 | IV-34 | A1 | N | Se | C-B13 | C-B13 |

-continued

| No. | X | Y | W | $Z_1 = Z_2$ | $Z_3 = Z_4$ | No. | X | Y | W | $Z_1 = Z_2$ | $Z_3 = Z_4$ |
|---|---|---|---|---|---|---|---|---|---|---|---|
| IV-35 | A1 | N | Se | C-B16 | C-B13 | IV-36 | A1 | N | Se | C-B17 | C-B13 |
| IV-37 | A1 | N | Se | C-B25 | C-B13 | IV-38 | A1 | N | Se | C-B52 | C-B13 |
| IV-39 | A1 | N | Se | C-B54 | C-B13 | IV-40 | A1 | N | Se | C-B55 | C-B13 |
| IV-41 | A1 | N | Se | C-B63 | C-B13 | IV-42 | A1 | N | Se | C-B68 | C-B13 |
| IV-43 | A1 | N | Se | C-B69 | C-B13 | IV-44 | A1 | N | Se | C-B70 | C-B13 |
| IV-45 | A1 | N | Se | C-B71 | C-B13 | IV-46 | A1 | N | Se | C-B89 | C-B13 |
| IV-47 | A1 | N | Se | C-B90 | C-B13 | IV-48 | A1 | N | Se | C-B91 | C-B13 |
| IV-49 | A1 | N | NMe | C-B1 | C-B1 | IV-50 | A1 | N | NMe | C-B13 | C-B13 |
| IV-51 | A1 | N | NMe | C-B16 | C-B13 | IV-52 | A1 | N | NMe | C-B17 | C-B13 |
| IV-53 | A1 | N | NMe | C-B25 | C-B13 | IV-54 | A1 | N | NMe | C-B52 | C-B13 |
| IV-55 | A1 | N | NMe | C-B54 | C-B13 | IV-56 | A1 | N | NMe | C-B55 | C-B13 |
| IV-57 | A1 | N | NMe | C-B63 | C-B13 | IV-58 | A1 | N | NMe | C-B68 | C-B13 |
| IV-59 | A1 | N | NMe | C-B69 | C-B13 | IV-60 | A1 | N | NMe | C-B70 | C-B13 |
| IV-61 | A1 | N | NMe | C-B71 | C-B13 | IV-62 | A1 | N | NMe | C-B89 | C-B13 |
| IV-63 | A1 | N | NMe | C-B90 | C-B13 | IV-64 | A1 | N | NMe | C-B91 | C-B13 | wherein, Compound V-1 to Compound V-64 have the structure of Formula V:

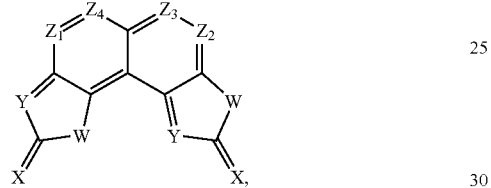

Fomula V in Formula V, both of X are the same, both of Y are the same, both of W are the same, $Z_1$ and $Z_2$ are the same, $Z_3$ and $Z_4$ are the same, and X, Y, W, $Z_1$, $Z_2$, $Z_3$ and $Z_4$ are correspondingly selected from the atoms or groups as shown in the following table:

| No. | X | Y | W | $Z_1 = Z_2$ | $Z_3 = Z_4$ | No. | X | Y | W | $Z_1 = Z_2$ | $Z_3 = Z_4$ |
|---|---|---|---|---|---|---|---|---|---|---|---|
| V-1 | A1 | N | O | C-B1 | C-B1 | V-2 | A1 | N | O | C-B13 | C-B13 |
| V-3 | A1 | N | O | C-B16 | C-B13 | V-4 | A1 | N | O | C-B17 | C-B13 |
| V-5 | A1 | N | O | C-B25 | C-B13 | V-6 | A1 | N | O | C-B52 | C-B13 |
| V-7 | A1 | N | O | C-B54 | C-B13 | V-8 | A1 | N | O | C-B55 | C-B13 |
| V-9 | A1 | N | O | C-B63 | C-B13 | V-10 | A1 | N | O | C-B68 | C-B13 |
| V-11 | A1 | N | O | C-B69 | C-B13 | V-12 | A1 | N | O | C-B70 | C-B13 |
| V-13 | A1 | N | O | C-B71 | C-B13 | V-14 | A1 | N | O | C-B89 | C-B13 |
| V-15 | A1 | N | O | C-B90 | C-B13 | V-16 | A1 | N | O | C-B91 | C-B13 |
| V-17 | A1 | N | S | C-B1 | C-B1 | V-18 | A1 | N | S | C-B13 | C-B13 |
| V-19 | A1 | N | S | C-B16 | C-B13 | V-20 | A1 | N | S | C-B17 | C-B13 |
| V-21 | A1 | N | S | C-B25 | C-B13 | V-22 | A1 | N | S | C-B52 | C-B13 |
| V-23 | A1 | N | S | C-B54 | C-B13 | V-24 | A1 | N | S | C-B55 | C-B13 |
| V-25 | A1 | N | S | C-B63 | C-B13 | V-26 | A1 | N | S | C-B68 | C-B13 |
| V-27 | A1 | N | S | C-B69 | C-B13 | V-28 | A1 | N | S | C-B70 | C-B13 |
| V-29 | A1 | N | S | C-B71 | C-B13 | V-30 | A1 | N | S | C-B89 | C-B13 |
| V-31 | A1 | N | S | C-B90 | C-B13 | V-32 | A1 | N | S | C-B91 | C-B13 |
| V-33 | A1 | N | Se | C-B1 | C-B1 | V-34 | A1 | N | Se | C-B13 | C-B13 |
| V-35 | A1 | N | Se | C-B16 | C-B13 | V-36 | A1 | Z | Se | C-B17 | C-B13 |
| V-37 | A1 | N | Se | C-B25 | C-B13 | V-38 | A1 | Z | Se | C-B52 | C-B13 |
| V-39 | A1 | N | Se | C-B54 | C-B13 | V-40 | A1 | N | Se | C-B55 | C-B13 |
| V-41 | A1 | N | Se | C-B63 | C-B13 | V-42 | A1 | N | Se | C-B68 | C-B13 |
| V-43 | A1 | N | Se | C-B69 | C-B13 | V-44 | A1 | N | Se | C-B70 | C-B13 |
| V-45 | A1 | N | Se | C-B71 | C-B13 | V-46 | A1 | N | Se | C-B89 | C-B13 |
| V-47 | A1 | N | Se | C-B90 | C-B13 | V-48 | A1 | N | Se | C-B91 | C-B13 |
| V-49 | A1 | N | NMe | C-B1 | C-B1 | V-50 | A1 | N | NMe | C-B13 | C-B13 |
| V-51 | A1 | N | NMe | C-B16 | C-B13 | V-52 | A1 | N | NMe | C-B17 | C-B13 |
| V-53 | A1 | N | NMe | C-B25 | C-B13 | V-54 | A1 | N | NMe | C-B52 | C-B13 |
| V-55 | A1 | N | NMe | C-B54 | C-B13 | V-56 | A1 | N | NMe | C-B55 | C-B13 |
| V-57 | A1 | N | NMe | C-B63 | C-B13 | V-58 | A1 | N | NMe | C-B68 | C-B13 |
| V-59 | A1 | N | NMe | C-B69 | C-B13 | V-60 | A1 | Z | NMe | C-B70 | C-B13 |
| V-61 | A1 | N | NMe | C-B71 | C-B13 | V-62 | A1 | N | NMe | C-B89 | C-B13 |
| V-63 | A1 | N | NMe | C-B90 | C-B13 | V-64 | A1 | N | NMe | C-B91 | C-B13 | wherein, Compound VI-1 to Compound VI-64 have the structure of Formula VI:

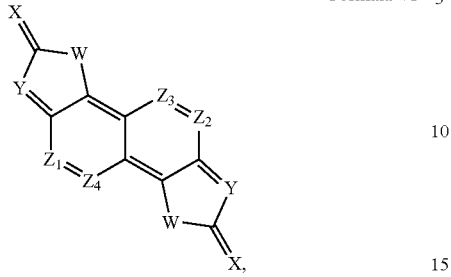

Formula VI in Formula VI, both of X are the same, both of Y are the same, both of W are the same, $Z_1$ and $Z_2$ are the same, $Z_3$ and $Z_4$ are the same, and X, Y, W, $Z_1$, $Z_2$, $Z_3$ and $Z_4$ are correspondingly selected from the atoms or groups as shown in the following table:

| No. | X | Y | W | $Z_1 = Z_2$ | $Z_3 = Z_4$ | No. | X | Y | W | $Z_1 = Z_2$ | $Z_3 = Z_4$ |
|---|---|---|---|---|---|---|---|---|---|---|---|
| VI-1 | A1 | N | O | C-B1 | C-B1 | VI-2 | A1 | N | O | C-B13 | C-B13 |
| VI-3 | A1 | N | O | C-B16 | C-B13 | VI-4 | A1 | N | O | C-B17 | C-B13 |
| VI-5 | A1 | N | O | C-B25 | C-B13 | VI-6 | A1 | N | O | C-B52 | C-B13 |
| VI-7 | A1 | N | O | C-B54 | C-B13 | VI-8 | A1 | N | O | C-B55 | C-B13 |
| VI-9 | A1 | N | O | C-B63 | C-B13 | VI-10 | A1 | N | O | C-B68 | C-B13 |
| VI-11 | A1 | N | O | C-B69 | C-B13 | VI-12 | A1 | N | O | C-B70 | C-B13 |
| VI-13 | A1 | N | O | C-B71 | C-B13 | VI-14 | A1 | N | O | C-B89 | C-B13 |
| VI-15 | A1 | N | O | C-B90 | C-B13 | VI-16 | A1 | N | O | C-B91 | C-B13 |
| VI-17 | A1 | N | S | C-B1 | C-B1 | VI-18 | A1 | N | S | C-B13 | C-B13 |
| VI-19 | A1 | N | S | C-B16 | C-B13 | VI-20 | A1 | N | S | C-B17 | C-B13 |
| VI-21 | A1 | N | S | C-B25 | C-B13 | VI-22 | A1 | N | S | C-B52 | C-B13 |
| VI-23 | A1 | N | S | C-B54 | C-B13 | VI-24 | A1 | N | S | C-B55 | C-B13 |
| VI-25 | A1 | N | S | C-B63 | C-B13 | VI-26 | A1 | N | S | C-B68 | C-B13 |
| VI-27 | A1 | N | S | C-B69 | C-B13 | VI-28 | A1 | N | S | C-B70 | C-B13 |
| VI-29 | A1 | N | S | C-B71 | C-B13 | VI-30 | A1 | N | S | C-B89 | C-B13 |
| VI-31 | A1 | N | S | C-B90 | C-B13 | VI-32 | A1 | N | S | C-B91 | C-B13 |
| VI-33 | A1 | N | Se | C-B1 | C-B1 | VI-34 | A1 | N | Se | C-B13 | C-B13 |
| VI-35 | A1 | N | Se | C-B16 | C-B13 | VI-36 | A1 | N | Se | C-B17 | C-B13 |
| VI-37 | A1 | N | Se | C-B25 | C-B13 | VI-38 | A1 | N | Se | C-B52 | C-B13 |
| VI-39 | A1 | N | Se | C-B54 | C-B13 | VI-40 | A1 | N | Se | C-B55 | C-B13 |
| VI-41 | A1 | N | Se | C-B63 | C-B13 | VI-42 | A1 | N | Se | C-B68 | C-B13 |
| VI-43 | A1 | N | Se | C-B69 | C-B13 | VI-44 | A1 | N | Se | C-B70 | C-B13 |
| VI-45 | A1 | N | Se | C-B71 | C-B13 | VI-46 | A1 | N | Se | C-B89 | C-B13 |
| VI-47 | A1 | N | Se | C-B90 | C-B13 | VI-48 | A1 | N | Se | C-B91 | C-B13 |
| VI-49 | A1 | N | NMe | C-B1 | C-B1 | VI-50 | A1 | N | NMe | C-B13 | C-B13 |
| VI-51 | A1 | N | NMe | C-B16 | C-B13 | VI-52 | A1 | N | NMe | C-B17 | C-B13 |
| VI-53 | A1 | N | NMe | C-B25 | C-B13 | VI-54 | A1 | N | NMe | C-B52 | C-B13 |
| VI-55 | A1 | N | NMe | C-B54 | C-B13 | VI-56 | A1 | N | NMe | C-B55 | C-B13 |
| VI-57 | A1 | N | NMe | C-B63 | C-B13 | VI-58 | A1 | N | NMe | C-B68 | C-B13 |
| VI-59 | A1 | N | NMe | C-B69 | C-B13 | VI-60 | A1 | N | NMe | C-B70 | C-B13 |
| VI-61 | A1 | N | NMe | C-B71 | C-B13 | VI-62 | A1 | N | NMe | C-B89 | C-B13 |
| VI-63 | A1 | N | NMe | C-B90 | C-B13 | VI-64 | A1 | N | NMe | C-B91 | C-B13 | wherein, Compound VII-1 to Compound VII-64 have the structure of Formula VII:

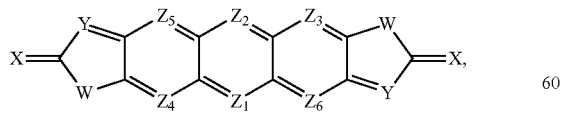

Formula VII in Formula VII, both of X are the same, both of Y are the same, both of W are the same, $Z_1$, $Z_2$, $Z_5$ and $Z_6$ are the same, $Z_3$ and $Z_4$ are the same, and X, Y, W, $Z_1$, $Z_2$, $Z_3$, $Z_4$, $Z_5$ and $Z_6$ are correspondingly selected from the atoms or groups as shown in the following table:

| No. | X | Y | W | $Z_1 = Z_2 =$ $Z_3 = Z_4$ | $Z_5 = Z_6$ | No. | X | Y | W | $Z_3 = Z_4$ | $Z_1 = Z_2 =$ $Z_5 = Z_6$ |
|---|---|---|---|---|---|---|---|---|---|---|---|
| VII-1 | A1 | N | O | C-B1 | C-B1 | VII-2 | A1 | N | O | C-B13 | C-B13 |
| VII-3 | A1 | N | O | C-B16 | C-B13 | VII-4 | A1 | N | O | C-B17 | C-B13 |
| VII-5 | A1 | N | O | C-B25 | C-B13 | VII-6 | A1 | N | O | C-B52 | C-B13 |
| VII-7 | A1 | N | O | C-B54 | C-B13 | VII-8 | A1 | N | O | C-B55 | C-B13 |
| VII-9 | A1 | N | O | C-B63 | C-B13 | VII-10 | A1 | N | O | C-B68 | C-B13 |
| VII-11 | A1 | N | O | C-B69 | C-B13 | VII-12 | A1 | N | O | C-B70 | C-B13 |
| VII-13 | A1 | N | O | C-B71 | C-B13 | VII-14 | A1 | N | O | C-B89 | C-B13 |
| VII-15 | A1 | N | O | C-B90 | C-B13 | VII-16 | A1 | N | O | C-B91 | C-B13 |
| VII-17 | A1 | N | S | C-B1 | C-B1 | VII-18 | A1 | N | S | C-B13 | C-B13 |
| VII-19 | A1 | N | S | C-B16 | C-B13 | VII-20 | A1 | N | S | C-B17 | C-B13 |
| VII-21 | A1 | N | S | C-B25 | C-B13 | VII-22 | A1 | N | S | C-B52 | C-B13 |
| VII-23 | A1 | N | S | C-B54 | C-B13 | VII-24 | A1 | N | S | C-B55 | C-B13 |
| VII-25 | A1 | N | S | C-B63 | C-B13 | VII-26 | A1 | N | S | C-B68 | C-B13 |
| VII-27 | A1 | N | S | C-B69 | C-B13 | VII-28 | A1 | N | S | C-B70 | C-B13 |
| VII-29 | A1 | N | S | C-B71 | C-B13 | VII-30 | A1 | N | S | C-B89 | C-B13 |
| VII-31 | A1 | N | S | C-B90 | C-B13 | VII-32 | A1 | N | S | C-B91 | C-B13 |
| VII-33 | A1 | N | Se | C-B1 | C-B1 | VII-34 | A1 | N | Se | C-B13 | C-B13 |
| VII-35 | A1 | N | Se | C-B16 | C-B13 | VII-36 | A1 | N | Se | C-B17 | C-B13 |
| VII-37 | A1 | N | Se | C-B25 | C-B13 | VII-38 | A1 | N | Se | C-B52 | C-B13 |
| VII-39 | A1 | N | Se | C-B54 | C-B13 | VII-40 | A1 | N | Se | C-B55 | C-B13 |
| VII-41 | A1 | N | Se | C-B63 | C-B13 | VII-42 | A1 | N | Se | C-B68 | C-B13 |
| VII-43 | A1 | N | Se | C-B69 | C-B13 | VII-44 | A1 | N | Se | C-B70 | C-B13 |
| VII-45 | A1 | N | Se | C-B71 | C-B13 | VII-46 | A1 | N | Se | C-B89 | C-B13 |
| VII-47 | A1 | N | Se | C-B90 | C-B13 | VII-48 | A1 | N | Se | C-B91 | C-B13 |
| VII-49 | A1 | N | NMe | C-B1 | C-B1 | VII-50 | A1 | N | NMe | C-B13 | C-B13 |
| VII-51 | A1 | N | NMe | C-B16 | C-B13 | VII-52 | A1 | N | NMe | C-B17 | C-B13 |
| VII-53 | A1 | N | NMe | C-B25 | C-B13 | VII-54 | A1 | N | NMe | C-B52 | C-B13 |
| VII-55 | A1 | N | NMe | C-B54 | C-B13 | VII-56 | A1 | N | NMe | C-B55 | C-B13 |
| VII-57 | A1 | N | NMe | C-B63 | C-B13 | VII-58 | A1 | N | NMe | C-B68 | C-B13 |
| VII-59 | A1 | N | NMe | C-B69 | C-B13 | VII-60 | A1 | N | NMe | C-B70 | C-B13 |
| VII-61 | A1 | N | NMe | C-B71 | C-B13 | VII-62 | A1 | N | NMe | C-B89 | C-B13 |
| VII-63 | A1 | N | NMe | C-B90 | C-B13 | VII-64 | A1 | N | NMe | C-B91 | C-B13 | wherein, Compound VIII-1 to Compound VIII-64 have the structure of Formula VIII:

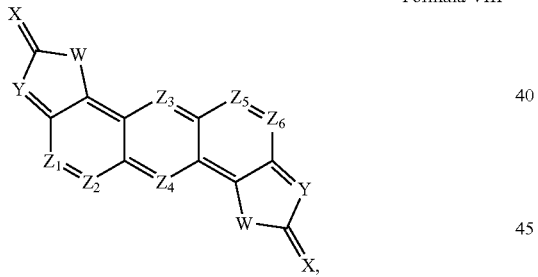

Formula VIII in Formula VIII, both of X are the same, both of Y are the same, both of W are the same, $Z_1$, $Z_2$, $Z_5$ and $Z_6$ are the same, $Z_3$ and $Z_4$ are the same, and X, Y, W, $Z_1$, $Z_2$, $Z_3$, $Z_4$, $Z_5$ and $Z_6$ are correspondingly selected from the atoms or groups as shown in the following table:

| No. | X | Y | W | $Z_3 = Z_4$ | $Z_1 = Z_2 =$ $Z_5 = Z_6$ | No. | X | Y | W | $Z_3 = Z_4$ | $Z_1 = Z_2 =$ $Z_5 = Z_6$ |
|---|---|---|---|---|---|---|---|---|---|---|---|
| VIII-1 | A1 | N | O | C-B1 | C-B1 | VIII-2 | A1 | N | O | C-B13 | C-B13 |
| VIII-3 | A1 | N | O | C-B16 | C-B13 | VIII-4 | A1 | N | O | C-B17 | C-B13 |
| VIII-5 | A1 | N | O | C-B25 | C-B13 | VIII-6 | A1 | N | O | C-B52 | C-B13 |
| VIII-7 | A1 | N | O | C-B54 | C-B13 | VIII-8 | A1 | N | O | C-B55 | C-B13 |
| VIII-9 | A1 | N | O | C-B63 | C-B13 | VIII-10 | A1 | N | O | C-B68 | C-B13 |
| VIII-11 | A1 | N | O | C-B69 | C-B13 | VIII-12 | A1 | N | O | C-B70 | C-B13 |
| VIII-13 | A1 | N | O | C-B71 | C-B13 | VIII-14 | A1 | N | O | C-B89 | C-B13 |
| VIII-15 | A1 | N | O | C-B90 | C-B13 | VIII-16 | A1 | N | O | C-B91 | C-B13 |
| VIII-17 | A1 | N | S | C-B1 | C-B1 | VIII-18 | A1 | N | S | C-B13 | C-B13 |
| VIII-19 | A1 | N | S | C-B16 | C-B13 | VIII-20 | A1 | N | S | C-B17 | C-B13 |
| VIII-21 | A1 | N | S | C-B25 | C-B13 | VIII-22 | A1 | N | S | C-B52 | C-B13 |

-continued

| No. | X | Y | W | $Z_3 = Z_4$ | $Z_1 = Z_2 =$ $Z_5 = Z_6$ | No. | X | Y | W | $Z_3 = Z_4$ | $Z_1 = Z_2 =$ $Z_5 = Z_6$ |
|---|---|---|---|---|---|---|---|---|---|---|---|
| VIII-23 | A1 | N | S | C-B54 | C-B13 | VIII-24 | A1 | N | S | C-B55 | C-B13 |
| VIII-25 | A1 | N | S | C-B63 | C-B13 | VIII-26 | A1 | N | S | C-B68 | C-B13 |
| VIII-27 | A1 | N | S | C-B69 | C-B13 | VIII-28 | A1 | N | S | C-B70 | C-B13 |
| VIII-29 | A1 | N | S | C-B71 | C-B13 | VIII-30 | A1 | N | S | C-B89 | C-B13 |
| VIII-31 | A1 | N | S | C-B90 | C-B13 | VIII-32 | A1 | N | S | C-B91 | C-B13 |
| VIII-33 | A1 | N | Se | C-B1 | C-B1 | VIII-34 | A1 | N | Se | C-B13 | C-B13 |
| VIII-35 | A1 | N | Se | C-B16 | C-B13 | VIII-36 | A1 | N | Se | C-B17 | C-B13 |
| VIII-37 | A1 | N | Se | C-B25 | C-B13 | VIII-38 | A1 | N | Se | C-B52 | C-B13 |
| VIII-39 | A1 | N | Se | C-B54 | C-B13 | VIII-40 | A1 | N | Se | C-B55 | C-B13 |
| VIII-41 | A1 | N | Se | C-B63 | C-B13 | VIII-42 | A1 | N | Se | C-B68 | C-B13 |
| VIII-43 | A1 | N | Se | C-B69 | C-B13 | VIII-44 | A1 | N | Se | C-B70 | C-B13 |
| VIII-45 | A1 | N | Se | C-B71 | C-B13 | VIII-46 | A1 | N | Se | C-B89 | C-B13 |
| VIII-47 | A1 | N | Se | C-B90 | C-B13 | VIII-48 | A1 | N | Se | C-B91 | C-B13 |
| VIII-49 | A1 | N | NMe | C-B1 | C-B1 | VIII-50 | A1 | N | NMe | C-B13 | C-B13 |
| VIII-51 | A1 | N | NMe | C-B16 | C-B13 | VIII-52 | A1 | N | NMe | C-B17 | C-B13 |
| VIII-53 | A1 | N | NMe | C-B25 | C-B13 | VIII-54 | A1 | N | NMe | C-B52 | C-B13 |
| VIII-55 | A1 | N | NMe | C-B54 | C-B13 | VIII-56 | A1 | N | NMe | C-B55 | C-B13 |
| VIII-57 | A1 | N | NMe | C-B63 | C-B13 | VIII-58 | A1 | N | NMe | C-B68 | C-B13 |
| VIII-59 | A1 | N | NMe | C-B69 | C-B13 | VIII-60 | A1 | N | NMe | C-B70 | C-B13 |
| VIII-61 | A1 | N | NMe | C-B71 | C-B13 | VIII-62 | A1 | N | NMe | C-B89 | C-B13 |
| VIII-63 | A1 | N | NMe | C-B90 | C-B13 | VIII-64 | A1 | N | NMe | C-B91 | C-B13 | wherein, Compound IX-1 to Compound IX-64 have the structure of Formula IX:

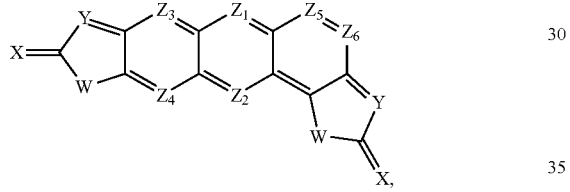

Formula IX in Formula IX, both of X are the same, both of Y are the same, both of W are the same, $Z_3$, $Z_4$, $Z_5$ and $Z_6$ are the same, $Z_1$ and $Z_2$ are the same, and X, Y, W, $Z_1$, $Z_2$, $Z_3$, $Z_4$, $Z_5$ and $Z_6$ are correspondingly selected from the atoms or groups as shown in the following table:

| No. | X | Y | W | $Z_1 = Z_2$ | $Z_3 = Z_4 =$ $Z_5 = Z_6$ | No. | X | Y | W | $Z_1 = Z_2$ | $Z_3 = Z_4 =$ $Z_5 = Z_6$ |
|---|---|---|---|---|---|---|---|---|---|---|---|
| IX-1 | A1 | N | O | C-B1 | C-B1 | IX-2 | A1 | N | O | C-B13 | C-B13 |
| IX-3 | A1 | N | O | C-B16 | C-B13 | IX-4 | A1 | N | O | C-B17 | C-B13 |
| IX-5 | A1 | N | O | C-B25 | C-B13 | IX-6 | A1 | N | O | C-B52 | C-B13 |
| IX-7 | A1 | N | O | C-B54 | C-B13 | IX-8 | A1 | N | O | C-B55 | C-B13 |
| IX-9 | A1 | N | O | C-B63 | C-B13 | IX-10 | A1 | N | O | C-B68 | C-B13 |
| IX-11 | A1 | N | O | C-B69 | C-B13 | IX-12 | A1 | N | O | C-B70 | C-B13 |
| IX-13 | A1 | N | O | C-B71 | C-B13 | IX-14 | A1 | N | O | C-B89 | C-B13 |
| IX-15 | A1 | N | O | C-B90 | C-B13 | IX-16 | A1 | N | O | C-B91 | C-B13 |
| IX-17 | A1 | N | S | C-B1 | C-B1 | IX-18 | A1 | N | S | C-B13 | C-B13 |
| IX-19 | A1 | N | S | C-B16 | C-B13 | IX-20 | A1 | N | S | C-B17 | C-B13 |
| IX-21 | A1 | N | S | C-B25 | C-B13 | IX-22 | A1 | N | S | C-B52 | C-B13 |
| IX-23 | A1 | N | S | C-B54 | C-B13 | IX-24 | A1 | N | S | C-B55 | C-B13 |
| IX-25 | A1 | N | S | C-B63 | C-B13 | IX-26 | A1 | N | S | C-B68 | C-B13 |
| IX-27 | A1 | N | S | C-B69 | C-B13 | IX-28 | A1 | N | S | C-B70 | C-B13 |
| IX-29 | A1 | N | S | C-B71 | C-B13 | IX-30 | A1 | N | S | C-B89 | C-B13 |
| IX-31 | A1 | N | S | C-B90 | C-B13 | IX-32 | A1 | N | S | C-B91 | C-B13 |
| IX-33 | A1 | N | Se | C-B1 | C-B1 | IX-34 | A1 | N | Se | C-B13 | C-B13 |
| IX-35 | A1 | N | Se | C-B16 | C-B13 | IX-36 | A1 | N | Se | C-B17 | C-B13 |
| IX-37 | A1 | N | Se | C-B25 | C-B13 | IX-38 | A1 | N | Se | C-B52 | C-B13 |
| IX-39 | A1 | N | Se | C-B54 | C-B13 | IX-40 | A1 | N | Se | C-B55 | C-B13 |
| IX-41 | A1 | N | Se | C-B63 | C-B13 | IX-42 | A1 | N | Se | C-B68 | C-B13 |
| IX-43 | A1 | N | Se | C-B69 | C-B13 | IX-44 | A1 | N | Se | C-B70 | C-B13 |
| IX-45 | A1 | N | Se | C-B71 | C-B13 | IX-46 | A1 | N | Se | C-B89 | C-B13 |
| IX-47 | A1 | N | Se | C-B90 | C-B13 | IX-48 | A1 | N | Se | C-B91 | C-B13 |
| IX-49 | A1 | N | NMe | C-B1 | C-B1 | IX-50 | A1 | N | NMe | C-B13 | C-B13 |

-continued

| No. | X | Y | W | $Z_1 = Z_2$ | $Z_3 = Z_4 =$ $Z_5 = Z_6$ | No. | X | Y | W | $Z_1 = Z_2$ | $Z_3 = Z_4 =$ $Z_5 = Z_6$ |
|---|---|---|---|---|---|---|---|---|---|---|---|
| IX-51 | A1 | N | NMe | C-B16 | C-B13 | IX-52 | A1 | N | NMe | C-B17 | C-B13 |
| IX-53 | A1 | N | NMe | C-B25 | C-B13 | IX-54 | A1 | N | NMe | C-B52 | C-B13 |
| IX-55 | A1 | N | NMe | C-B54 | C-B13 | IX-56 | A1 | N | NMe | C-B55 | C-B13 |
| IX-57 | A1 | N | NMe | C-B63 | C-B13 | IX-58 | A1 | N | NMe | C-B68 | C-B13 |
| IX-59 | A1 | N | NMe | C-B69 | C-B13 | IX-60 | A1 | N | NMe | C-B70 | C-B13 |
| IX-61 | A1 | N | NMe | C-B71 | C-B13 | IX-62 | A1 | N | NMe | C-B89 | C-B13 |
| IX-63 | A1 | N | NMe | C-B90 | C-B13 | IX-64 | A1 | N | NMe | C-B91 | C-B13 | wherein, Compound X-1 to Compound X-64 have the structure of Formula X:

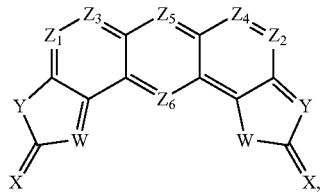

Formula X in Formula X, both of X are the same, both of Y are the same, both of W are the same, $Z_3$, $Z_4$, $Z_5$ and $Z_6$ are the same, $Z_1$ and $Z_2$ are the same, and X, Y, W, $Z_1$, $Z_2$, $Z_3$, $Z_4$, $Z_5$ and $Z_6$ are correspondingly selected from the atoms or groups as shown in the following table:

| No. | X | Y | W | $Z_1 = Z_2$ | $Z_3 = Z_4 =$ $Z_5 = Z_6$ | No. | X | Y | W | $Z_1 = Z_2$ | $Z_3 = Z_4 =$ $Z_5 = Z_6$ |
|---|---|---|---|---|---|---|---|---|---|---|---|
| X-1 | A1 | N | O | C-B1 | C-B1 | X-2 | A1 | N | O | C-B13 | C-B13 |
| X-3 | A1 | N | O | C-B16 | C-B13 | X-4 | A1 | N | O | C-B17 | C-B13 |
| X-5 | A1 | N | O | C-B25 | C-B13 | X-6 | A1 | N | O | C-B52 | C-B13 |
| X-7 | A1 | N | O | C-B54 | C-B13 | X-8 | A1 | N | O | C-B55 | C-B13 |
| X-9 | A1 | N | O | C-B63 | C-B13 | X-10 | A1 | N | O | C-B68 | C-B13 |
| X-11 | A1 | N | O | C-B69 | C-B13 | X-12 | A1 | N | O | C-B70 | C-B13 |
| X-13 | A1 | N | O | C-B71 | C-B13 | X-14 | A1 | N | O | C-B89 | C-B13 |
| X-15 | A1 | N | O | C-B90 | C-B13 | X-16 | A1 | N | O | C-B91 | C-B13 |
| X-17 | A1 | N | S | C-B1 | C-B1 | X-18 | A1 | N | S | C-B13 | C-B13 |
| X-19 | A1 | N | S | C-B16 | C-B13 | X-20 | A1 | N | S | C-B17 | C-B13 |
| X-21 | A1 | N | S | C-B25 | C-B13 | X-22 | A1 | N | S | C-B52 | C-B13 |
| X-23 | A1 | N | S | C-B54 | C-B13 | X-24 | A1 | N | S | C-B55 | C-B13 |
| X-25 | A1 | N | S | C-B63 | C-B13 | X-26 | A1 | N | S | C-B68 | C-B13 |
| X-27 | A1 | N | S | C-B69 | C-B13 | X-28 | A1 | N | S | C-B70 | C-B13 |
| X-29 | A1 | N | S | C-B71 | C-B13 | X-30 | A1 | N | S | C-B89 | C-B13 |
| X-31 | A1 | N | S | C-B90 | C-B13 | X-32 | A1 | N | S | C-B91 | C-B13 |
| X-33 | A1 | N | Se | C-B1 | C-B1 | X-34 | A1 | N | Se | C-B13 | C-B13 |
| X-35 | A1 | N | Se | C-B16 | C-B13 | X-36 | A1 | N | Se | C-B17 | C-B13 |
| X-37 | A1 | N | Se | C-B25 | C-B13 | X-38 | A1 | N | Se | C-B52 | C-B13 |
| X-39 | A1 | N | Se | C-B54 | C-B13 | X-40 | A1 | N | Se | C-B55 | C-B13 |
| X-41 | A1 | N | Se | C-B63 | C-B13 | X-42 | A1 | N | Se | C-B68 | C-B13 |
| X-43 | A1 | N | Se | C-B69 | C-B13 | X-44 | A1 | N | Se | C-B70 | C-B13 |
| X-45 | A1 | N | Se | C-B71 | C-B13 | X-46 | A1 | N | Se | C-B89 | C-B13 |
| X-47 | A1 | N | Se | C-B90 | C-B13 | X-48 | A1 | N | Se | C-B91 | C-B13 |
| X-49 | A1 | N | NMe | C-B1 | C-B1 | X-50 | A1 | N | NMe | C-B13 | C-B13 |
| X-51 | A1 | N | NMe | C-B16 | C-B13 | X-52 | A1 | N | NMe | C-B17 | C-B13 |
| X-53 | A1 | N | NMe | C-B25 | C-B13 | X-54 | A1 | N | NMe | C-B52 | C-B13 |
| X-55 | A1 | N | NMe | C-B54 | C-B13 | X-56 | A1 | N | NMe | C-B55 | C-B13 |
| X-57 | A1 | N | NMe | C-B63 | C-B13 | X-58 | A1 | N | NMe | C-B68 | C-B13 |
| X-59 | A1 | N | NMe | C-B69 | C-B13 | X-60 | A1 | N | NMe | C-B70 | C-B13 |
| X-61 | A1 | N | NMe | C-B71 | C-B13 | X-62 | A1 | N | NMe | C-B89 | C-B13 |
| X-63 | A1 | N | NMe | C-B90 | C-B13 | X-64 | A1 | N | NMe | C-B91 | C-B13 | wherein, Compound XI-1 to Compound XI-1 to Compound XI-64 have the structure of Formula XI:

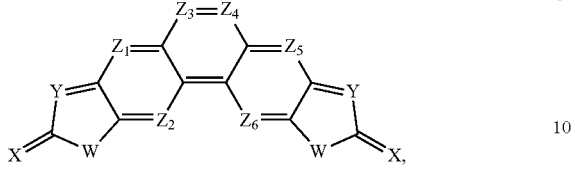

Formula XI in Formula XI, both of X are the same, both of Y are the same, both of W are the same, $Z_1$, $Z_2$, $Z_5$ and $Z_6$ are the same, $Z_3$ and $Z_4$ are the same, and X, Y, W, $Z_1$, $Z_2$, $Z_3$, $Z_4$, $Z_5$ and $Z_6$ are correspondingly selected from the atoms or groups as shown in the following table:

| No. | X | Y | W | $Z_3 = Z_4$ | $Z_1 = Z_2 =$ $Z_5 = Z_6$ | No. | X | Y | W | $Z_3 = Z_4$ | $Z_1 = Z_2 =$ $Z_5 = Z_6$ |
|---|---|---|---|---|---|---|---|---|---|---|---|
| XI-1 | A1 | N | O | C-B1 | C-B1 | XI-2 | A1 | N | O | C-B13 | C-B13 |
| XI-3 | A1 | N | O | C-B16 | C-B13 | XI-4 | A1 | N | O | C-B17 | C-B13 |
| XI-5 | A1 | N | O | C-B25 | C-B13 | XI-6 | A1 | N | O | C-B52 | C-B13 |
| XI-7 | A1 | N | O | C-B54 | C-B13 | XI-8 | A1 | N | O | C-B55 | C-B13 |
| XI-9 | A1 | N | O | C-B63 | C-B13 | XI-10 | A1 | N | O | C-B68 | C-B13 |
| XI-11 | A1 | N | O | C-B69 | C-B13 | XI-12 | A1 | N | O | C-B70 | C-B13 |
| XI-13 | A1 | N | O | C-B71 | C-B13 | XI-14 | A1 | N | O | C-B89 | C-B13 |
| XI-15 | A1 | N | O | C-B90 | C-B13 | XI-16 | A1 | N | O | C-B91 | C-B13 |
| XI-17 | A1 | N | S | C-B1 | C-B1 | XI-18 | A1 | N | S | C-B13 | C-B13 |
| XI-19 | A1 | N | S | C-B16 | C-B13 | XI-20 | A1 | N | S | C-B17 | C-B13 |
| XI-21 | A1 | N | S | C-B25 | C-B13 | XI-22 | A1 | N | S | C-B52 | C-B13 |
| XI-23 | A1 | N | S | C-B54 | C-B13 | XI-24 | A1 | N | S | C-B55 | C-B13 |
| XI-25 | A1 | N | S | C-B63 | C-B13 | XI-26 | A1 | N | S | C-B68 | C-B13 |
| XI-27 | A1 | N | S | C-B69 | C-B13 | XI-28 | A1 | N | S | C-B70 | C-B13 |
| XI-29 | A1 | N | S | C-B71 | C-B13 | XI-30 | A1 | N | S | C-B89 | C-B13 |
| XI-31 | A1 | N | S | C-B90 | C-B13 | XI-32 | A1 | N | S | C-B91 | C-B13 |
| XI-33 | A1 | N | Se | C-B1 | C-B1 | XI-34 | A1 | N | Se | C-B13 | C-B13 |
| XI-35 | A1 | N | Se | C-B16 | C-B13 | XI-36 | A1 | N | Se | C-B17 | C-B13 |
| XI-37 | A1 | N | Se | C-B25 | C-B13 | XI-38 | A1 | N | Se | C-B52 | C-B13 |
| XI-39 | A1 | N | Se | C-B54 | C-B13 | XI-40 | A1 | N | Se | C-B55 | C-B13 |
| XI-41 | A1 | N | Se | C-B63 | C-B13 | XI-42 | A1 | N | Se | C-B68 | C-B13 |
| XI-43 | A1 | N | Se | C-B69 | C-B13 | XI-44 | A1 | N | Se | C-B70 | C-B13 |
| XI-45 | A1 | N | Se | C-B71 | C-B13 | XI-46 | A1 | N | Se | C-B89 | C-B13 |
| XI-47 | A1 | N | Se | C-B90 | C-B13 | XI-48 | A1 | N | Se | C-B91 | C-B13 |
| XI-49 | A1 | N | NMe | C-B1 | C-B1 | XI-50 | A1 | N | NMe | C-B13 | C-B13 |
| XI-51 | A1 | N | NMe | C-B16 | C-B13 | XI-52 | A1 | N | NMe | C-B17 | C-B13 |
| XI-53 | A1 | N | NMe | C-B25 | C-B13 | XI-54 | A1 | N | NMe | C-B52 | C-B13 |
| XI-55 | A1 | N | NMe | C-B54 | C-B13 | XI-56 | A1 | N | NMe | C-B55 | C-B13 |
| XI-57 | A1 | N | NMe | C-B63 | C-B13 | XI-58 | A1 | N | NMe | C-B68 | C-B13 |
| XI-59 | A1 | N | NMe | C-B69 | C-B13 | XI-60 | A1 | N | NMe | C-B70 | C-B13 |
| XI-61 | A1 | N | NMe | C-B71 | C-B13 | XI-62 | A1 | N | NMe | C-B89 | C-B13 |
| XI-63 | A1 | N | NMe | C-B90 | C-B13 | XI-64 | A1 | N | NMe | C-B91 | C-B13 | wherein, Compound XII-1 to Compound XII-64 have the structure of Formula XII:

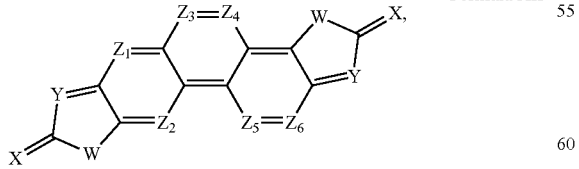

Formula XII in Formula XII, both of X are the same, both of Y are the same, both of W are the same, $Z_1$, $Z_2$, $Z_5$ and $Z_6$ are the same, $Z_3$ and $Z_4$ are the same, and X, Y, W, $Z_1$, $Z_2$, $Z_3$, $Z_4$, $Z_5$ and $Z_6$ are correspondingly selected from the atoms or groups as shown in the following table:

| No. | X | Y | W | $Z_3 = Z_4$ | $Z_1 = Z_2 =$ $Z_5 = Z_6$ | No. | X | Y | W | $Z_3 = Z_4$ | $Z_1 = Z_2 =$ $Z_5 = Z_6$ |
|---|---|---|---|---|---|---|---|---|---|---|---|
| XII-1 | A1 | N | O | C-B1 | C-B1 | XII-2 | A1 | N | O | C-B13 | C-B13 |
| XII-3 | A1 | N | O | C-B16 | C-B13 | XII-4 | A1 | N | O | C-B17 | C-B13 |
| XII-5 | A1 | N | O | C-B25 | C-B13 | XII-6 | A1 | N | O | C-B52 | C-B13 |
| XII-7 | A1 | N | O | C-B54 | C-B13 | XII-8 | A1 | N | O | C-B55 | C-B13 |
| XII-9 | A1 | N | O | C-B63 | C-B13 | XII-10 | A1 | N | O | C-B68 | C-B13 |
| XII-11 | A1 | N | O | C-B69 | C-B13 | XII-12 | A1 | N | O | C-B70 | C-B13 |
| XII-13 | A1 | N | O | C-B71 | C-B13 | XII-14 | A1 | N | O | C-B89 | C-B13 |
| XII-15 | A1 | N | O | C-B90 | C-B13 | XII-16 | A1 | N | O | C-B91 | C-B13 |
| XII-17 | A1 | N | S | C-B1 | C-B1 | XII-18 | A1 | N | S | C-B13 | C-B13 |
| XII-19 | A1 | N | S | C-B16 | C-B13 | XII-20 | A1 | N | S | C-B17 | C-B13 |
| XII-21 | A1 | N | S | C-B25 | C-B13 | XII-22 | A1 | N | S | C-B52 | C-B13 |
| XII-23 | A1 | N | S | C-B54 | C-B13 | XII-24 | A1 | N | S | C-B55 | C-B13 |
| XII-25 | A1 | N | S | C-B63 | C-B13 | XII-26 | A1 | N | S | C-B68 | C-B13 |
| XII-27 | A1 | N | S | C-B69 | C-B13 | XII-28 | A1 | N | S | C-B70 | C-B13 |
| XII-29 | A1 | N | S | C-B71 | C-B13 | XII-30 | A1 | N | S | C-B89 | C-B13 |
| XII-31 | A1 | N | S | C-B90 | C-B13 | XII-32 | A1 | N | S | C-B91 | C-B13 |
| XII-33 | A1 | N | Se | C-B1 | C-B1 | XII-34 | A1 | N | Se | C-B13 | C-B13 |
| XII-35 | A1 | N | Se | C-B16 | C-B13 | XII-36 | A1 | N | Se | C-B17 | C-B13 |
| XII-37 | A1 | N | Se | C-B25 | C-B13 | XII-38 | A1 | N | Se | C-B52 | C-B13 |
| XII-39 | A1 | N | Se | C-B54 | C-B13 | XII-40 | A1 | N | Se | C-B55 | C-B13 |
| XII-41 | A1 | N | Se | C-B63 | C-B13 | XII-42 | A1 | N | Se | C-B68 | C-B13 |
| XII-43 | A1 | N | Se | C-B69 | C-B13 | XII-44 | A1 | N | Se | C-B70 | C-B13 |
| XII-45 | A1 | N | Se | C-B71 | C-B13 | XII-46 | A1 | N | Se | C-B89 | C-B13 |
| XII-47 | A1 | N | Se | C-B90 | C-B13 | XII-48 | A1 | N | Se | C-B91 | C-B13 |
| XII-49 | A1 | N | NMe | C-B1 | C-B1 | XII-50 | A1 | N | NMe | C-B13 | C-B13 |
| XII-51 | A1 | N | NMe | C-B16 | C-B13 | XII-52 | A1 | N | NMe | C-B17 | C-B13 |
| XII-53 | A1 | N | NMe | C-B25 | C-B13 | XII-54 | A1 | N | NMe | C-B52 | C-B13 |
| XII-55 | A1 | N | NMe | C-B54 | C-B13 | XII-56 | A1 | N | NMe | C-B55 | C-B13 |
| XII-57 | A1 | N | NMe | C-B63 | C-B13 | XII-58 | A1 | N | NMe | C-B68 | C-B13 |
| XII-59 | A1 | N | NMe | C-B69 | C-B13 | XII-60 | A1 | N | NMe | C-B70 | C-B13 |
| XII-61 | A1 | N | NMe | C-B71 | C-B13 | XII-62 | A1 | N | NMe | C-B89 | C-B13 |
| XII-63 | A1 | N | NMe | C-B90 | C-B13 | XII-64 | A1 | N | NMe | C-B91 | C-B13 | wherein, Compound XIII-1 to Compound XIII-64 have the structure of Formula XIII:

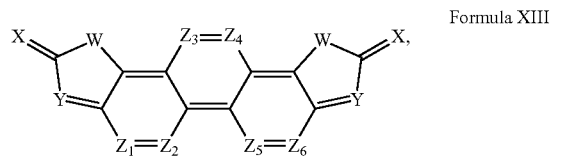

Formula XIII in Formula XIII, both of X are the same, both of Y are the same, both of W are the same, $Z_1$, $Z_2$, $Z_5$ and $Z_6$ are the same, $Z_3$ and $Z_4$ are the same, and X, Y, W, $Z_1$, $Z_2$, $Z_3$, $Z_4$, $Z_5$ and $Z_6$ are correspondingly selected from the atoms or groups as shown in the following table:

| No. | X | Y | W | $Z_3 = Z_4$ | $Z_1 = Z_2 =$ $Z_5 = Z_6$ | No. | X | Y | W | $Z_3 = Z_4$ | $Z_1 = Z_2 =$ $Z_5 = Z_6$ |
|---|---|---|---|---|---|---|---|---|---|---|---|
| XIII-1 | A1 | N | O | C-B1 | C-B1 | XIII-2 | A1 | N | O | C-B13 | C-B13 |
| XIII-3 | A1 | N | O | C-B16 | C-B13 | XIII-4 | A1 | N | O | C-B17 | C-B13 |
| XIII-5 | A1 | N | O | C-B25 | C-B13 | XIII-6 | A1 | N | O | C-B52 | C-B13 |
| XIII-7 | A1 | N | O | C-B54 | C-B13 | XIII-8 | A1 | N | O | C-B55 | C-B13 |
| XIII-9 | A1 | N | O | C-B63 | C-B13 | XIII-10 | A1 | N | O | C-B68 | C-B13 |
| XIII-11 | A1 | N | O | C-B69 | C-B13 | XIII-12 | A1 | N | O | C-B70 | C-B13 |
| XIII-13 | A1 | N | O | C-B71 | C-B13 | XIII-14 | A1 | N | O | C-B89 | C-B13 |
| XIII-15 | A1 | N | O | C-B90 | C-B13 | XIII-16 | A1 | N | O | C-B91 | C-B13 |
| XIII-17 | A1 | N | S | C-B1 | C-B1 | XIII-18 | A1 | N | S | C-B13 | C-B13 |
| XIII-19 | A1 | N | S | C-B16 | C-B13 | XIII-20 | A1 | N | S | C-B17 | C-B13 |
| XIII-21 | A1 | N | S | C-B25 | C-B13 | XIII-22 | A1 | N | S | C-B52 | C-B13 |
| XIII-23 | A1 | N | S | C-B54 | C-B13 | XIII-24 | A1 | N | S | C-B55 | C-B13 |
| XIII-25 | A1 | N | S | C-B63 | C-B13 | XIII-26 | A1 | N | S | C-B68 | C-B13 |
| XIII-27 | A1 | N | S | C-B69 | C-B13 | XIII-28 | A1 | N | S | C-B70 | C-B13 |
| XIII-29 | A1 | N | S | C-B71 | C-B13 | XIII-30 | A1 | N | S | C-B89 | C-B13 |
| XIII-31 | A1 | N | S | C-B90 | C-B13 | XIII-32 | A1 | N | S | C-B91 | C-B13 |
| XIII-33 | A1 | N | Se | C-B1 | C-B1 | XIII-34 | A1 | N | Se | C-B13 | C-B13 |
| XIII-35 | A1 | N | Se | C-B16 | C-B13 | XIII-36 | A1 | N | Se | C-B17 | C-B13 |

-continued

| No. | X | Y | W | $Z_3 = Z_4$ $Z_5 = Z_6$ | $Z_1 = Z_2 =$ | No. | X | Y | W | $Z_3 = Z_4$ | $Z_1 = Z_2 =$ $Z_5 = Z_6$ |
|---|---|---|---|---|---|---|---|---|---|---|---|
| XIII-37 | A1 | N | Se | C-B25 | C-B13 | XIII-38 | A1 | N | Se | C-B52 | C-B13 |
| XIII-39 | A1 | N | Se | C-B54 | C-B13 | XIII-40 | A1 | N | Se | C-B55 | C-B13 |
| XIII-41 | A1 | N | Se | C-B63 | C-B13 | XIII-42 | A1 | N | Se | C-B68 | C-B13 |
| XIII-43 | A1 | N | Se | C-B69 | C-B13 | XIII-44 | A1 | N | Se | C-B70 | C-B13 |
| XIII-45 | A1 | N | Se | C-B71 | C-B13 | XIII-46 | A1 | N | Se | C-B89 | C-B13 |
| XIII-47 | A1 | N | Se | C-B90 | C-B13 | XIII-48 | A1 | N | Se | C-B91 | C-B13 |
| XIII-49 | A1 | N | NMe | C-B1 | C-B1 | XIII-50 | A1 | N | NMe | C-B13 | C-B13 |
| XIII-51 | A1 | N | NMe | C-B16 | C-B13 | XIII-52 | A1 | N | NMe | C-B17 | C-B13 |
| XIII-53 | A1 | N | NMe | C-B25 | C-B13 | XIII-54 | A1 | N | NMe | C-B52 | C-B13 |
| XIII-55 | A1 | N | NMe | C-B54 | C-B13 | XIII-56 | A1 | N | NMe | C-B55 | C-B13 |
| XIII-57 | A1 | N | NMe | C-B63 | C-B13 | XIII-58 | A1 | N | NMe | C-B68 | C-B13 |
| XIII-59 | A1 | N | NMe | C-B69 | C-B13 | XIII-60 | A1 | N | NMe | C-B70 | C-B13 |
| XIII-61 | A1 | N | NMe | C-B71 | C-B13 | XIII-62 | A1 | N | NMe | C-B89 | C-B13 |
| XIII-63 | A1 | N | NMe | C-B90 | C-B13 | XIII-64 | A1 | N | NMe | C-B91 | C-B13 | wherein, Compound XIV-1 to Compound XIV-64 have the structure of Formula XIV:

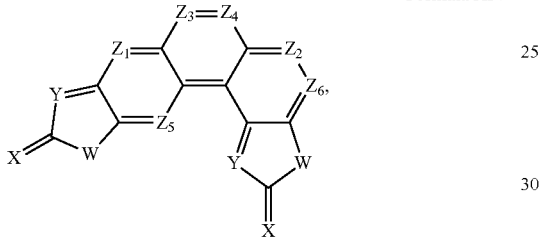

Formula XIV in Formula XIV, both of X are the same, both of Y are the same, both of W are the same, $Z_3$, $Z_4$, $Z_5$ and $Z_6$ are the same, $Z_1$ and $Z_2$ are the same, and X, Y, W, $Z_1$, $Z_2$, $Z_3$, $Z_4$, $Z_5$ and $Z_6$ are correspondingly selected from the atoms or groups as shown in the following table:

| No. | X | Y | W | $Z_1 = Z_2$ | $Z_3 = Z_4 =$ $Z_5 = Z_6$ | No. | X | Y | W | $Z_1 = Z_2$ | $Z_3 = Z_4 =$ $Z_5 = Z_6$ |
|---|---|---|---|---|---|---|---|---|---|---|---|
| XIV-1 | A1 | N | O | C-B1 | C-B1 | XIV-2 | A1 | N | O | C-B13 | C-B13 |
| XIV-3 | A1 | N | O | C-B16 | C-B13 | XIV-4 | A1 | N | O | C-B17 | C-B13 |
| XIV-5 | A1 | N | O | C-B25 | C-B13 | XIV-6 | A1 | N | O | C-B52 | C-B13 |
| XIV-7 | A1 | N | O | C-B54 | C-B13 | XIV-8 | A1 | N | O | C-B55 | C-B13 |
| XIV-9 | A1 | N | O | C-B63 | C-B13 | XIV-10 | A1 | N | O | C-B68 | C-B13 |
| XIV-11 | A1 | N | O | C-B69 | C-B13 | XIV-12 | A1 | N | O | C-B70 | C-B13 |
| XIV-13 | A1 | N | O | C-B71 | C-B13 | XIV-14 | A1 | N | O | C-B89 | C-B13 |
| XIV-15 | A1 | N | O | C-B90 | C-B13 | XIV-16 | A1 | N | O | C-B91 | C-B13 |
| XIV-17 | A1 | N | S | C-B1 | C-B1 | XIV-18 | A1 | N | S | C-B13 | C-B13 |
| XIV-19 | A1 | N | S | C-B16 | C-B13 | XIV-20 | A1 | N | S | C-B17 | C-B13 |
| XIV-21 | A1 | N | S | C-B25 | C-B13 | XIV-22 | A1 | N | S | C-B52 | C-B13 |
| XIV-23 | A1 | N | S | C-B54 | C-B13 | XIV-24 | A1 | N | S | C-B55 | C-B13 |
| XIV-25 | A1 | N | S | C-B63 | C-B13 | XIV-26 | A1 | N | S | C-B68 | C-B13 |
| XIV-27 | A1 | N | S | C-B69 | C-B13 | XIV-28 | A1 | N | S | C-B70 | C-B13 |
| XIV-29 | A1 | N | S | C-B71 | C-B13 | XIV-30 | A1 | N | S | C-B89 | C-B13 |
| XIV-31 | A1 | N | S | C-B90 | C-B13 | XIV-32 | A1 | N | S | C-B91 | C-B13 |
| XIV-33 | A1 | N | Se | C-B1 | C-B1 | XIV-34 | A1 | N | Se | C-B13 | C-B13 |
| XIV-35 | A1 | N | Se | C-B16 | C-B13 | XIV-36 | A1 | N | Se | C-B17 | C-B13 |
| XIV-37 | A1 | N | Se | C-B25 | C-B13 | XIV-38 | A1 | N | Se | C-B52 | C-B13 |
| XIV-39 | A1 | N | Se | C-B54 | C-B13 | XIV-40 | A1 | N | Se | C-B55 | C-B13 |
| XIV-41 | A1 | N | Se | C-B63 | C-B13 | XIV-42 | A1 | N | Se | C-B68 | C-B13 |
| XIV-43 | A1 | N | Se | C-B69 | C-B13 | XIV-44 | A1 | N | Se | C-B70 | C-B13 |
| XIV-45 | A1 | N | Se | C-B71 | C-B13 | XIV-46 | A1 | N | Se | C-B89 | C-B13 |
| XIV-47 | A1 | N | Se | C-B90 | C-B13 | XIV-48 | A1 | N | Se | C-B91 | C-B13 |
| XIV-49 | A1 | N | NMe | C-B1 | C-B1 | XIV-50 | A1 | N | NMe | C-B13 | C-B13 |
| XIV-51 | A1 | N | NMe | C-B16 | C-B13 | XIV-52 | A1 | N | NMe | C-B17 | C-B13 |
| XIV-53 | A1 | N | NMe | C-B25 | C-B13 | XIV-54 | A1 | N | NMe | C-B52 | C-B13 |
| XIV-55 | A1 | N | NMe | C-B54 | C-B13 | XIV-56 | A1 | N | NMe | C-B55 | C-B13 |

-continued

| No. | X | Y | W | $Z_1 = Z_2$ | $Z_3 = Z_4 =$ $Z_5 = Z_6$ | No. | X | Y | W | $Z_1 = Z_2$ | $Z_3 = Z_4 =$ $Z_5 = Z_6$ |
|---|---|---|---|---|---|---|---|---|---|---|---|
| XIV-57 | A1 | N | NMe | C-B63 | C-B13 | XIV-58 | A1 | N | NMe | C-B68 | C-B13 |
| XIV-59 | A1 | N | NMe | C-B69 | C-B13 | XIV-60 | A1 | N | NMe | C-B70 | C-B13 |
| XIV-61 | A1 | N | NMe | C-B71 | C-B13 | XIV-62 | A1 | N | NMe | C-B89 | C-B13 |
| XIV-63 | A1 | N | NMe | C-B90 | C-B13 | XIV-64 | A1 | N | NMe | C-B91 | C-B13 | wherein, Compound XV-1 to Compound XV-64 have the structure of Formula XV:

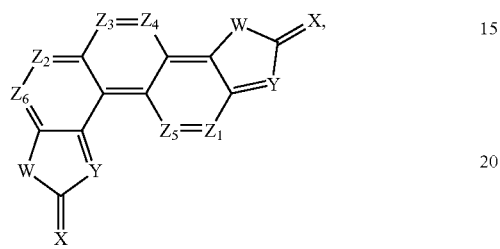

in Formula XV, both of X are the same, both of Y are the same, both of W are the same, $Z_3$, $Z_4$, $Z_5$ and $Z_6$ are the same, $Z_1$ and $Z_2$ are the same, and X, Y, W, $Z_1$, $Z_2$, $Z_3$, $Z_4$, $Z_5$ and $Z_6$ are correspondingly selected from the atoms or groups as shown in the following table:

| No. | X | Y | W | $Z_1 = Z_2$ | $Z_3 = Z_4 =$ $Z_5 = Z_6$ | No. | X | Y | W | $Z_1 = Z_2$ | $Z_3 = Z_4 =$ $Z_5 = Z_6$ |
|---|---|---|---|---|---|---|---|---|---|---|---|
| XV-1 | A1 | N | O | C-B1 | C-B1 | XV-2 | A1 | N | O | C-B13 | C-B13 |
| XV-3 | A1 | N | O | C-B16 | C-B13 | XV-4 | A1 | N | O | C-B17 | C-B13 |
| XV-5 | A1 | N | O | C-B25 | C-B13 | XV-6 | A1 | N | O | C-B52 | C-B13 |
| XV-7 | A1 | N | O | C-B54 | C-B13 | XV-8 | A1 | N | O | C-B55 | C-B13 |
| XV-9 | A1 | N | O | C-B63 | C-B13 | XV-10 | A1 | N | O | C-B68 | C-B13 |
| XV-11 | A1 | N | O | C-B69 | C-B13 | XV-12 | A1 | N | O | C-B70 | C-B13 |
| XV-13 | A1 | N | O | C-B71 | C-B13 | XV-14 | A1 | N | O | C-B89 | C-B13 |
| XV-15 | A1 | N | O | C-B90 | C-B13 | XV-16 | A1 | N | O | C-B91 | C-B13 |
| XV-17 | A1 | N | S | C-B1 | C-B1 | XV-18 | A1 | N | S | C-B13 | C-B13 |
| XV-19 | A1 | N | S | C-B16 | C-B13 | XV-20 | A1 | N | S | C-B17 | C-B13 |
| XV-21 | A1 | N | S | C-B25 | C-B13 | XV-22 | A1 | N | S | C-B52 | C-B13 |
| XV-23 | A1 | N | S | C-B54 | C-B13 | XV-24 | A1 | N | S | C-B55 | C-B13 |
| XV-25 | A1 | N | S | C-B63 | C-B13 | XV-26 | A1 | N | S | C-B68 | C-B13 |
| XV-27 | A1 | N | S | C-B69 | C-B13 | XV-28 | A1 | N | S | C-B70 | C-B13 |
| XV-29 | A1 | N | S | C-B71 | C-B13 | XV-30 | A1 | N | S | C-B89 | C-B13 |
| XV-31 | A1 | N | S | C-B90 | C-B13 | XV-32 | A1 | N | S | C-B91 | C-B13 |
| XV-33 | A1 | N | Se | C-B1 | C-B1 | XV-34 | A1 | N | Se | C-B13 | C-B13 |
| XV-35 | A1 | N | Se | C-B16 | C-B13 | XV-36 | A1 | N | Se | C-B17 | C-B13 |
| XV-37 | A1 | N | Se | C-B25 | C-B13 | XV-38 | A1 | N | Se | C-B52 | C-B13 |
| XV-39 | A1 | N | Se | C-B54 | C-B13 | XV-40 | A1 | N | Se | C-B55 | C-B13 |
| XV-41 | A1 | N | Se | C-B63 | C-B13 | XV-42 | A1 | N | Se | C-B68 | C-B13 |
| XV-43 | A1 | N | Se | C-B69 | C-B13 | XV-44 | A1 | N | Se | C-B70 | C-B13 |
| XV-45 | A1 | N | Se | C-B71 | C-B13 | XV-46 | A1 | N | Se | C-B89 | C-B13 |
| XV-47 | A1 | N | Se | C-B90 | C-B13 | XV-48 | A1 | N | Se | C-B91 | C-B13 |
| XV-49 | A1 | N | NMe | C-B1 | C-B1 | XV-50 | A1 | N | NMe | C-B13 | C-B13 |
| XV-51 | A1 | N | NMe | C-B16 | C-B13 | XV-52 | A1 | N | NMe | C-B17 | C-B13 |
| XV-53 | A1 | N | NMe | C-B25 | C-B13 | XV-54 | A1 | N | NMe | C-B52 | C-B13 |
| XV-55 | A1 | N | NMe | C-B54 | C-B13 | XV-56 | A1 | N | NMe | C-B55 | C-B13 |
| XV-57 | A1 | N | NMe | C-B63 | C-B13 | XV-58 | A1 | N | NMe | C-B68 | C-B13 |
| XV-59 | A1 | N | NMe | C-B69 | C-B13 | XV-60 | A1 | N | NMe | C-B70 | C-B13 |
| XV-61 | A1 | N | NMe | C-B71 | C-B13 | XV-62 | A1 | N | NMe | C-B89 | C-B13 |
| XV-63 | A1 | N | NMe | C-B90 | C-B13 | XV-64 | A1 | N | NMe | C-B91 | C-B13 | wherein, Compound XVI-1 to Compound XVI-64 have the structure of Formula XVI:

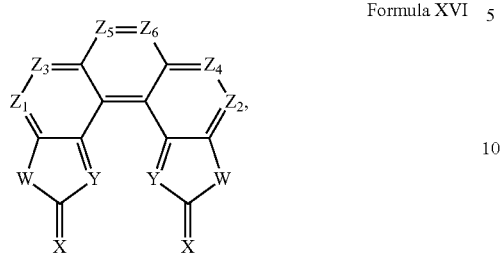

Formula XVI in Formula XVI, both of X are the same, both of Y are the same, both of W are the same, $Z_3$, $Z_4$, $Z_5$ and $Z_6$ are the same, $Z_1$ and $Z_2$ are the same, and X, Y, W, $Z_1$, $Z_2$, $Z_3$, $Z_4$, $Z_5$ and $Z_6$ are correspondingly selected from the atoms or groups as shown in the following table:

| No. | X | Y | W | $Z_1 = Z_2$ | $Z_3 = Z_4 =$ $Z_5 = Z_6$ | No. | X | Y | W | $Z_1 = Z_2$ | $Z_3 = Z_4 =$ $Z_5 = Z_6$ |
|---|---|---|---|---|---|---|---|---|---|---|---|
| XVI-1 | A1 | N | O | C-B1 | C-B1 | XVI-2 | A1 | N | O | C-B13 | C-B13 |
| XVI-3 | A1 | N | O | C-B16 | C-B13 | XVI-4 | A1 | N | O | C-B17 | C-B13 |
| XVI-5 | A1 | N | O | C-B25 | C-B13 | XVI-6 | A1 | N | O | C-B52 | C-B13 |
| XVI-7 | A1 | N | O | C-B54 | C-B13 | XVI-8 | A1 | N | O | C-B55 | C-B13 |
| XVI-9 | A1 | N | O | C-B63 | C-B13 | XVI-10 | A1 | N | O | C-B68 | C-B13 |
| XVI-11 | A1 | N | O | C-B69 | C-B13 | XVI-12 | A1 | N | O | C-B70 | C-B13 |
| XVI-13 | A1 | N | O | C-B71 | C-B13 | XVI-14 | A1 | N | O | C-B89 | C-B13 |
| XVI-15 | A1 | N | O | C-B90 | C-B13 | XVI-16 | A1 | N | O | C-B91 | C-B13 |
| XVI-17 | A1 | N | S | C-B1 | C-B1 | XVI-18 | A1 | N | S | C-B13 | C-B13 |
| XVI-19 | A1 | N | S | C-B16 | C-B13 | XVI-20 | A1 | N | S | C-B17 | C-B13 |
| XVI-21 | A1 | N | S | C-B25 | C-B13 | XVI-22 | A1 | N | S | C-B52 | C-B13 |
| XVI-23 | A1 | N | S | C-B54 | C-B13 | XVI-24 | A1 | N | S | C-B55 | C-B13 |
| XVI-25 | A1 | N | S | C-B63 | C-B13 | XVI-26 | A1 | N | S | C-B68 | C-B13 |
| XVI-27 | A1 | N | S | C-B69 | C-B13 | XVI-28 | A1 | N | S | C-B70 | C-B13 |
| XVI-29 | A1 | N | S | C-B71 | C-B13 | XVI-30 | A1 | N | S | C-B89 | C-B13 |
| XVI-31 | A1 | N | S | C-B90 | C-B13 | XVI-32 | A1 | N | S | C-B91 | C-B13 |
| XVI-33 | A1 | N | Se | C-B1 | C-B1 | XVI-34 | A1 | N | Se | C-B13 | C-B13 |
| XVI-35 | A1 | N | Se | C-B16 | C-B13 | XVI-36 | A1 | N | Se | C-B17 | C-B13 |
| XVI-37 | A1 | N | Se | C-B25 | C-B13 | XVI-38 | A1 | N | Se | C-B52 | C-B13 |
| XVI-39 | A1 | N | Se | C-B54 | C-B13 | XVI-40 | A1 | N | Se | C-B55 | C-B13 |
| XVI-41 | A1 | N | Se | C-B63 | C-B13 | XVI-42 | A1 | N | Se | C-B68 | C-B13 |
| XVI-43 | A1 | N | Se | C-B69 | C-B13 | XVI-44 | A1 | N | Se | C-B70 | C-B13 |
| XVI-45 | A1 | N | Se | C-B71 | C-B13 | XVI-46 | A1 | N | Se | C-B89 | C-B13 |
| XVI-47 | A1 | N | Se | C-B90 | C-B13 | XVI-48 | A1 | N | Se | C-B91 | C-B13 |
| XVI-49 | A1 | N | NMe | C-B1 | C-B1 | XVI-50 | A1 | N | NMe | C-B13 | C-B13 |
| XVI-51 | A1 | N | NMe | C-B16 | C-B13 | XVI-52 | A1 | N | NMe | C-B17 | C-B13 |
| XVI-53 | A1 | N | NMe | C-B25 | C-B13 | XVI-54 | A1 | N | NMe | C-B52 | C-B13 |
| XVI-55 | A1 | N | NMe | C-B54 | C-B13 | XVI-56 | A1 | N | NMe | C-B55 | C-B13 |
| XVI-57 | A1 | N | NMe | C-B63 | C-B13 | XVI-58 | A1 | N | NMe | C-B68 | C-B13 |
| XVI-59 | A1 | N | NMe | C-B69 | C-B13 | XVI-60 | A1 | N | NMe | C-B70 | C-B13 |
| XVI-61 | A1 | N | NMe | C-B71 | C-B13 | XVI-62 | A1 | N | NMe | C-B89 | C-B13 |
| XVI-63 | A1 | N | NMe | C-B90 | C-B13 | XVI-64 | A1 | N | NMe | C-B91 | C-B13 | wherein, Compound XVII-1 to Compound XVII-64 have the structure of Formula XVII:

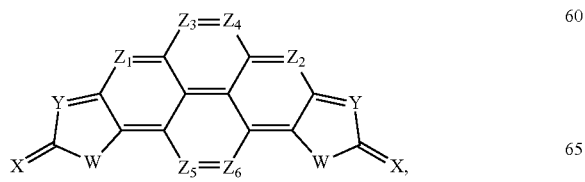

Formula XVII in Formula XVII, both of X are the same, both of Y are the same, both of W are the same, $Z_3$, $Z_4$, $Z_5$ and $Z_6$ are the same, $Z_1$ and $Z_2$ are the same, and X, Y, W, $Z_1$, $Z_2$, $Z_3$, $Z_4$, $Z_5$ and $Z_6$ are correspondingly selected from the atoms or groups as shown in the following table:

| No. | X | Y | W | $Z_1 = Z_2$ | $Z_3 = Z_4 =$ $Z_5 = Z_6$ | No. | X | Y | W | $Z_1 = Z_2$ | $Z_3 = Z_4 =$ $Z_5 = Z_6$ |
|---|---|---|---|---|---|---|---|---|---|---|---|
| XVII-1 | A1 | N | O | C-B1 | C-B1 | XVII-2 | A1 | N | O | C-B13 | C-B13 |
| XVII-3 | A1 | N | O | C-B16 | C-B13 | XVII-4 | A1 | N | O | C-B17 | C-B13 |
| XVII-5 | A1 | N | O | C-B25 | C-B13 | XVII-6 | A1 | N | O | C-B52 | C-B13 |
| XVII-7 | A1 | N | O | C-B54 | C-B13 | XVII-8 | A1 | N | O | C-B55 | C-B13 |
| XVII-9 | A1 | N | O | C-B63 | C-B13 | XVII-10 | A1 | N | O | C-B68 | C-B13 |
| XVII-11 | A1 | N | O | C-B69 | C-B13 | XVII-12 | A1 | N | O | C-B70 | C-B13 |
| XVII-13 | A1 | N | O | C-B71 | C-B13 | XVII-14 | A1 | N | O | C-B89 | C-B13 |
| XVII-15 | A1 | N | O | C-B90 | C-B13 | XVII-16 | A1 | N | O | C-B91 | C-B13 |
| XVII-17 | A1 | N | S | C-B1 | C-B1 | XVII-18 | A1 | N | S | C-B13 | C-B13 |
| XVII-19 | A1 | N | S | C-B16 | C-B13 | XVII-20 | A1 | N | S | C-B17 | C-B13 |
| XVII-21 | A1 | N | S | C-B25 | C-B13 | XVII-22 | A1 | N | S | C-B52 | C-B13 |
| XVII-23 | A1 | N | S | C-B54 | C-B13 | XVII-24 | A1 | N | S | C-B55 | C-B13 |
| XVII-25 | A1 | N | S | C-B63 | C-B13 | XVII-26 | A1 | N | S | C-B68 | C-B13 |
| XVII-27 | A1 | N | S | C-B69 | C-B13 | XVII-28 | A1 | N | S | C-B70 | C-B13 |
| XVII-29 | A1 | N | S | C-B71 | C-B13 | XVII-30 | A1 | N | S | C-B89 | C-B13 |
| XVII-31 | A1 | N | S | C-B90 | C-B13 | XVII-32 | A1 | N | S | C-B91 | C-B13 |
| XVII-33 | A1 | N | Se | C-B1 | C-B1 | XVII-34 | A1 | N | Se | C-B13 | C-B13 |
| XVII-35 | A1 | N | Se | C-B16 | C-B13 | XVII-36 | A1 | N | Se | C-B17 | C-B13 |
| XVII-37 | A1 | N | Se | C-B25 | C-B13 | XVII-38 | A1 | N | Se | C-B52 | C-B13 |
| XVII-39 | A1 | N | Se | C-B54 | C-B13 | XVII-40 | A1 | N | Se | C-B55 | C-B13 |
| XVII-41 | A1 | N | Se | C-B63 | C-B13 | XVII-42 | A1 | N | Se | C-B68 | C-B13 |
| XVII-43 | A1 | N | Se | C-B69 | C-B13 | XVII-44 | A1 | N | Se | C-B70 | C-B13 |
| XVII-45 | A1 | N | Se | C-B71 | C-B13 | XVII-46 | A1 | N | Se | C-B89 | C-B13 |
| XVII-47 | A1 | N | Se | C-B90 | C-B13 | XVII-48 | A1 | N | Se | C-B91 | C-B13 |
| XVII-49 | A1 | N | NMe | C-B1 | C-B1 | XVII-50 | A1 | N | NMe | C-B13 | C-B13 |
| XVII-51 | A1 | N | NMe | C-B16 | C-B13 | XVII-52 | A1 | N | NMe | C-B17 | C-B13 |
| XVII-53 | A1 | N | NMe | C-B25 | C-B13 | XVII-54 | A1 | N | NMe | C-B52 | C-B13 |
| XVII-55 | A1 | N | NMe | C-B54 | C-B13 | XVII-56 | A1 | N | NMe | C-B55 | C-B13 |
| XVII-57 | A1 | N | NMe | C-B63 | C-B13 | XVII-58 | A1 | N | NMe | C-B68 | C-B13 |
| XVII-59 | A1 | N | NMe | C-B69 | C-B13 | XVII-60 | A1 | N | NMe | C-B70 | C-B13 |
| XVII-61 | A1 | N | NMe | C-B71 | C-B13 | XVII-62 | A1 | N | NMe | C-B89 | C-B13 |
| XVII-63 | A1 | N | NMe | C-B90 | C-B13 | XVII-64 | A1 | N | NMe | C-B91 | C-B13 | wherein, Compound XVIII-1 to Compound XVIII-64 have the structure of Formula XVIII:

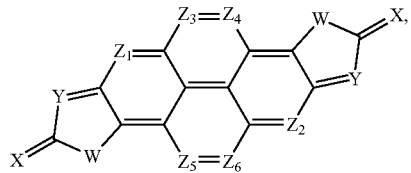

Formula XVIII in Formula XVIII, both of X are the same, both of Y are the same, both of W are the same, $Z_3$, $Z_4$, $Z_5$ and $Z_6$ are the same, $Z_1$ and $Z_2$ are the same, and X, Y, W, $Z_1$, $Z_2$, $Z_3$, $Z_4$, $Z_5$ and $Z_6$ are correspondingly selected from the atoms or groups as shown in the following table:

| No. | X | Y | W | $Z_1 = Z_2$ | $Z_3 = Z_4 =$ $Z_5 = Z_6$ | No. | X | Y | W | $Z_1 = Z_2$ | $Z_3 = Z_4 =$ $Z_5 = Z_6$ |
|---|---|---|---|---|---|---|---|---|---|---|---|
| XVIII-1 | A1 | N | O | C-B1 | C-B1 | XVIII-2 | A1 | N | O | C-B13 | C-B13 |
| XVIII-3 | A1 | N | O | C-B16 | C-B13 | XVIII-4 | A1 | N | O | C-B17 | C-B13 |
| XVIII-5 | A1 | N | O | C-B25 | C-B13 | XVIII-6 | A1 | N | O | C-B52 | C-B13 |
| XVIII-7 | A1 | N | O | C-B54 | C-B13 | XVIII-8 | A1 | N | O | C-B55 | C-B13 |
| XVIII-9 | A1 | N | O | C-B63 | C-B13 | XVIII-10 | A1 | N | O | C-B68 | C-B13 |
| XVIII-11 | A1 | N | O | C-B69 | C-B13 | XVIII-12 | A1 | N | O | C-B70 | C-B13 |
| XVIII-13 | A1 | N | O | C-B71 | C-B13 | XVIII-14 | A1 | N | O | C-B89 | C-B13 |
| XVIII-15 | A1 | N | O | C-B90 | C-B13 | XVIII-16 | A1 | N | O | C-B91 | C-B13 |
| XVIII-17 | A1 | N | S | C-B1 | C-B1 | XVIII-18 | A1 | N | S | C-B13 | C-B13 |

| No. | X | Y | W | $Z_1 = Z_2$ | $Z_3 = Z_4 =$ $Z_5 = Z_6$ | No. | X | Y | W | $Z_1 = Z_2$ | $Z_3 = Z_4 =$ $Z_5 = Z_6$ |
|---|---|---|---|---|---|---|---|---|---|---|---|
| XVIII-19 | A1 | N | S | C-B16 | C-B13 | XVIII-20 | A1 | N | S | C-B17 | C-B13 |
| XVIII-21 | A1 | N | S | C-B25 | C-B13 | XVIII-22 | A1 | N | S | C-B52 | C-B13 |
| XVIII-23 | A1 | N | S | C-B54 | C-B13 | XVIII-24 | A1 | N | S | C-B55 | C-B13 |
| XVIII-25 | A1 | N | S | C-B63 | C-B13 | XVIII-26 | A1 | N | S | C-B68 | C-B13 |
| XVIII-27 | A1 | N | S | C-B69 | C-B13 | XVIII-28 | A1 | N | S | C-B70 | C-B13 |
| XVIII-29 | A1 | N | S | C-B71 | C-B13 | XVIII-30 | A1 | N | S | C-B89 | C-B13 |
| XVIII-31 | A1 | N | S | C-B90 | C-B13 | XVIII-32 | A1 | N | S | C-B91 | C-B13 |
| XVIII-33 | A1 | N | Se | C-B1 | C-B1 | XVIII-34 | A1 | N | Se | C-B13 | C-B13 |
| XVIII-35 | A1 | N | Se | C-B16 | C-B13 | XVIII-36 | A1 | N | Se | C-B17 | C-B13 |
| XVIII-37 | A1 | N | Se | C-B25 | C-B13 | XVIII-38 | A1 | N | Se | C-B52 | C-B13 |
| XVIII-39 | A1 | N | Se | C-B54 | C-B13 | XVIII-40 | A1 | N | Se | C-B55 | C-B13 |
| XVIII-41 | A1 | N | Se | C-B63 | C-B13 | XVIII-42 | A1 | N | Se | C-B68 | C-B13 |
| XVIII-43 | A1 | N | Se | C-B69 | C-B13 | XVIII-44 | A1 | N | Se | C-B70 | C-B13 |
| XVIII-45 | A1 | N | Se | C-B71 | C-B13 | XVIII-46 | A1 | N | Se | C-B89 | C-B13 |
| XVIII-47 | A1 | N | Se | C-B90 | C-B13 | XVIII-48 | A1 | N | Se | C-B91 | C-B13 |
| XVIII-49 | A1 | N | NMe | C-B1 | C-B1 | XVIII-50 | A1 | N | NMe | C-B13 | C-B13 |
| XVIII-51 | A1 | N | NMe | C-B16 | C-B13 | XVIII-52 | A1 | N | NMe | C-B17 | C-B13 |
| XVIII-53 | A1 | N | NMe | C-B25 | C-B13 | XVIII-54 | A1 | N | NMe | C-B52 | C-B13 |
| XVIII-55 | A1 | N | NMe | C-B54 | C-B13 | XVIII-56 | A1 | N | NMe | C-B55 | C-B13 |
| XVIII-57 | A1 | N | NMe | C-B63 | C-B13 | XVIII-58 | A1 | N | NMe | C-B68 | C-B13 |
| XVIII-59 | A1 | N | NMe | C-B69 | C-B13 | XVIII-60 | A1 | N | NMe | C-B70 | C-B13 |
| XVIII-61 | A1 | N | NMe | C-B71 | C-B13 | XVIII-62 | A1 | N | NMe | C-B89 | C-B13 |
| XVIII-63 | A1 | N | NMe | C-B90 | C-B13 | XVIII-64 | A1 | N | NMe | C-B91 | C-B13 | wherein, Compound XIX-1 to Compound XIX-64 have the structure of Formula XIX:

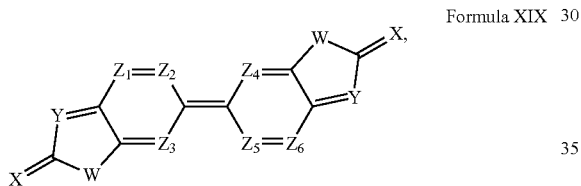

Formula XIX in Formula XIX, both of X are the same, both of Y are the same, both of W are the same, $Z_1$, $Z_2$, $Z_5$ and $Z_6$ are the same, $Z_3$ and $Z_4$ are the same, and X, Y, W, $Z_1$, $Z_2$, $Z_3$, $Z_4$, $Z_5$ and $Z_6$ are correspondingly selected from the atoms or groups as shown in the following table:

| No. | X | Y | W | $Z_1 = Z_2 =$ $Z_3 = Z_4$ | $Z_5 = Z_6$ | No. | X | Y | W | $Z_1 = Z_2 =$ $Z_3 = Z_4$ | $Z_5 = Z_6$ |
|---|---|---|---|---|---|---|---|---|---|---|---|
| XIX-1 | A1 | N | O | C-B1 | C-B1 | XIX-2 | A1 | N | O | C-B13 | C-B13 |
| XIX-3 | A1 | N | O | C-B16 | C-B13 | XIX-4 | A1 | N | O | C-B17 | C-B13 |
| XIX-5 | A1 | N | O | C-B25 | C-B13 | XIX-6 | A1 | N | O | C-B52 | C-B13 |
| XIX-7 | A1 | N | O | C-B54 | C-B13 | XIX-8 | A1 | N | O | C-B55 | C-B13 |
| XIX-9 | A1 | N | O | C-B63 | C-B13 | XIX-10 | A1 | N | O | C-B68 | C-B13 |
| XIX-11 | A1 | N | O | C-B69 | C-B13 | XIX-12 | A1 | N | O | C-B70 | C-B13 |
| XIX-13 | A1 | N | O | C-B71 | C-B13 | XIX-14 | A1 | N | O | C-B89 | C-B13 |
| XIX-15 | A1 | N | O | C-B90 | C-B13 | XIX-16 | A1 | N | O | C-B91 | C-B13 |
| XIX-17 | A1 | N | S | C-B1 | C-B1 | XIX-18 | A1 | N | S | C-B13 | C-B13 |
| XIX-19 | A1 | N | S | C-B16 | C-B13 | XIX-20 | A1 | N | S | C-B17 | C-B13 |
| XIX-21 | A1 | N | S | C-B25 | C-B13 | XIX-22 | A1 | N | S | C-B52 | C-B13 |
| XIX-23 | A1 | N | S | C-B54 | C-B13 | XIX-24 | A1 | N | S | C-B55 | C-B13 |
| XIX-25 | A1 | N | S | C-B63 | C-B13 | XIX-26 | A1 | N | S | C-B68 | C-B13 |
| XIX-27 | A1 | N | S | C-B69 | C-B13 | XIX-28 | A1 | N | S | C-B70 | C-B13 |
| XIX-29 | A1 | N | S | C-B71 | C-B13 | XIX-30 | A1 | N | S | C-B89 | C-B13 |
| XIX-31 | A1 | N | S | C-B90 | C-B13 | XIX-32 | A1 | N | S | C-B91 | C-B13 |
| XIX-33 | A1 | N | Se | C-B1 | C-B1 | XIX-34 | A1 | N | Se | C-B13 | C-B13 |
| XIX-35 | A1 | N | Se | C-B16 | C-B13 | XIX-36 | A1 | N | Se | C-B17 | C-B13 |
| XIX-37 | A1 | N | Se | C-B25 | C-B13 | XIX-38 | A1 | N | Se | C-B52 | C-B13 |
| XIX-39 | A1 | N | Se | C-B54 | C-B13 | XIX-40 | A1 | N | Se | C-B55 | C-B13 |
| XIX-41 | A1 | N | Se | C-B63 | C-B13 | XIX-42 | A1 | N | Se | C-B68 | C-B13 |
| XIX-43 | A1 | N | Se | C-B69 | C-B13 | XIX-44 | A1 | N | Se | C-B70 | C-B13 |
| XIX-45 | A1 | N | Se | C-B71 | C-B13 | XIX-46 | A1 | N | Se | C-B89 | C-B13 |
| XIX-47 | A1 | N | Se | C-B90 | C-B13 | XIX-48 | A1 | N | Se | C-B91 | C-B13 |

-continued

| No. | X | Y | W | $Z_1 = Z_2 =$ $Z_3 = Z_4$ | $Z_1 = Z_2 =$ $Z_5 = Z_6$ | No. | X | Y | W | $Z_3 = Z_4$ | $Z_1 = Z_2 =$ $Z_5 = Z_6$ |
|---|---|---|---|---|---|---|---|---|---|---|---|
| XIX-49 | A1 | N | NMe | C-B1 | C-B1 | XIX-50 | A1 | N | NMe | C-B13 | C-B13 |
| XIX-51 | A1 | N | NMe | C-B16 | C-B13 | XIX-52 | A1 | N | NMe | C-B17 | C-B13 |
| XIX-53 | A1 | N | NMe | C-B25 | C-B13 | XIX-54 | A1 | N | NMe | C-B52 | C-B13 |
| XIX-55 | A1 | N | NMe | C-B54 | C-B13 | XIX-56 | A1 | N | NMe | C-B55 | C-B13 |
| XIX-57 | A1 | N | NMe | C-B63 | C-B13 | XIX-58 | A1 | N | NMe | C-B68 | C-B13 |
| XIX-59 | A1 | N | NMe | C-B69 | C-B13 | XIX-60 | A1 | N | NMe | C-B70 | C-B13 |
| XIX-61 | A1 | N | NMe | C-B71 | C-B13 | XIX-62 | A1 | N | NMe | C-B89 | C-B13 |
| XIX-63 | A1 | N | NMe | C-B90 | C-B13 | XIX-64 | A1 | N | NMe | C-B91 | C-B13 |

17. An electroluminescent device comprising:
an anode,
a cathode, and
an organic layer disposed between the anode and the cathode, wherein the organic layer comprises the compound of claim 1.

18. The electroluminescent device according to claim 17, wherein the organic layer is a hole injection layer or a hole transporting layer, and the hole injection layer or the hole transporting layer is formed by the compound alone.

19. The electroluminescent device according to claim 17, wherein the organic layer is a hole injection layer or a hole transporting layer, and the hole injection layer or the hole transporting layer further comprises at least one hole transporting material; and wherein the molar doping ratio of the compound to the hole transporting material is from 10000:1 to 1:10000.

20. The electroluminescent device according to claim 19, wherein the hole transporting material comprises a compound having a triarylamine unit, a spirobifluorene compound, a pentacene compound, an oligothiophene compound, an oligophenyl compound, an oligophenylene vinyl compound, an oligofluorene compound, a porphyrin complex or a metal phthalocyanine complex.

21. The electroluminescent device according to claim 17, the electroluminescent device comprises a plurality of stacks disposed between the anode and the cathode, wherein the stacks comprise a first light-emitting layer and a second light-emitting layer, wherein the first stack comprises a first light-emitting layer, and the second stack comprises a second light-emitting layer, and a charge generation layer is disposed between the first stack and the second stack, wherein the charge generation layer comprises a p-type charge generation layer and an n-type charge generation layer;
wherein the p-type charge generating layer comprises the compound.

22. The electroluminescent device according to claim 21, wherein the p-type charge generation layer further comprises at least one hole transporting material, wherein the molar doping ratio of the compound to the hole transporting material is from 10000:1 to 1:10000.

23. The electroluminescent device according to claim 21, the charge generation layer further includes a buffer layer disposed between the p-type charge generation layer and the n-type charge generation layer, wherein the buffer layer comprises the compound.

24. The electroluminescent device according to claim 17, the electroluminescent device is fabricated via vacuum deposition methods.

25. A compound formulation comprising the compound of claim 1.

26. The compound according to claim 8, wherein Z is, at each occurrence identically or differently, selected from CR, and wherein at least one of R is selected from the group having at least one electron-withdrawing group.

27. The compound according to claim 9, wherein each of R, R', R'', R''' and $R_N$ is the group having at least one electron-withdrawing group.

28. The compound according to claim 11, wherein the electron-withdrawing group is selected from the group consisting of F, $CF_3$, $OCF_3$, $SF_5$, $SO_2CF_3$, cyano, isocyano, SCN, OCN, pyrimidinyl, triazinyl, and combinations thereof.

29. The compound according to claim 12, wherein $R_1$ is selected, at each occurrence, identically or differently, from the group consisting of F, $CF_3$, $OCF_3$, $SF_5$, $SO_2CF_3$, cyano, isocyano, SCN, OCN, pentafluorophenyl, 4-cyanotetrafluorophenyl, tetrafluoropyridyl, pyrimidinyl, triazinyl, and combinations thereof.

30. The compound according to claim 14, wherein R is, at each occurrence identically or differently, selected from the group consisting of hydrogen, deuterium, methyl, isopropyl, $NO_2$, $SO_2CH_3$, $SCF_3$, $C_2F_5$, $OC_2F_5$, $OCH_3$, p-methylphenyl, diphenylmethylsilyl, phenyl, methoxyphenyl, 2,6-diisopropylphenyl, biphenyl, polyfluorophenyl, difluoropyridyl, nitrophenyl, dimethylthiazolyl, CN, vinyl substituted with one or more of CN and $CF_3$, ethynyl substituted with one of CN and $CF_3$, dimethylphosphoroso, diphenylphosphoroso, F, $CF_3$, $OCF_3$, $SF_5$, $SO_2CF_3$, cyano, isocyano, SCN, OCN, trifluoromethylphenyl, trifluoromethoxyphenyl, bis(trifluoromethyl)phenyl, bis(trifluoromethoxy)phenyl, 4-cyanotetrafluorophenyl, phenyl or biphenyl substituted with one or more of F, CN and $CF_3$, tetrafluoropyridyl, pyrimidinyl, triazinyl, pyridyl, diphenylboranyl, oxaboraanthryl, and combinations thereof.

31. The electroluminescent device according to claim 22, wherein the hole transporting material comprises a compound having a triarylamine unit, a spirobifluorene compound, a pentacene compound, an oligothiophene compound, an oligophenyl compound, an oligophenylene vinyl compound, an oligofluorene compound, a porphyrin complex or a metal phthalocyanine complex.

32. The compound according to claim 1, wherein B is selected from a substituted or unsubstituted conjugated unsaturated fused aryl ring having 10 to 30 ring atoms, or a substituted or unsubstituted conjugated unsaturated fused heteroaryl ring having 10 to 30 ring atoms, or combinations thereof.
33. The compound according to claim 2, the compound is selected from the structure of any one of Formula III to Formula VI:
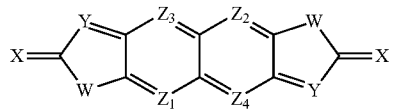
Formula III
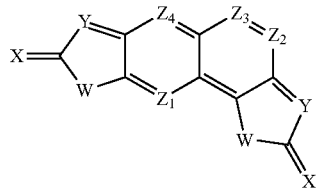
Formula IV
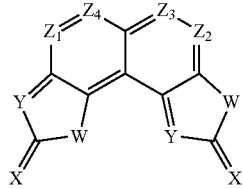
Formula V
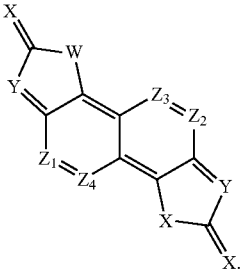
Formula VI
* * * * *